(12) United States Patent
Pombo et al.

(10) Patent No.: US 10,526,639 B2
(45) Date of Patent: Jan. 7, 2020

(54) GENOME ARCHITECTURE MAPPING

(71) Applicants: MAX-DELBRÜCK-CENTRUM FÜR MOLEKULARE MEDIZIN IN DER HELMHOLTZ-GEMEINSCHAFT, Berlin (DE); CAMBRIDGE ENTERPRISE LIMITED, Cambridge (GB)

(72) Inventors: Ana Pombo, Berlin (DE); Paul Edwards, Cambridge (GB); Mario Nicodemi, Naples (IT); Antonio Scialdone, Cambridge (GB); Robert Beagrie, London (GB)

(73) Assignees: MAX-DELBRÜCK-CENTRUM FÜR MOLEKULARE MEDIZIN IN DER HELMHOLTZ-GEMEINSCHAFT, Berlin (DE); CAMBRIDGE ENTERPRISE LTD., Cambridge (GB)

( * ) Notice: Subject to any disclaimer, the term of this patent is extended or adjusted under 35 U.S.C. 154(b) by 0 days.

(21) Appl. No.: 15/533,890

(22) PCT Filed: Dec. 11, 2015

(86) PCT No.: PCT/EP2015/079413
§ 371 (c)(1),
(2) Date: Jun. 7, 2017

(87) PCT Pub. No.: WO2016/092070
PCT Pub. Date: Jun. 16, 2016

(65) Prior Publication Data
US 2017/0342462 A1  Nov. 30, 2017

(30) Foreign Application Priority Data
Dec. 11, 2014 (EP) .................... 14197405

(51) Int. Cl.
| C12Q 1/68 | (2018.01) |
| G16B 20/00 | (2019.01) |
| C12N 15/10 | (2006.01) |

(52) U.S. Cl.
CPC ........... *C12Q 1/68* (2013.01); *C12N 15/1003* (2013.01); *G16B 20/00* (2019.02)

(58) Field of Classification Search
CPC .. C12Q 1/6869; G06F 19/18; G16B 20/00–40
See application file for complete search history.

(56) References Cited

U.S. PATENT DOCUMENTS

2001/0051344 A1* 12/2001 Shalon .................. B01L 3/0244
435/6.11

FOREIGN PATENT DOCUMENTS

| JP | 2009-500031 A | 1/2009 |
| WO | 2007/004057 A2 | 1/2007 |

OTHER PUBLICATIONS

Branco et al. Intermingling of chromosome territories in interphase suggests role in translocations and transcription-dependent associations. PLoS Biology, Vo. 4, No. 5, e138, 2006, printed as pp. 1/9-9/9, and 8 pages of Supporting Information. (Year: 2006).*
Chen et al. Nano-dissection and sequencing of DNA at single sub-nuclear structures. Small, vol. 10, No. 16, pp. 3267-3274, May 3, 2014, including pp. 1/4-4/4 of Supporting Information. (Year: 2014).*
Beagrie et al. Complex multi-enhancer contacts captured by genome architecture mapping. Nature, vol. 549, pp. 519-524, Mar. 2017, including pp. 1/4-4/4 of Methods, pp. 1/15-15/15 of Extended Data Figures, and pp. 1/25-25/25 of Supplementary Notes 1 to 3. (Year: 2017).*
Kroese et al. Genetic tests and their evaluation: Can we answer the key questions? Genetics in Medicine, vol. 6, pp. 475-480, 2004. (Year: 2004).*
Maeburn et al. Spatial genome organization and its emerging role as a potential diagnosis tool. Frontiers in Genetics, vol. 7, Article 134, Jul. 26, 2016, printed as pp. 1-18. (Year: 2016).*
Babu et al., "Eukaryotic gene regulation in three dimensions and its impact on genome evolution," *Current Opinion in Genetics & Development* 18:571-582 (2008).
Branco et al., "Changes in chromosome organization during PHA-activation of resting human lymphocytes measured by cryo-FISH," *Chromosome Research* 16:413-426 (2008).
Combs et al., "Sequencing mRNA from Cryo-Sliced *Drosophila* Embryos to Determine Genome-Wide Spatial Patterns of Gene Expression," *PLOS One* 8(8):e71820 (7 pages) (Aug. 2013).
Junker et al., "Genome-wide RNA Tomography in the Zebrafish Embryo," *Cell* 159:662-675 (Oct. 23, 2014).
Robinson et al., "Correlative Fluorescence and Electron Microscopy on Ultrathin Cryosections: Bridging the Resolution Gap," *The Journal of Histochemistry & Cytochemistry* 49(7):803-808 (2001).
Abranches et al., "Neural Differentiation of Embryonic Stem Cells In Vitro: A Road Map to Neurogenesis in the Embryo," *PLoS ONE* 4(7):e6286, 2009, 14 pages.

(Continued)

*Primary Examiner* — Jennifer Dunston
(74) *Attorney, Agent, or Firm* — Seed IP Law Group LLP

(57) ABSTRACT

The present invention relates to the field of analysis of the three-dimensional structure of the genome, i.e., for genome architecture mapping (GAM). The invention provides a method of determining spatial proximity of a plurality of nucleic acid loci in a compartment such as the cell nucleus, by exploiting their co-segregation amongst fractions of that compartment, identified upon separation of the nucleic acid loci from each other depending on their localization in the compartment to obtain a collection of fractions, e.g., by cryo-sectioning or cryo-milling the compartment; determining the presence or absence of the plurality of loci in the fractions; and determining the co-segregation of the plurality of loci. Co-segregation may then be analysed with statistical methods to determine spatial proximity. The method can be used e.g., for determining physical distance between a plurality of loci; and mapping loci and/or genome architecture, e.g., in the nucleus; identification of regulatory regions directing expression of a specific gene through spatial contacts; identifying the nuclear position of an exogenous nucleic acid in the nucleus and/or diagnosing a disease associated with a disturbed co-segregation of loci.

17 Claims, 31 Drawing Sheets

(56) References Cited

OTHER PUBLICATIONS

Figure 2A:
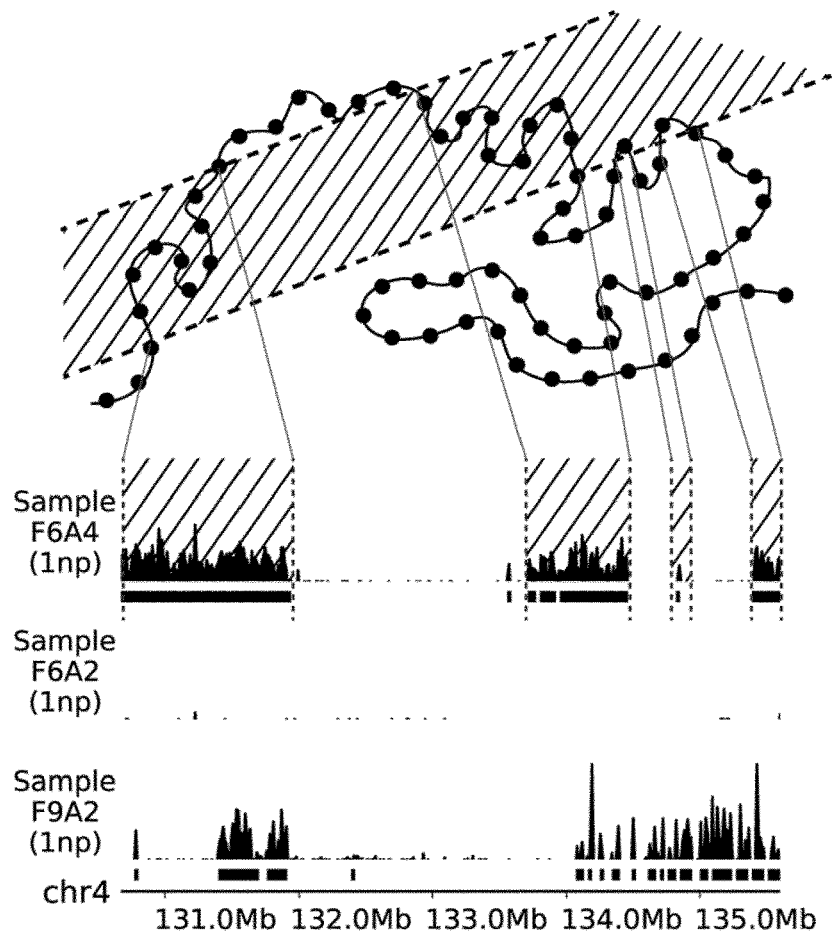
Figure 2B:
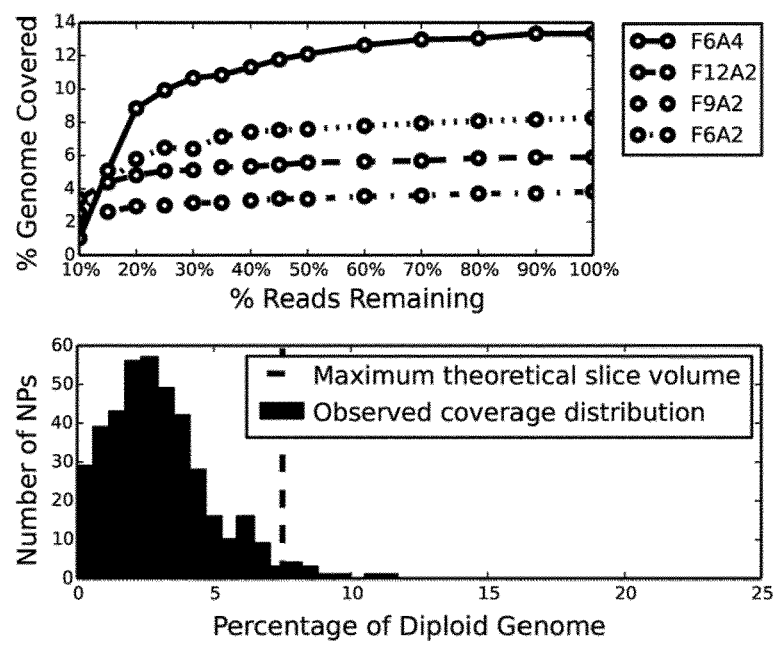

Barbieri et al., "Complexity of chromatin folding is captured by the strings and binders switch model," *PNAS* 109(40):16173-16178, 2012.
Barbieri et al., "Active and poised promoter states drive folding of the extended HoxB locus in mouse embryonic stem cells," *Nature Structural & Molecular Biology* 24(6):515-524, 2017, 13 pages.
Barutcu et al., "Chromatin interaction analysis reveals changes in small chromosome and telomere clustering between epithelial and breast cancer cells," *Genome Biology* 16:214, 2015, 14 pages.
Baslan et al., "Genome-wide copy number analysis of single cells," *Nature Protocols* 7(6):1024-1041, 2012.
Beagrie et al., "GAMtools: an automated pipeline for analysis of Genome Architecture Mapping data," *BioR$_x$iv*, downloaded from https://www.biorxiv.org/content/early/2017/03/20/114710, 2017, 21 pages.
Belmont, "Large-scale chromatin organization: the good, the surprising, and the still perplexing," *Current Opinion in Cell Biology* 26:69-78, 2014.
Binder, "Applications of Monte Carlo methods to statistical physics," *Rep. Prog. Phys.* 60:487-559, 1997.
Brookes et al., "Polycomb Associates Genome-wide with a Specific RNA Polymerase II Variant, and Regulates Metabolic Genes in ESCs," *Cell Stem Cell* 10:157-170, 2012.
Chen et al., "Enhancer identification in mouse embryonic stem cells using integrative modeling of chromatin and genomic features," *BMC Genomics* 13:152, 2012, 19 pages.
Chetverin et al., "Molecular Colony Technique: A New Tool for Biomedical Research and Clinical Practice," *Progress in Nucleic Acid Research* 82:219-255, 2008.
Dear et al., "Happy mapping: a proposal for linkage mapping the human genome," *Nucleic Acids Research* 17(17):6795-6807, 1989.
Deng et al., "Manipulating nuclear architecture," *Current Opinion in Genetics & Development* 25:1-7, 2014.
Dey et al., "Integrated genome and transcriptome sequencing of the same cell," *Nature Biotechnology* 33(3):285-291, 2015.
Dixon et al., "Topological domains in mammalian genomes identified by analysis of chromatin interactions," *Nature* 485:376-380, 2012.
Dubochet et al., "Cryo-electron microscopy of vitrified specimens," *Quarterly Review of Biophysics* 21(2):129-228, 1988.
Emmert-Buck et al., "Laser Capture Microdissection," *Science* 274(5289):998-1001, 1996.
Ferrai et al., "Poised Transcription Factories Prime Silent uPA Gene Prior to Activation," *PLoS Biology* 8(1):e1000270, 2010, 16 pages.
Gavrilov et al., "Disclosure of a structural milieu for the proximity ligation reveals the elusive nature of an active chromatin hub," *Nucleic Acids Research* 41(6):3563-3575, 2013.
Gavrilov et al., "Quantitative analysis of genomic element interactions by molecular colony technique," *Nucleic Acids Research* 42(5):e36, 2014, 11 pages.
Guillot et al., "Fixation-induced redistribution of hyperphosphorylated RNA polymerase II in the nucleus of human cells," *Experimental Cell Research* 295:460-468, 2004.
Hakhverdyan et al., "Rapid, optimized interactomic screening," *Nature Methods* 12(6):553-560, 2015, 10 pages.
Hu et al., "HiCNorm: removing biases in Hi-C data via Poisson regression," *Bioinformatics* 28(23):3131-3133, 2012.
Imakaev et al., "Iterative correction of Hi-C data reveals hallmarks of chromosome organization," *Nature Methods* 9(10):999-1003, 2012, 8 pages.
Ing-Simmons et al., "Spatial enhancer clustering and regulation of enhancer-proximal genes by cohesion," *Genome Research* 25:504-513, 2015.
Khalil et al., "Chromosome territories have a highly nonspherical morphology and nonrandom positioning," *Chromosome Research* 15:899-916, 2007.

Kruse et al., "A complex network framework for unbiased statistical analyses of DNA—DNA contact maps," *Nucleic Acids Research* 41(2):701-710, 2013.
Kubben et al., "Mapping of lamin A- and progerin-interacting genome regions," *Chromosoma* 121:447-464, 2012.
Langmead et al., "Fast gapped-read alignment with Bowtie 2," *Nature Methods* 9(4): 357-360, 2012.
Leshner et al., "Locus-specific gene repositioning in prostate cancer," *Molecular Biology of the Cell* 27:236-246, 2016.
Lettice et al., "Enhancer-Adoption as a Mechanism of Human Developmental Disease," *Human Mutation* 32(12):1492-1499, 2011.
Lewontin, "The Interaction of Selection and Linkage. I. General Considerations; Heterotic Models," *Genetics* 49:49-67, 1964.
Lieberman-Aiden et al., "Comprehensive mapping of long range interactions reveals folding principles of the human genome," *Science* 326(5950):289-293, 2009.
Liu et al., "3D imaging of Sox2 enhancer clusters in embryonic stem cells," *eLife* 3:e04236, 2014, 29 pages.
Lučić, "Cryo-electron tomography: The challenge of doing structural biology in situ," *J. Cell Biol.* 202(3):407-419, 2013.
Markenscoff-Papadimitriou et al., "Enhancer Interaction Networks as a Means for Singular Olfactory Receptor Expression," *Cell* 159:543-557, 2014.
Mateos-Langerak et al., "Spatially confined folding of chromatin in the interphase nucleus," *PNAS* 106(10):3812-3817, 2009.
Maxwell et al., "Pitx3 regulates tyrosine hydroxylase expression in the substantia nigra and identifies a subgroup of mesencephalic dopaminergic progenitor neurons during mouse development," *Developmental Biology* 282:467-479, 2005.
Mayer et al., "Common themes and cell type specific variations of higher order chromatin arrangements in the mouse," *BMC Cell Biology* 6:44, 2005, 22 pages.
Meaburn et al., "Disease-specific gene repositioning in breast cancer," *J. Cell Biol.* 187(6):801-812, 2009.
Min et al., "Regulating RNA polymerase pausing and transcription elongation in embryonic stem cells," *Genes and Development* 25:742-754, 2011.
Northcott et al., "Enhancer hijacking activates GFI1 family oncogenes in medulloblastoma," *Nature* 511(7510):428-434, 2014, 19 pages.
O'Sullivan et al., "The statistical-mechanics of chromosome conformation capture," *Nucleus* 4(5):390-398, 2013.
Oeffinger et al., "Comprehensive analysis of diverse ribonucleoprotein complexes," *Nature Methods* 4(11):951-956, 2007.
Oliphant, "Python for Scientific Computing," *Computing in Science & Engineering* 9(3):10-20, 2007.
Osborne et al., "Active genes dynamically colocalize to shared sites of ongoing transcription," *Nature Genetics* 36(10):1065-1071, 2004.
Pauciullo et al., "Development of a sequential multicolor-FISH approach with 13 chromosome-specific painting probes for the rapid identification of river buffalo (*Bubalus bubalis*, 2n=50) chromosomes," *J Appl Genetics* 55:397-401, 2014.
Peric-Hupkes et al., "Molecular Maps of the Reorganization of Genome-Nuclear Lamina Interactions during Differentiation," *Molecular Cell* 38:603-613, 2010.
Pombo et al., "Bridging the Resolution Gap: Imaging the Same Transcription Factories in Cryosections by Light and Electron Microscopy," *The Journal of Histochemistry & Cytochemistry* 47(4):471-480, 1999.
Pombo, "Cellular genomics: which genes are transcribed, when and where?" *TRENDS in Biochemical Sciences* 28(1):6-9, 2003.
Pombo et al., "Regional specialization in human nuclei: visualization of discrete sites of transcription by RNA polymerase III," *The EMBO Journal* 18(8):2241-2253, 1999.
Quinlan et al., "BEDTools: a flexible suite of utilities for comparing genomic features," *Bioinformatics* 26(6):841-842, 2010.
Schoenfelder et al., "Preferential associations between co-regulated genes reveal a transcriptional interactome in erythroid cells," *Nature Genetics* 42(1):53-61, 2010, 10 pages.
Sexton et al., "Three-Dimensional Folding and Functional Organization Principles of the *Drosophila* Genome," *Cell* 148:458-472, 2012.

(56) References Cited

OTHER PUBLICATIONS

Simonis et al., "Nuclear organization of active and inactive chromatin domains uncovered by chromosome conformation capture—on-chip (4C)," *Nature Genetics* 38(11):1348-1354, 2006.
Smemo et al., "Obesity-associated variants within FTO form long-range functional connections with IRX3," *Nature* 507:371-375, 2014, (with supplementary material) 17 pages.
Stock et al., "Ring 1-mediated ubiquitination of H2A restrains poised RNA polymerase II at bivalent genes in mouse ES cells," *Nature Cell Biology* 9(12):1428-1435, 2007, (with supplementary material) 28 pages.
Van Berkum et al., "Hi-C: A Method to Study the Three-dimensional Architecture of Genomes," *Journal of Visualized Experiments* 39:e1869, 2010, 7 pages.
Whyte et al., "Master Transcription Factors and Mediator Establish Super-Enhancers at Key Cell Identity Genes," *Cell* 153:307-319, 2013.
Williamson et al., "Spatial genome organization: contrasting views from chromosome conformation capture and fluorescence in situ hybridization," *Genes and Development* 28:2778-2791, 2014.
Yaffe et al., "Probabilistic modeling of Hi-C contact maps eliminates systematic biases to characterize global chromosomal architecture," *Nature Genetics* 43(11):1059-1065, 2011, 9 pages.
Ying et al., "Conversion of embryonic stem cells into neuroectodermal precursors in adherent monoculture," *Nature Biotechnology* 21:183-186, 2003.
Yu et al., , "A comparative encyclopedia of DNA elements in the mouse genome," *Nature* 515(7527):355-364, 2014.

\* cited by examiner

Fig. 1
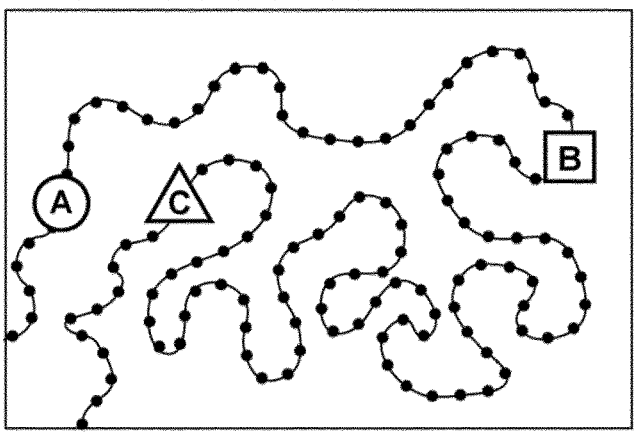
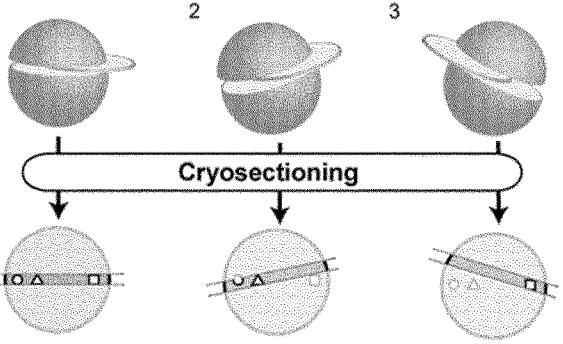
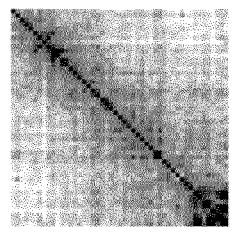

Fig. 2c
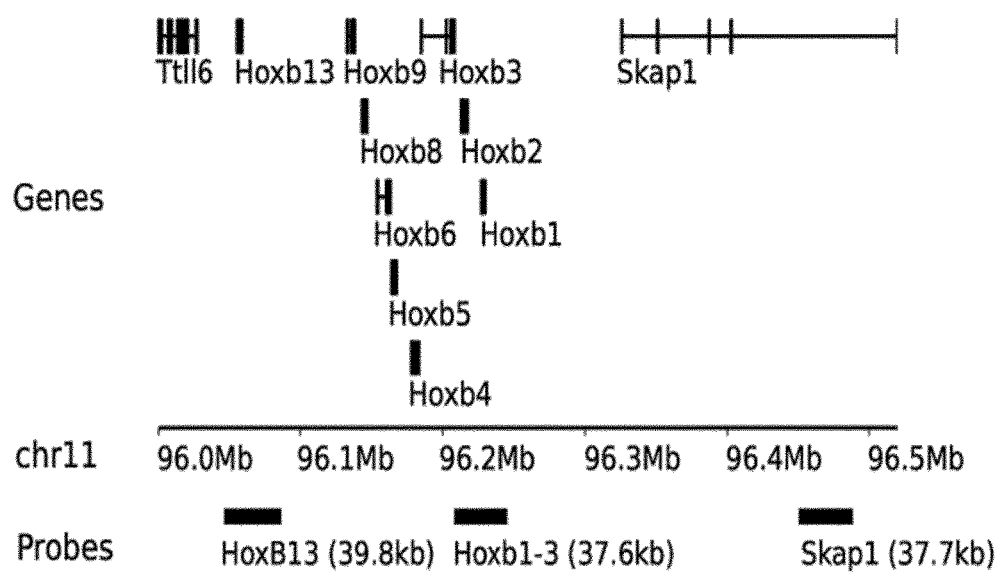
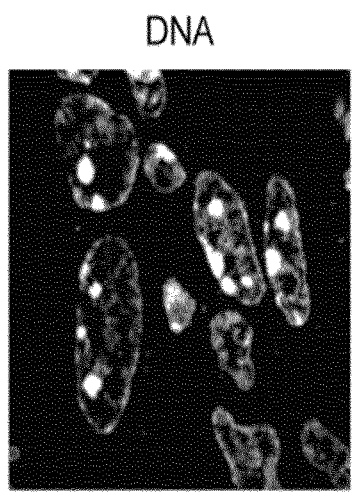
DNA
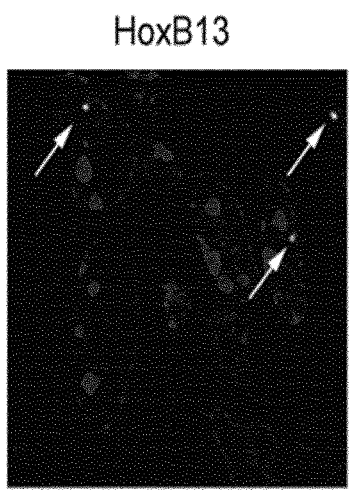
HoxB13
Locus Detection Frequency
|  | FISH (n>1800) | GAM (n=408) |
|---|---|---|
| HoxB13 | 11.6% | 7.6% |
| HoxB1-2 | 8.9% | 9.1% |
| Skap1 | 12.9% | 8.6% |

Fig. 4

| Limitation | GCC | Hi-C | TCC | scHi-C | GAM |
|---|---|---|---|---|---|
| Interaction multiplicity affects strength of detected interactions, since ligation only captures two partners per fragment[19,20] | ✘ Only two partners per fragment | ✘ Only two partners per fragment | ✘ Only two partners per fragment | ✘ Only two partners per fragment | ✓ Does not depend on ligation |
| Mild fixation can lead to artefactual genome architecture due to chromatin collapse[2] | ✘ Mild fixation | ✘ Mild fixation | ✘ Mild fixation | ✘ Mild fixation | ✓ Strong fixation |
| Incompletely solubilized subnuclear structures are used for subsequent ligation[21] | ✘ Ligation events can occur within insoluble fraction | ✘ Ligation events can occur within insoluble fraction | ⓘ Ligation on beads should reduce influence of insoluble material | ✘ Chromatin is not solubilized | ✓ Does not depend on ligation |
| Over/under-representation of specific restriction fragments (depending on enzyme digestion efficiency, fragment size, GC content etc.)[20,22–25] | ⓘ Partial correction using sequencing count from non-ligated fragments | ✘ Incomplete correction in data processing stage | ✘ Incomplete correction in data processing stage | ✘ Incomplete correction in data processing stage | ✓ < 1% of over-represented loci |
| Detection of chromatin contacts is dependent on protein occupancy of DNA | ✘ Formaldehyde crosslinks require proteins | ✘ Formaldehyde crosslinks require proteins | ✘ Formaldehyde crosslinks require proteins | ✘ Formaldehyde crosslinks require proteins | ✓ Interacting partners do not need to be directly crosslinked |
| Requires large numbers of cells[26] | ✘ Millions of cells | ✘ Millions of cells | ✘ Millions of cells | ✓ Hundreds of cells | ✓ Hundreds of cells |
| Requires purification of target cells from surrounding tissues[26] | ✘ Cell suspension or culture | ✘ Cell suspension or culture | ✘ Cell suspension or culture | ⓘ Not yet demonstrated on sub-populations | ✓ Target cells easily isolated by laser-microdissection |
| Cannot detect inter-dependency of interactions in the same nucleus | ✘ No detection of inter-dependencies | ✘ No detection of inter-dependencies | ✘ No detection of inter-dependencies | ⓘ Theoretically possible | ⓘ Theoretically possible |
| Cannot detect locus radial positions | ✘ No detection of radial position | ✘ No detection of radial position | ✘ No detection of radial position | ✘ No detection of radial position | ✓ Capable of extracting radial positions |
| Ligation frequency is not directly related to any physical parameter[27] | ✘ Measures ligation frequency | ✘ Measures ligation frequency | ✘ Measures ligation frequency | ✘ Measures ligation frequency | ✓ Measures distance as a function of locus co-segregation |

Fig. 5a-d

Fig. 6
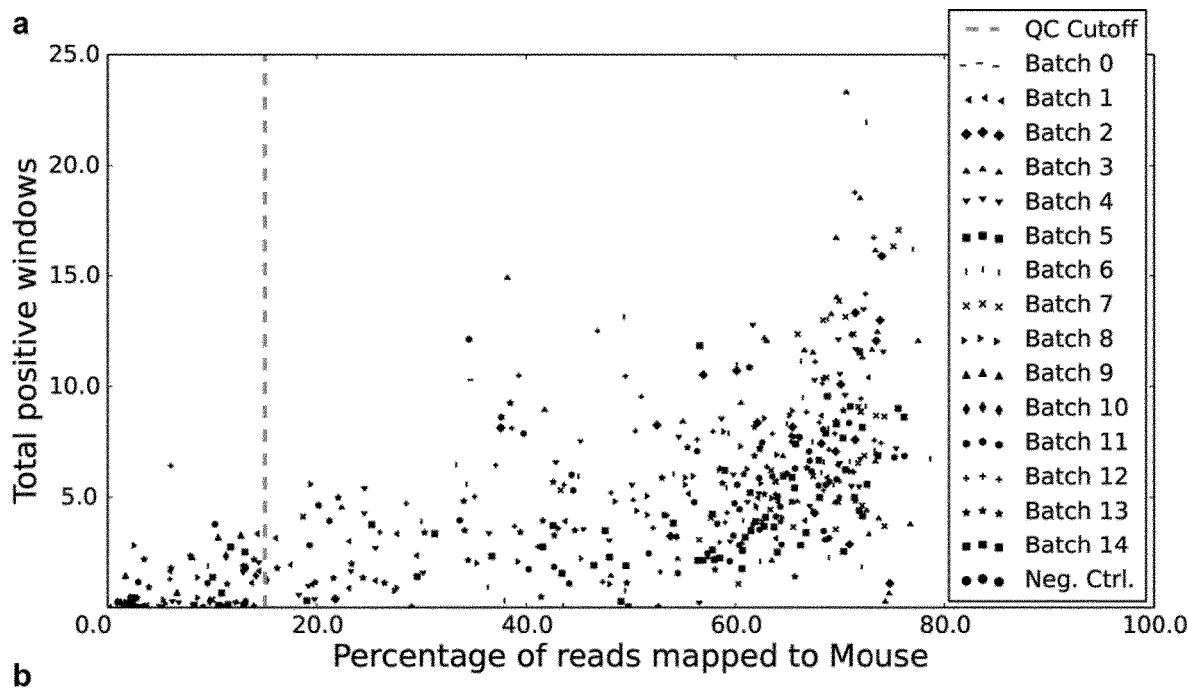
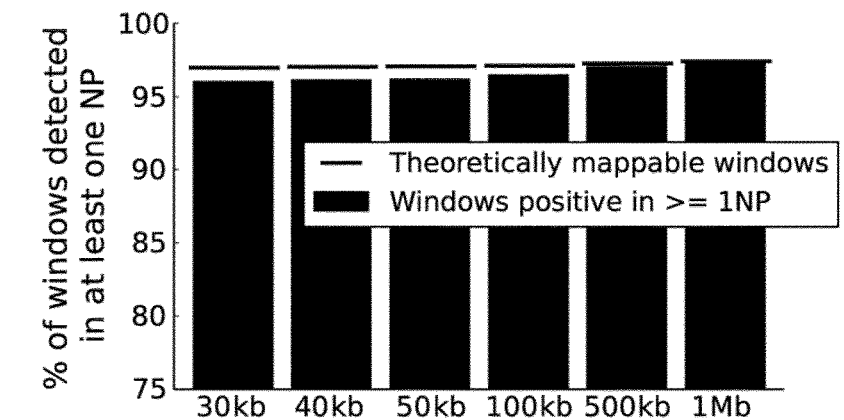
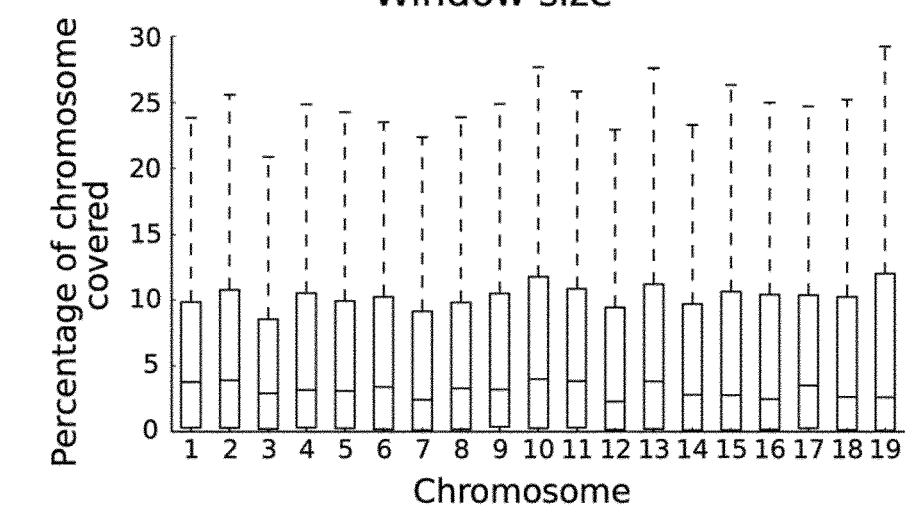

Fig. 7
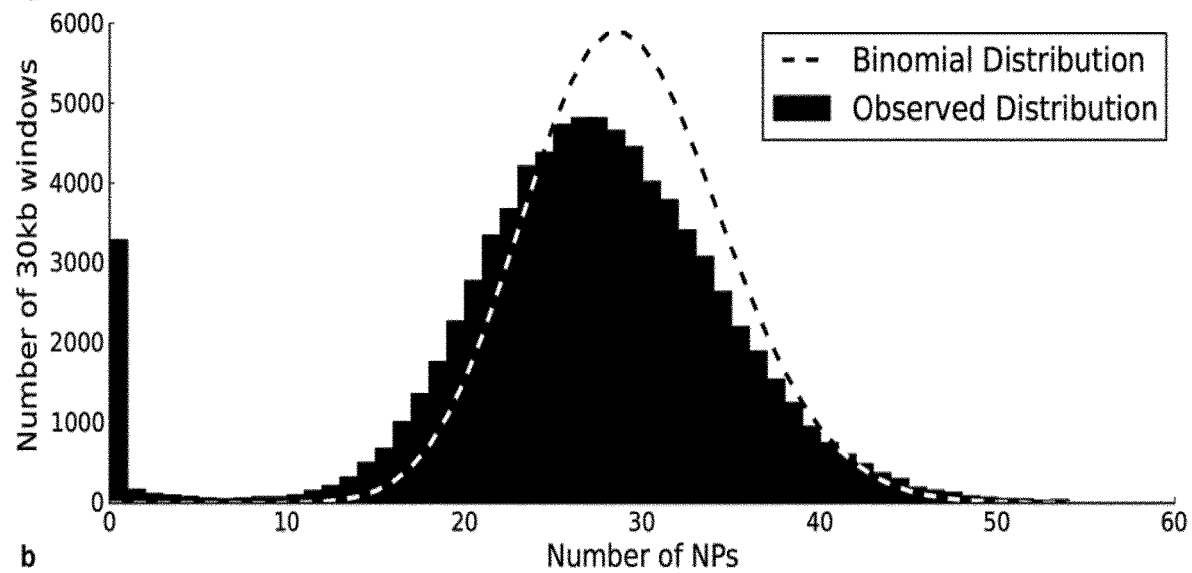
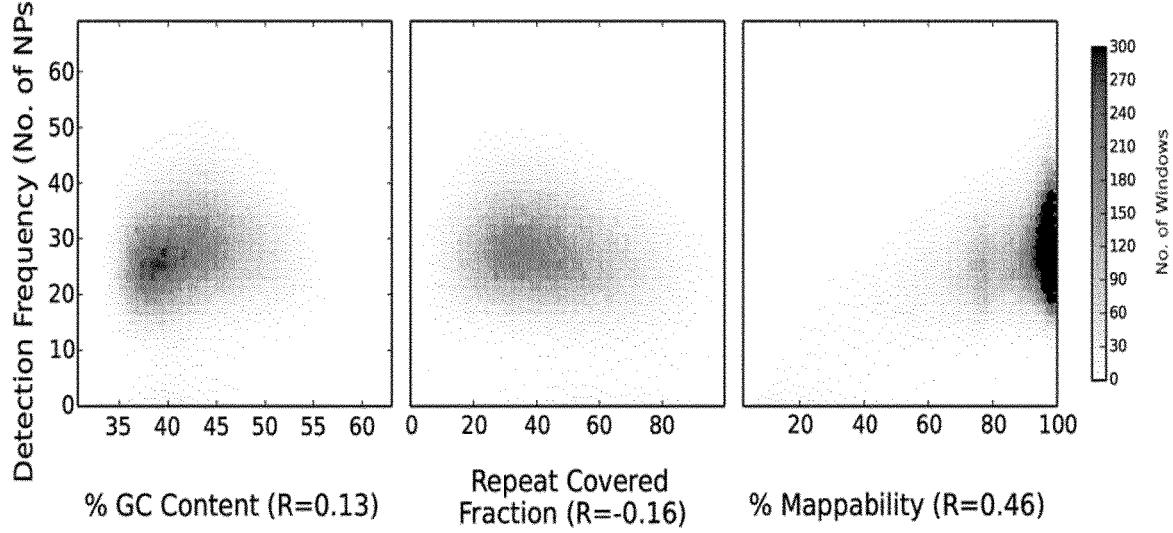
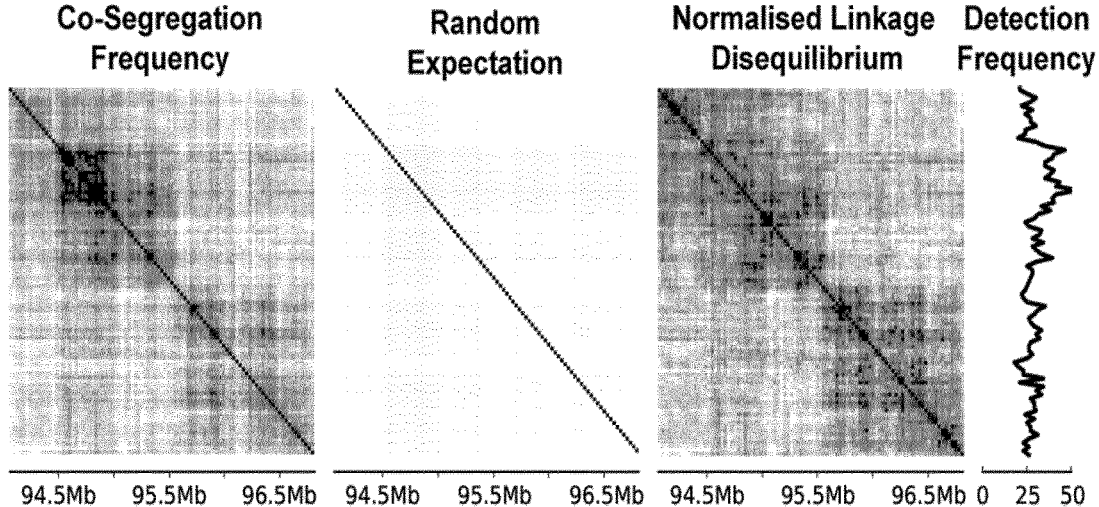

Fig. 11 a Statistical Inference of Co-segregation (SLICE) Model

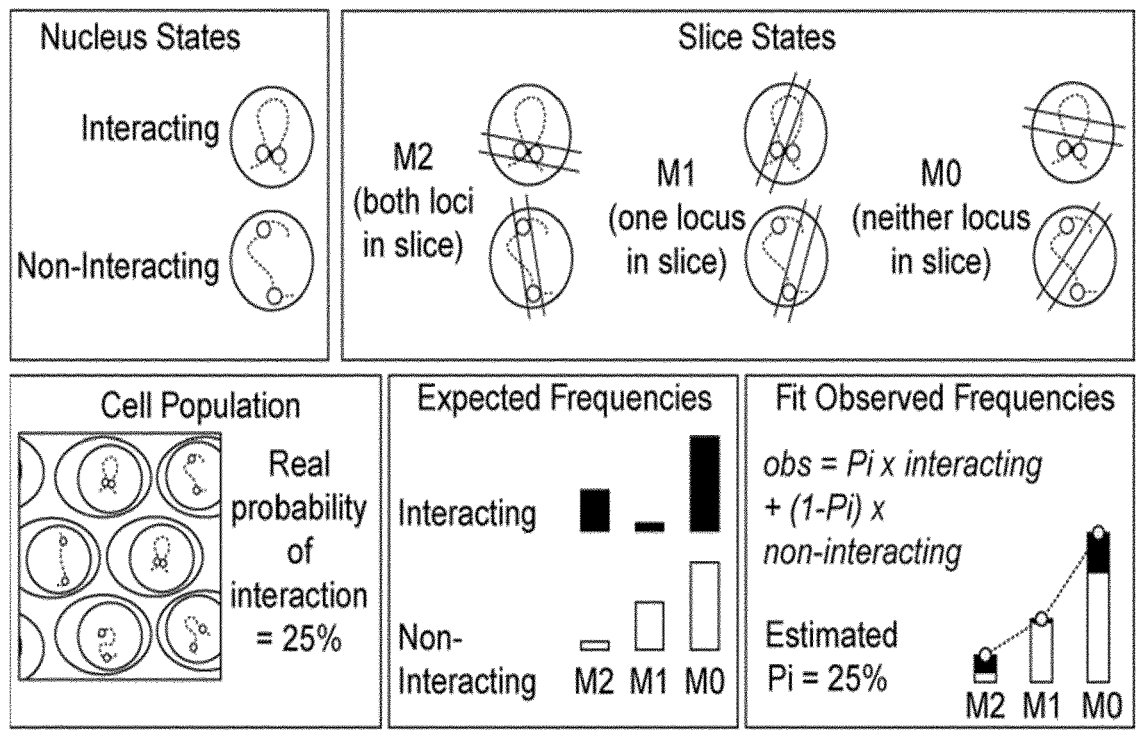

b

Co-segregation frequency of a locus pair:

$$u_2(z, \vec{d}) = \frac{\int_{V_{slice}(z)} \delta(\vec{x_1}-\vec{x_2}-\vec{d})\rho(\vec{x_1},\vec{x_2})d\vec{x_1}d\vec{x_2}}{\int_{V_{nucleus}} \delta(\vec{x_1}-\vec{x_2}-\vec{d})\rho(\vec{x_1},\vec{x_2})d\vec{x_1}d\vec{x_2}}$$

c Fraction of NPs with 2,1,0 loci

$$\begin{cases} M_0 = \langle t_0^2 \rangle P_2 + \langle t_0 u_0 \rangle P_1 + \langle u_0^2 \rangle P_0 \\ M_1 = 2\left[P_2 \langle 2t_1 t_0 + t_1^2 \rangle + P_1 \langle t_1 u_0 + t_0 u_1 + t_1 u_1 \rangle + P_0 \langle 2u_1 u_0 + u_1^2 \rangle\right] \\ M_2 = 1 - M_1 - M_0 \end{cases}$$

with $\begin{cases} P_2 = Pi^2 \\ P_1 = 2Pi(1-Pi) \\ P_0 = (1-Pi)^2 \end{cases}$ Fig. 14a
a Observation:
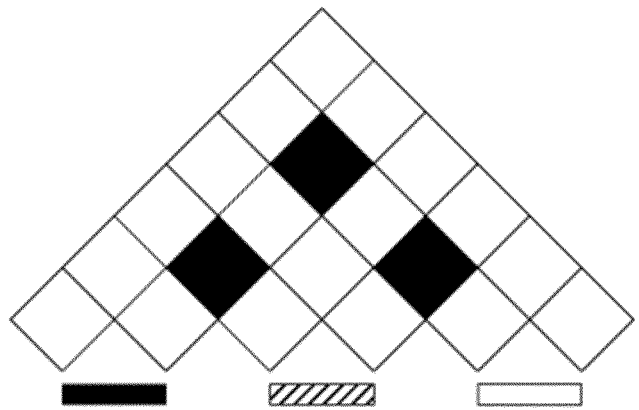
All possible pairwise contacts
observed between three regions
Possible Causes:
1: Simultaneous interaction
("true" triplets)
2: Separate interactions
("false" triplets)
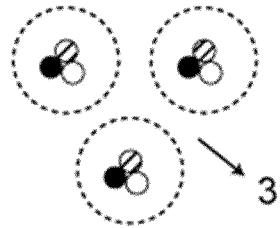 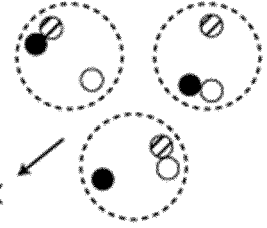
3: Complex mix
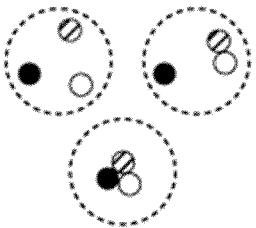

Fig. 14b b Strategy for identifying "true" triplets:

Select candidate TAD triplets sharing at least one significant pairwise interaction between their 40kb windows

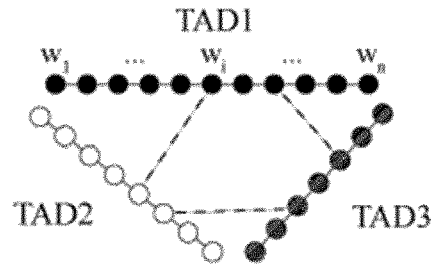

For each set of three TADs, calculate 3D co-segregation matrix for all 40kb windows

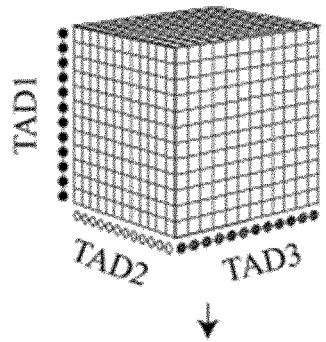

Compute mean Pi of all points in 3D matrix $$\overline{Pi}_{TADtriplet} = \frac{\sum_{w_i \in TAD1} \sum_{v_j \in TAD2} \sum_{u_k \in TAD3} Pi(w_i, v_j, u_k)}{n_{TAD1} \cdot n_{TAD2} \cdot n_{TAD3}}$$

Rank candidates by mean Pi. Select top 5% for analysis

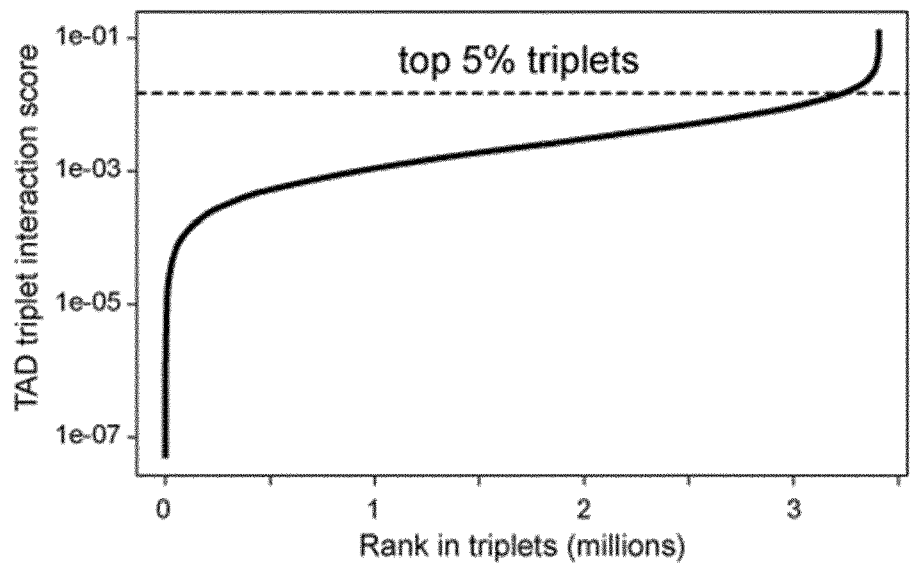

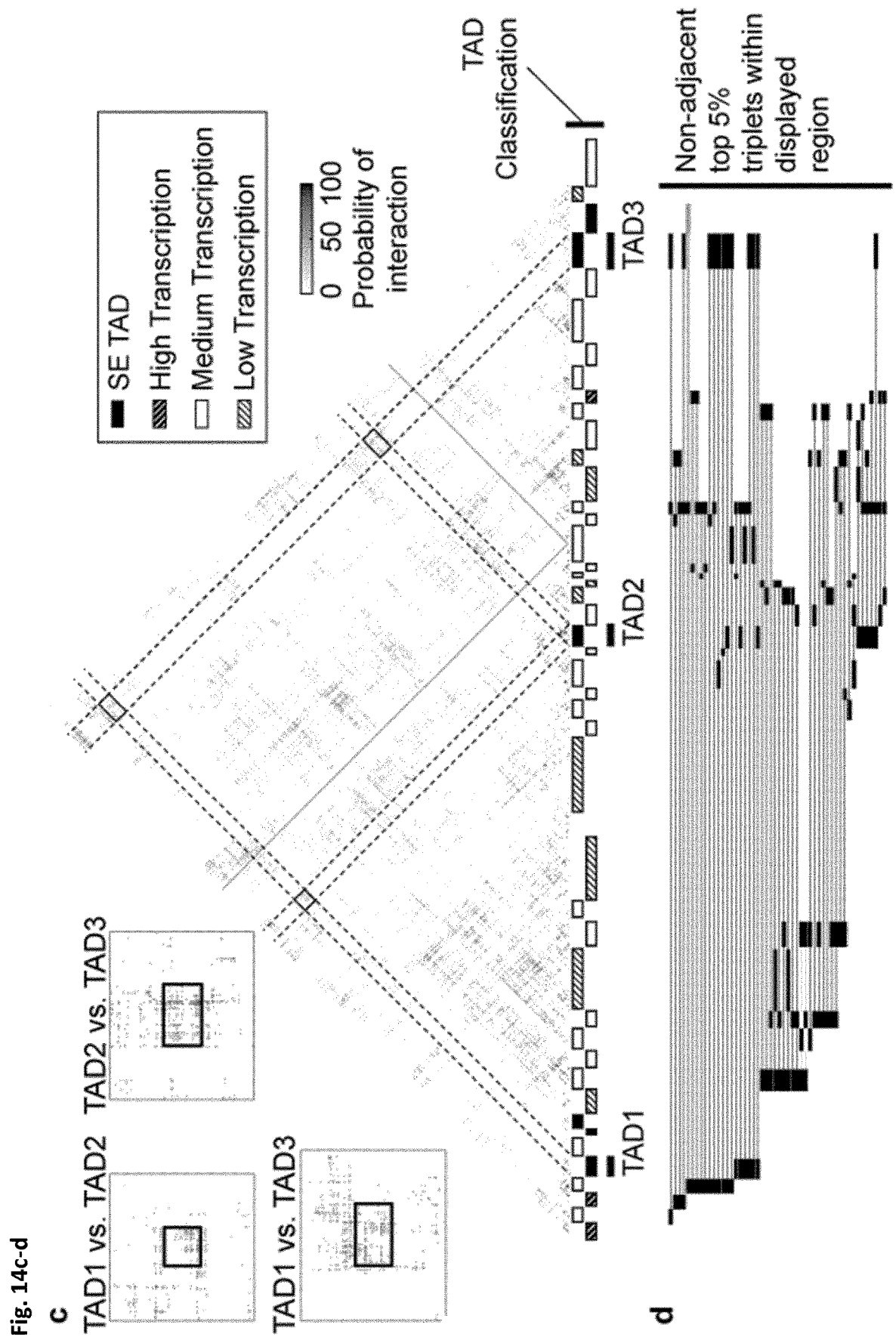
Fig. 14c-d

Fig. 14e-g
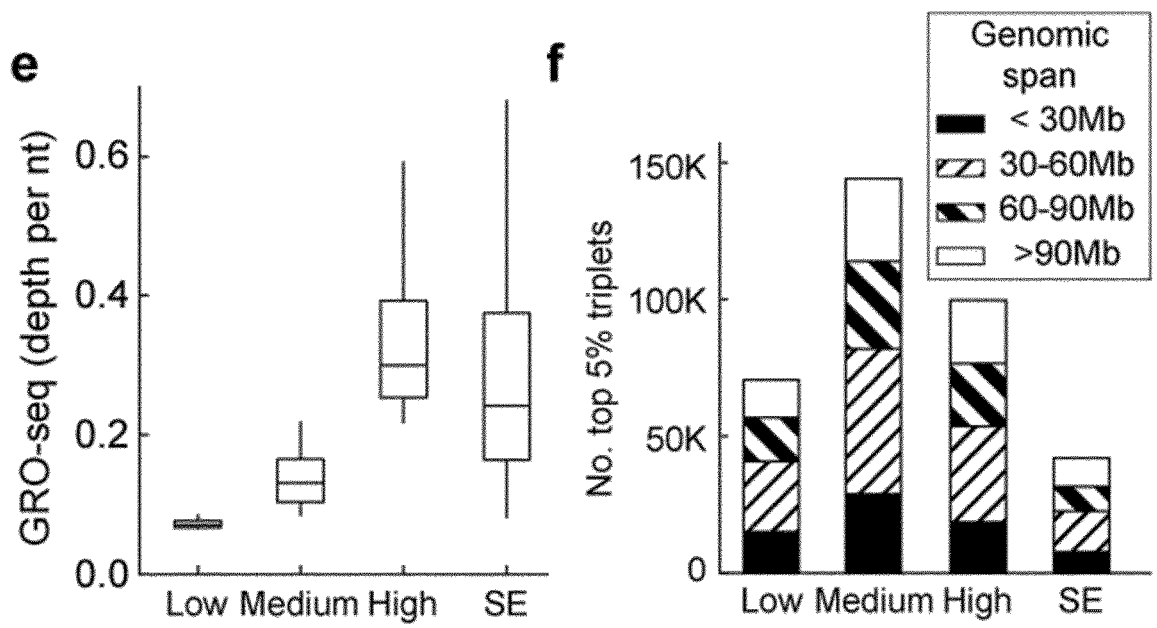
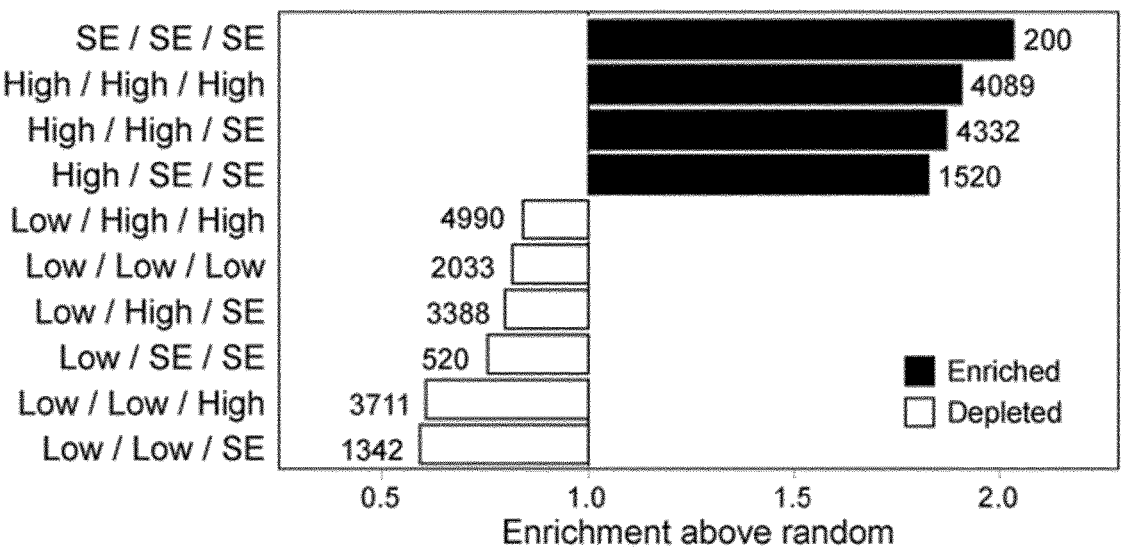

Fig. 14h-i
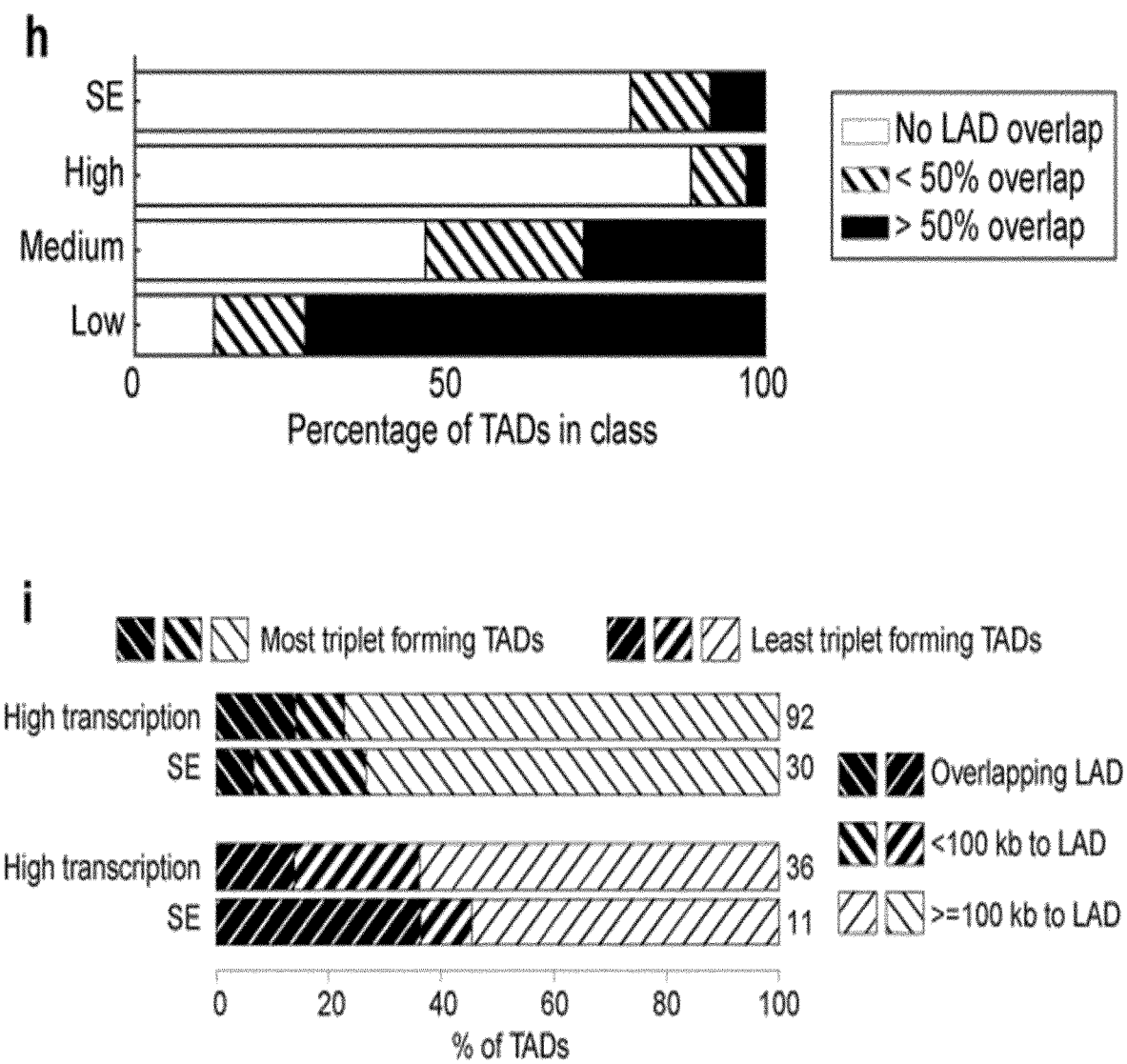

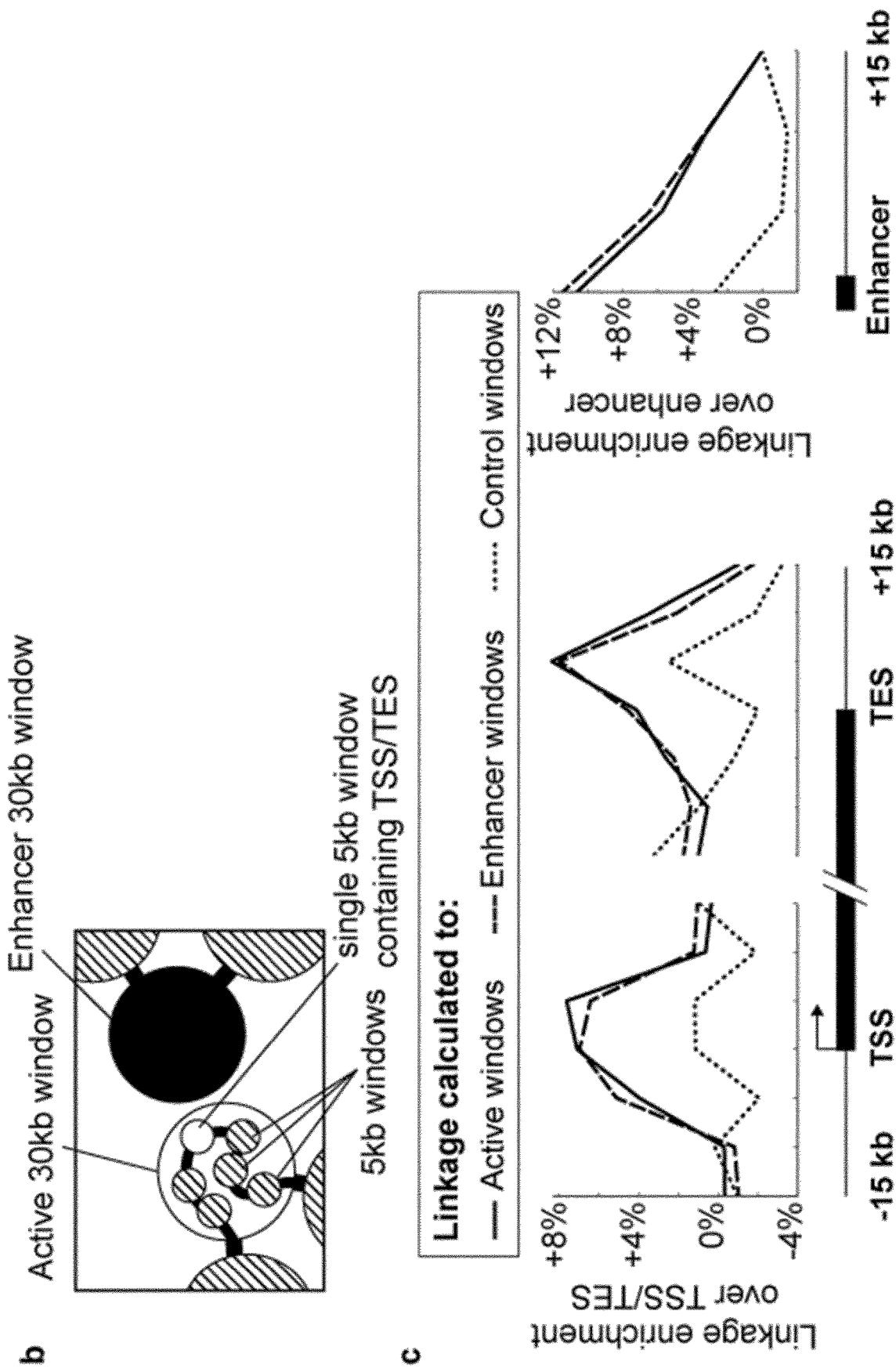
Fig. 15b-c

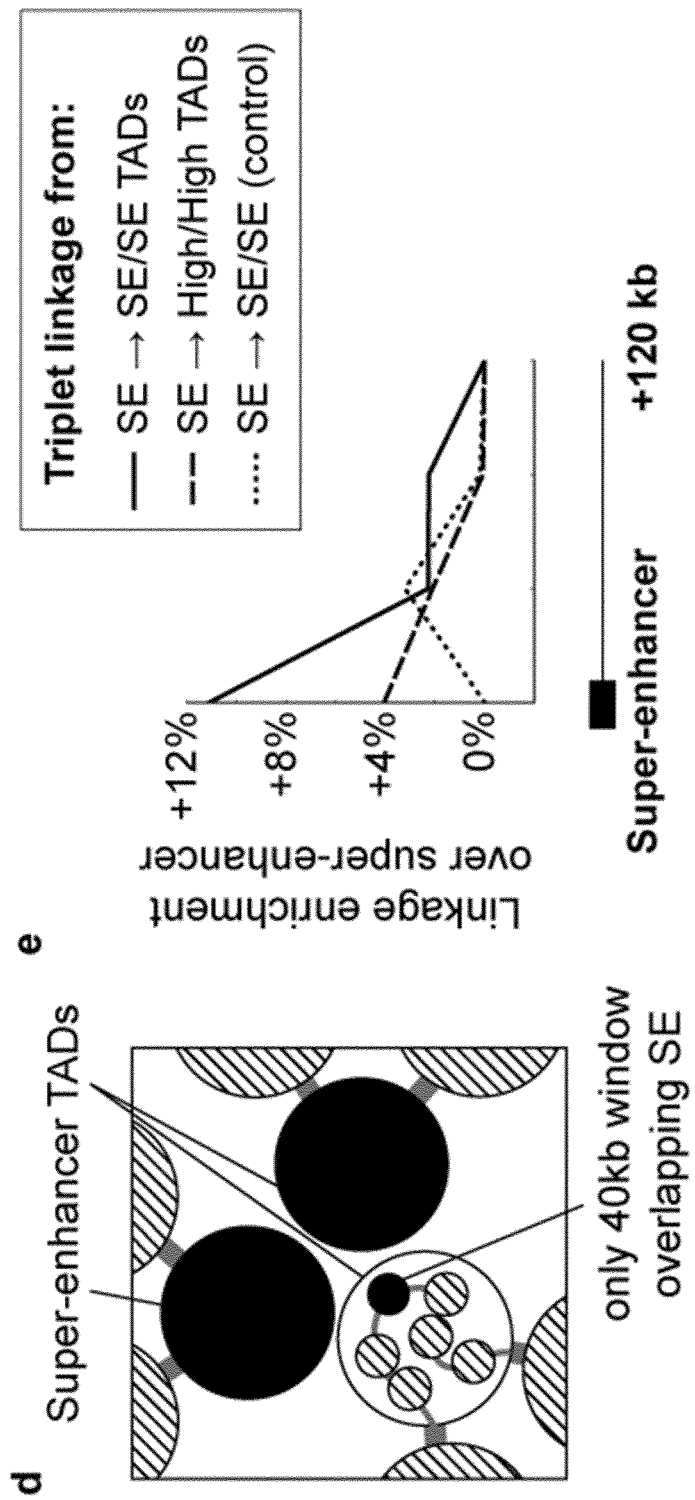
Fig. 15d-e

Fig. 16a-b
a
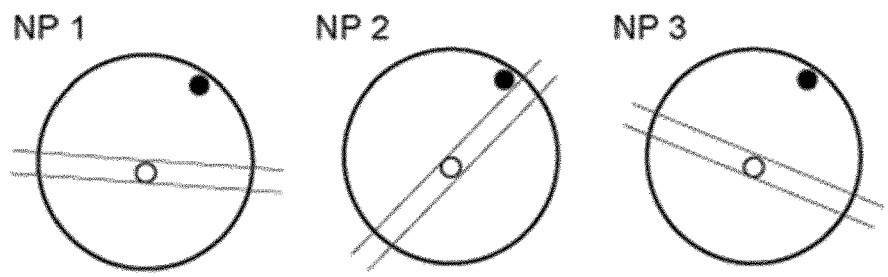
Avg. volume of NPs containing white locus = 13 μm³
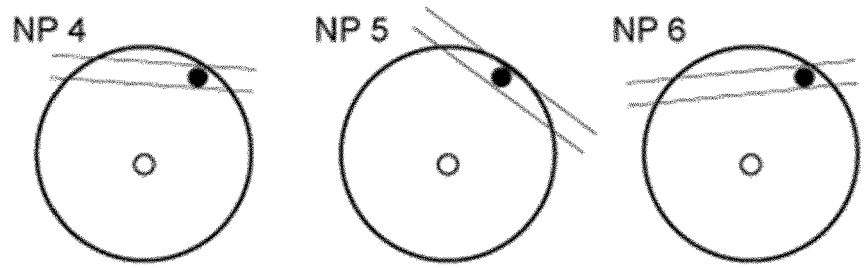
Avg. volume of NPs containing black locus = 4 μm³
b
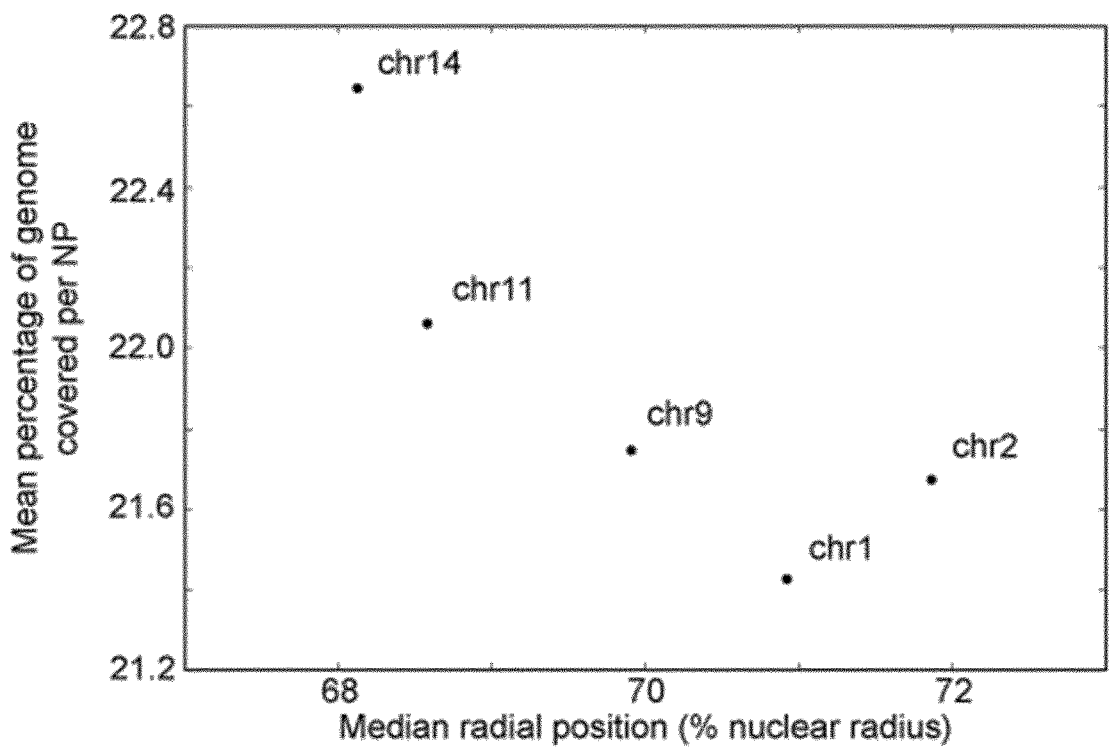

Fig. 16c-e
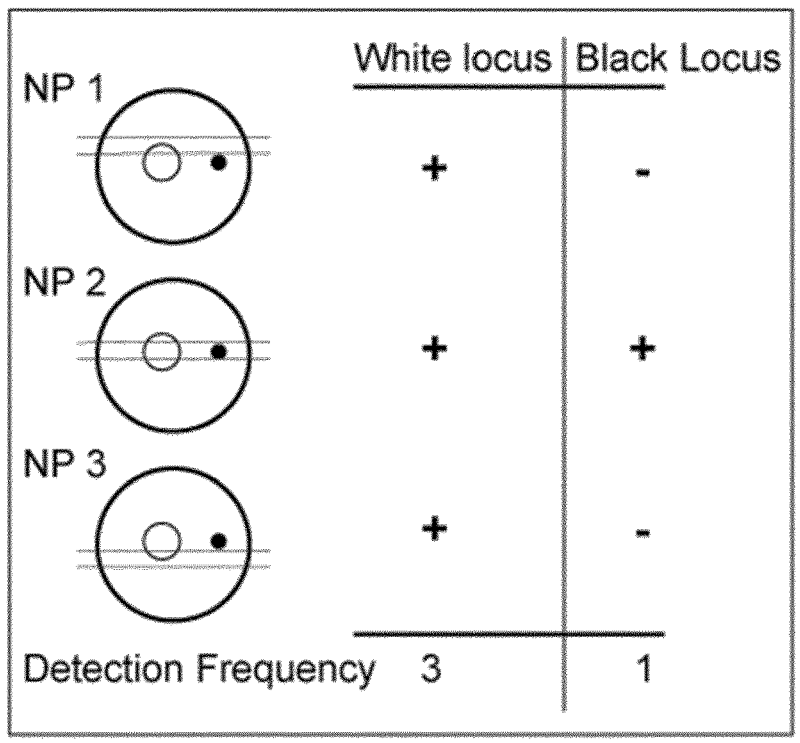
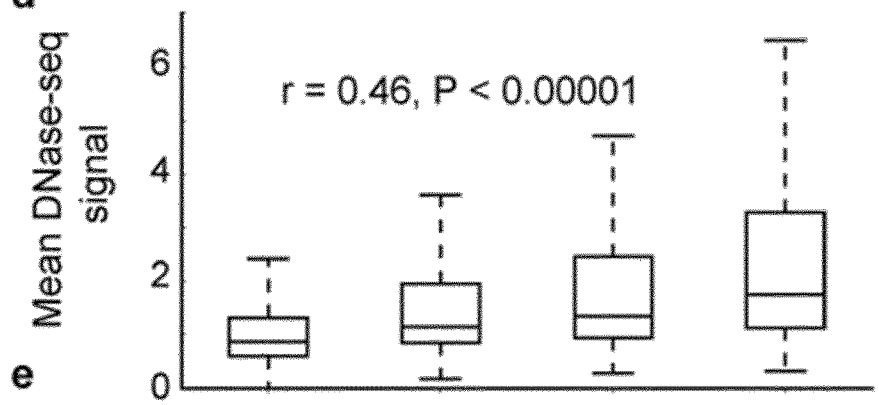
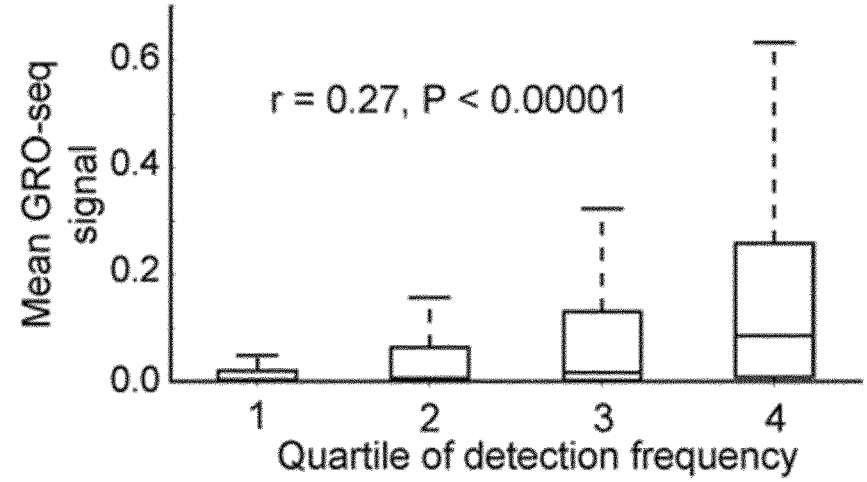

GENOME ARCHITECTURE MAPPING

The present invention relates to the field of analysis of the three-dimensional structure of the genome, i.e., for genome architecture mapping (GAM). The invention provides a method of determining spatial proximity of a plurality of nucleic acid loci in a compartment such as the cell nucleus, by exploiting their co-segregation amongst fractions of that compartment, identified upon separation of the nucleic acid loci from each other depending on their localization in the compartment to obtain a collection of fractions, e.g., by cryo-sectioning the compartment or, e.g. by cryomilling; determining the presence or absence of the plurality of loci in said fractions; and determining the co-segregation of said plurality of loci. Co-segregation may then be analysed with statistical methods to determine spatial proximity. The method can be used e.g., for determining physical distance between a plurality of loci; and mapping loci and/or genome architecture, e.g., in the nucleus; identification of regulatory regions directing expression of a specific gene through spatial contacts; identifying the nuclear position of an exogenous nucleic acid in the nucleus; determining chromatin compaction and/or diagnosing a disease associated with a disturbed co-segregation of loci.

Several approaches have been taken to analyse the structure of the genome and chromatin interactions. Linear genomic distances are often analysed by sequencing, for example shotgun sequencing. Problems with localizing sequences in the genome, in particular, in the case of repetitive sequences, can be approached, e.g., by HAPPY mapping[1], which measures linear genomic distances between loci based on the frequency of locus co-segregation after random fragmentation and dilution of genomic DNA, and which works for up to about 200 kb linear distance.

Information about the three-dimensional structure of chromatin is also of high interest, in particular, to discover contacts between regulatory regions and gene promoters. One example of chromosomal interactions influencing gene expression is a chromosomal region which can fold in order to bring an enhancer and associated transcription factors within close proximity of a gene. Studying the structural properties and spatial organization of chromosomes is important for the understanding and evaluation of the regulation of gene expression, DNA replication and repair, and recombination. The folding of chromosomes and their contacts has important implications for disease mechanisms and elucidation of targets for therapeutic approaches, e.g., in cancer or congenital diseases.

Chromatin exists in interacting and non-interacting states. Interacting states have different properties depending on the characteristics of the binding sites involved in the interactions, namely (a) their number, distance and distribution, (b) their specificity and affinity for binders, and (c) the concentration and specificity of binders. Chromatin interactions can also involve different numbers of loci associating simultaneously (multiplicity of interaction).

Fluorescence in situ hybridization (FISH) uses microscopy to directly measure spatial distances between genomic loci, but it can only be applied to the study of a small number of genomic regions at a time in the same nucleus (e.g., Pombo A. 2003. Cellular genomics: which genes are transcribed when and where? Trends Biochem. Sci. 28, 6). It is theoretically possible to re-probe the same cells or tissue sections with different sets of probes, but there are concerns that repeated re-probing causes structural artefacts, e.g. due to DNA denaturation necessary to dissociate subsequent sets of probes, that e.g. induce artificial aggregation (contacts) of loci (i.e. repositioning of subgenomic regions relative to each other and relative to nuclear landmarks, e.g. the nuclear lamina). In the case of metaphase chromosomes, which represent more condensed (and expectedly more stable) chromatin, the re-probing can be repeated for a maximum of six times (Pauciullo A et al. 2014, Development of a sequential multicolor-FISH approach with 13 chromosome-specific painting probes for the rapid identification of river buffalo (Bubalus bubalis, 2n=50) chromosomes. J Appl Genet. 55(3):397-401), but concerns about degradation of chromosome morphology can already be apparent after the second probing, which can lead to loss of chromosomes or nuclei (Heslop-Harrison J S, Harrison G E, Leitch I J (1992) Reprobing of DNA: DNA in situ hybridization preparations. Trends Genet 8: 372-373). RNA-FISH is a milder FISH approach that does not involve DNA denaturation but that can only be used to determine the nuclear position of actively transcribed genes (not silent genes). Samples from cells in the interphase stage of the cell cycle, where functional chromatin contacts are most often mapped, can be re-probed for RNA-FISH only about three times, although the preservation of structure has not been measured in detail. The number of probes which can be simultaneously applied in either DNA- or RNA-FISH is limited by distinguishable fluorescent markers, e.g. 181 barcodes can in principle be obtained by combining five colours, four colour ratios and two different levels of intensity (Pombo A. 2003. Cellular genomics: which genes are transcribed when and where? Trends Biochem. Sci. 28, 6). However, this approach (multiplexing fluorochromes) fails when the loci analysed are so close in space that the combination of fluorochromes in one probe is not distinguishable from the combination in another, and is therefore not amenable to the identification of loci that are spatially proximal. Furthermore, due to the need for a labelled probe for each specific locus, FISH can only be applied to analyse interactions of known loci of interest, and fails e.g. in the detection of endogenous or exogenous DNA sequences unless they are known a priori, e.g. viral subtype integration positions and the exact sequences of exogenous DNA. FISH is also confounded by a priori assumptions of linear genome organisation, which are not acceptable to study chromatin positioning features, e.g. chromatin contacts, when e.g. the influence of natural variation in genomic sequence in organism populations is of interest, e.g. in studying human samples, due to the fact that FISH does not inherently detect sequence variations such as copy number variations, or genomic rearrangements, without a priori probe design or a priori whole genome sequencing of the sample followed by probe design.

In a different approach, designated INGRID (IN-Gel Replication of Interacting DNA segments; Gavrilov, A. A. et al., 2014 Quantitative analysis of genomic element interactions by molecular colony technique. Nucl. Acids Res. 42 (5):e36), cross-linked chromatin fragments are spread out over large area of a polyacrylamide gel layer, followed by visualization of separate and associated elements in the form of, respectively, mono- and multicomponent molecular colonies generated during in-gel amplification of selected DNA fragments, which are visualised by molecular beacon technology (Chetverin A B, Chetverina H V. Molecular colony technique: a new tool for biomedical research and clinical practice. Prog. Nucleic Acid Res. Mol. Biol. 2008; 82:219-255). This technology also relies on a priori knowledge of genome organisation, and does not inherently discover DNA sequence variation, its spatial organisation and how it influences the spatial organisation of the whole genome.

Alternative current approaches to analysis of the three-dimensional structure of the genome are mainly based on chromosome conformation capture (3C) techniques, of which there are many current versions and adaptations (FIG. 4). 3C-based methods generally start with weak chemical crosslinking of proteins that mediate genomic contacts. After chromatin extraction, crosslinked pieces of DNA are treated with a restriction enzyme for DNA fragmentation. Addition of a ligase then connects (ligates) two pieces of DNA. Different variants of 3C use different methods of detecting such ligation events: a popular one is sequencing (Hi-C, 4C-seq).

Figure 4:
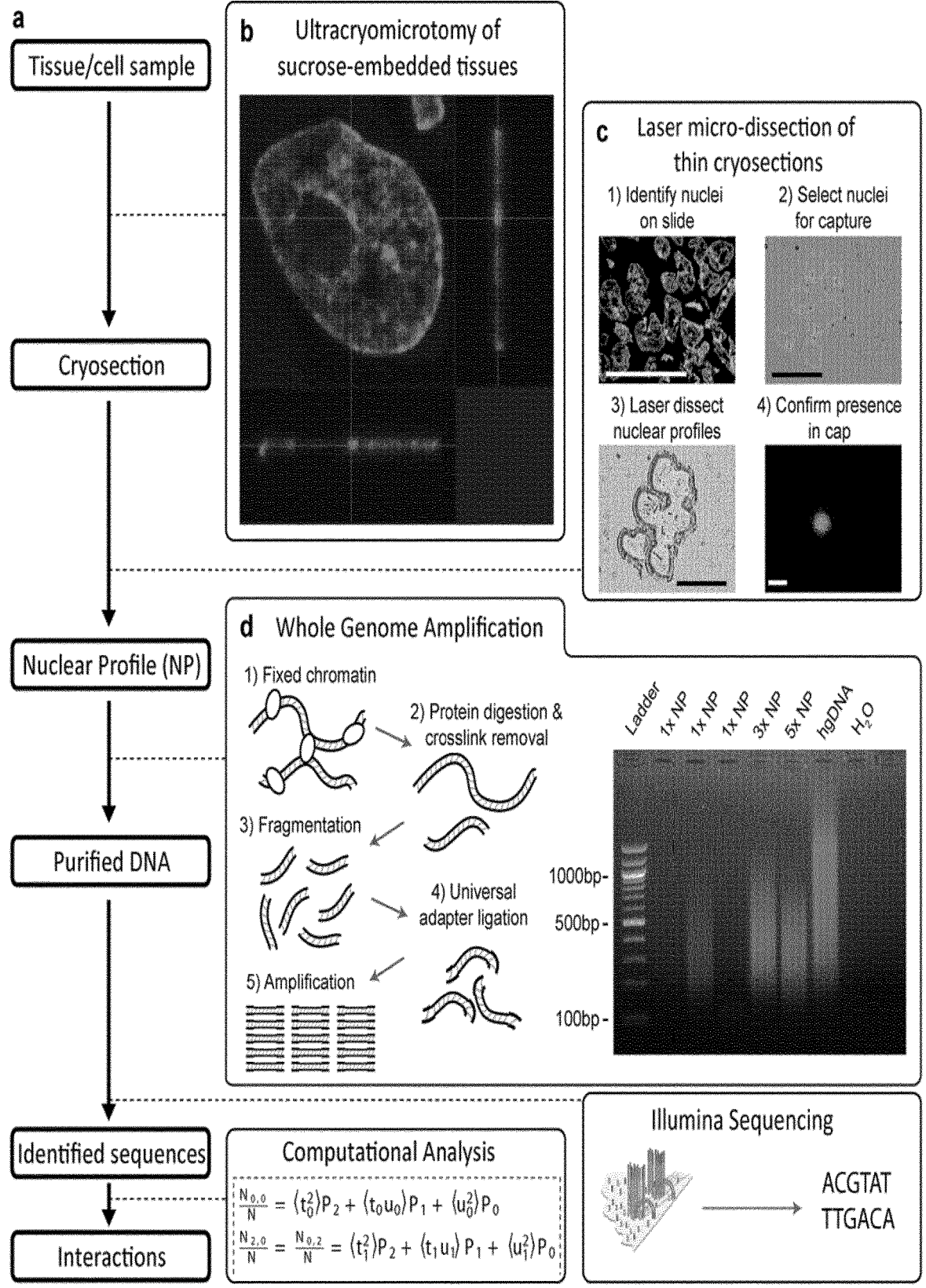

Limitations of these technologies are described in FIG. 4 and have been discussed in the literature (e.g., in Belmont A. S., 2014. Large scale chromatin organization: the good, the surprising, and the still perplexing. Curr Op Cell Biol 26, 69; O'Sullivan J. M. et al., 2013. The statistical-mechanics of chromosome conformation capture. Nucleus 4, 390; Williamson, I. et al. 2014. Spatial genome organization: contrasting views from chromosome conformation capture and fluorescence in situ hybridization. Genes Dev. 28, 2778-2791.).

At present, it is not possible to identify binding sites genome wide in an unbiased manner, and as a result we fail to understand which nuclear components establish different aspects of chromosome architecture, and how long-range chromatin contacts help maintain genome stability and influence genome function (e.g. gene expression). Therefore, the identification of binding sites and measurement of the frequency with which binding sites interact with each other are major current challenges.

The present inventors addressed the problem of providing an improved method for determining the spatial proximity of nucleic acids, which avoids bias based on ligation of fragmented nucleic acids for detection of nucleic acids interactions, and which allows for simultaneous analysis of several high multiplicity interactions (each involving more than two loci), in particular, more than two interactions, and in one embodiment, for simultaneous analysis of substantially all nucleic acid interactions in the genome and their interdependencies. This problem is solved by the method of the invention, as described below and in the claims. This method is designated Genome Architecture Mapping (GAM).

The present invention provides a method of determining spatial proximity of a plurality of nucleic acid loci in a compartment, comprising steps of
(a) separating nucleic acids from each other depending on their localization in the compartment to obtain a collection of fractions;
(b) determining the presence or absence of the plurality of loci in said fractions; and
(c) determining the co-segregation of said plurality of loci.

A locus (plural loci) is the specific location of a gene, DNA sequence, or position on a chromosome (Wikipedia). Each chromosome carries many genes; the number of protein coding genes in the haploid human genome is estimated to be 20,000-25,000, on the 23 different chromosomes. A variant of the similar DNA sequence located at a given locus is called an allele. In the context of the invention, the nucleic acid may be DNA or RNA or a combination of both, e.g., if interactions between genes being actively transcribed and other genomic regions are to be analysed. Usually, co-segregation of DNA is analysed with the method of the invention. The co-segregation of loci may be analysed in any cellular or organ compartment comprising nucleic acids, such as the nucleus of a eukaryotic cell, a mitochondrion or a prokaryotic cell. Normally, co-segregation of nucleic acid, in particular, DNA, loci in the nucleus of a eukaryotic cell will be analysed. The method of the invention thus constitutes a solution to analyse locus proximity in the nucleus, through measuring their frequency of co-segregation in fractionated nuclei.

The cell from which the compartment is derived may be a bacterium, a protozoan, a plant cell, a fungal cell or an animal cell, e.g., a mammalian cell, such as a cell from a patient (preferably, a human patient) having a disease or a disorder, or being diagnosed for a disorder, or a healthy subject. The cell may be, e.g., a tumor cell or a stem cell, such as an induced pluripotent stem cell generated, e.g., through reprogramming of human tissues. Such cells can advantageously be used to apply GAM to study human developmental disorders or congenital disease. If the cell is an embryonic stem cell, it is preferably not generated in a method involving destruction of a human embryo.

The mammal preferably is a human, but it may also be of interest to investigate, and, optionally, compare the genomic architecture of other organisms, such as $E.$ $coli$, yeast, $A.$ $thaliana$, $C.$ $elegans$, $X$ $laevis$, $D.$ $rerio$, $D.$ $melanogaster$, mouse, rat or primate.

Cells can be derived from cell culture or analysed ex vivo from a specific tissue from a living organism or a dead organism, i.e., post-mortem, or from a whole experimental organism (e.g. a whole $D.$ $melanogaster$ embryo or $C.$ $elegans$). Cells used in the analysis are preferably selected, e.g., to share a common stage in the cell cycle, or to analyse only cells belonging to a specific developmental lineage or cell type (e.g. within a biopsy of a human organ). For example, in the pancreas, only the insulin producing β-cells may be analysed. This approach is preferable to synchronizing the cells in a particular stage of the cell cycle, or sorting the cells e.g. by fluorescence activated cell sorting to capture a particular cell type, as (a) these approaches can alter the arrangement of nucleic acids in the compartment of interest prior to their measurement, and (b) they produce only small numbers of cells (e.g. from size-limited biopsies), which may lead to problems with downstream analyses. Synchronized cells or cells sorted by e.g. by fluorescence activated cell sorting can also be used in the invention. A marker can be used to help with cell type selection, e.g., an antibody specific for a protein uniquely expressed in the cell type or cell stage of interest, or detected by in situ hybridization e.g. with a nucleic acid probe that detects a specific e.g. mRNA, or other RNA, expressed specifically in the cell type of interest, or a fluorescent marker such as GFP showing expression of a specific gene or characteristic of a specific stage. For example, a GFP transgene under the control of the promoter of the Pitx3 transcription factor can be used to mark dopamine-expressing neurons (Maxwell et al., 2005, Pitx3 regulates tyrosine hydroxylase expression in the substantia nigra and identifies a subgroup of mesencephalic dopaminergic progenitor neurons during mouse development, Dev. Biol., 282 (2): 467-479). Cells can be pre-treated with an agent, e.g., to test the effect of drugs on co-segregation or positioning of loci.

Nuclei, cells, tissues or whole organisms are preferably treated with a crosslinking agent before step (a) is carried out. Preferably the crosslinking agent may comprise formaldehyde or another stabilizing agent compatible with DNA extraction. Formaldehyde will preferably be used, at a concentration of 0.5-8%, preferably, 1-8%, 2-8% or, most preferably, 4-8% (all w/w), e.g., in a buffered solution of 250 mM HEPES-NaOH pH 7.0-8.0, preferably for mammalian cells at pH 7.6-7.8, for 10 min to 24 h, preferably for 10 min at 4% followed by 2 h at 8%. For example, in the case of experimental organisms, whole tissues can be crosslinked by perfusion with HEPES-buffered formaldehyde solution (e.g., 4%), preferably for at least 30 min, followed by tissue dissection in ice-cold 4% formaldehyde in 250 mM HEPES-NaOH pH 7.6 for 30 min to 1 h, followed by ice-cold 8% formaldehyde in 250 mM HEPES-NaOH pH 7.6 for 1-3 h (Möller et al., 2012, Proteomic analysis of mitotic RNA polymerase II complexes reveals novel interactors and association with proteins dysfunctional in disease. Mol. Cell. Proteomics 11(6):M111.011767).

In the case of cells in suspension (e.g. human white blood cells, Drosophila S2 cells, or other isolated cells in suspension), cells are sedimented by centrifugation (e.g. 150-300×g for mammalian cells), before the cell sediment (pellet) is resuspended, e.g. in 4% formaldehyde in 250 mM HEPES-NaOH pH 7.6. Cells are sedimented by centrifugation (e.g. 150-300×g for mammalian cells), the supernatant decanted, before adding 8% formaldehyde in 250 mM HEPES-NaOH pH 7.6, without disturbing the cell pellet thereafter. The cell pellet is allowed to crosslink for, e.g. 1 h. The cell pellet is progressively compacted by centrifugation at increased centrifugational force (in steps as e.g. 500×g, 1000×g, 2000×g, 4000×g, 8000×g, and in some cell types up to 10000×g; each 2 min, last step 5-10 min). Total time in 8% concentrated fixative, as stated above, is up to 24 h, preferably about 2 h. For transport (e.g. between a clinic and a diagnostics laboratory), or for short-term storage (1 h to 1 week), the 8% formaldehyde supernatant is removed in the last centrifugation, and substituted for 1% formaldehyde in 250 mM HEPES-NaOH pH 7.6, without disturbing the cell pellet. Longer storage periods are not recommended, although they are possible by replenishing with fresh formaldehyde (e.g. 1% formaldehyde in 250 mM HEPES-NaOH pH 7.6). For fixation of cells grown attached to a surface (e.g. human skin fibroblasts, human muscle cells), the cell culture media is decanted, before rinsing with e.g. 4% formaldehyde in 250 mM HEPES-NaOH pH 7.6, followed by fresh addition of e.g. 4% formaldehyde in 250 mM HEPES-NaOH pH 7.6, and incubation, e.g. for 10 min. Fixative is decanted and substituted for e.g. 8% formaldehyde in 250 mM HEPES-NaOH pH 7.6. After preferably 1 h, the cells are gently scraped and collected in a tube. After centrifugation at 150-300×g, the cell pellets are compacted by centrifugation at increased force, as above for suspension cells. For transportation or short-term storage, fixed cells or tissues can be stored, e.g. in 1% formaldehyde in 250 mM HEPES-NaOH pH 7.6, ideally frequently substituted for fresh solution, e.g. every day or every other day. Storage in the absence of fixative, or without replenishment in fresh fixative, can lead to structural deterioration of nucleic acid position or quality due to reversal of formaldehyde cross-links.

The crosslinking agent induces linkage of proteins with each other and between nucleic acids and proteins. The method of the invention allows for the use of stronger cross-linking conditions than are compatible with current 3C-based methods, and therefore better preservation of the nuclear structure. It was surprising to the inventors that sequencing of nucleic acids was still possible after the nucleic acids were subjected to the cross-linking step which is compatible with optimal structural preservation of subcellular structure. The method is also theoretically possible without a crosslinking step, as fractionation of nuclei is possible through sectioning of vitrified cells (e.g. as discussed in Dubochet et al., 1988. Cryo-electron microscopy of vitrified specimens. Q. Rev. Biophys. 21: 129) or through cryomilling of vitrified cells (Oeffinger M, Wei K E, Rogers R, DeGrasse J A, Chait B T, Aitchison J D, Rout M P, 2007 Comprehensive analysis of diverse ribonucleoprotein complexes. Nat Methods. 4, 951-6; Hakhverdyan et al. 2015. Rapid, optimized interactomic screening. Nature Methods 12, 553). In either case, the use of vitrification (i.e. rapid freezing) to preserve cellular ultrastructure would avoid any artefacts that may potentially be introduced by the application of chemical crosslinking agents (e.g. formaldehyde). For example, treatment with chemical crosslinking agents e.g. formaldehyde could lead to repositioning of subgenomic regions relative to each other and/or relative to nuclear landmarks, e.g. the nuclear lamina, whilst this potential for repositioning would not occur in vitrified samples. Such cell or tissue samples structurally preserved using vitrification cannot be assayed by either 3C-based methods or FISH methods.

The separation of nucleic acids from each other, depending on their localization in the compartment, to obtain a plurality of fractions in step (a) is carried out by sectioning the compartment, preferably, by ultracryosectioning the compartment. The method of the invention involving sectioning is also designated sGAM. Alternatively, the separation can be carried out through cryomilling (Oeffinger M, Wei K E, Rogers R, DeGrasse J A, Chait B T, Aitchison J D, Rout M P, 2007 Comprehensive analysis of diverse ribonucleoprotein complexes. Nat Methods. 4, 951-6; Hakhverdyan et al. 2015. Rapid, optimized interactomic screening. Nature Methods 12, 553).

The nuclear cryosections are produced in the absence of resin-embedding, e.g., by the Tokuyasu method (Tokuyasu, K. T., 1973, J. Cell Biol. 57, 551-65, A technique for ultracryotomy of cell suspensions and tissues.), which involves cryoprotection of fixed tissues using embedding in a saturated sucrose solution for at least about 30 min, or at least about 2 h, or at least about 1 day, or up to 1 week, at a temperature of 0° C.-25° C., preferably, at room temperature (20-25° C.) or at about 4° C., e.g., for 2 h at room temperature, or for 2 h at room temperature followed for short term storage for 1 day up to a week at about 4° C. Embedding is followed by placing the sucrose-embedded cell pellet or tissue, or organism, e.g. on a metal stub which acts as a sample holder, before freezing in liquid nitrogen, and sectioning preferably at −80 to −110° C., depending on the tissue, e.g., about −100° C. Slightly modified methods (Guillot P V, Xie S Q, Hollinshead M, Pombo A (2004) Fixation-induced redistribution of hyperphosphorylated RNA polymerase II in the nucleus of human cells. Exp. Cell Res. 295, 460-468; Pombo A, Hollinshead M, Cook P R (1999) Bridging the resolution gap: Imaging the same transcription factories in cryosections by light and electron microscopy. J. Histochem. Cytochem. 47, 471-480) have been shown to provide good results. These methods preserve cellular architecture comparable to that observed in unfixed cryosections, and provide optimal preservation of active RNA polymerases and nuclear architecture. The method of Chen et al., 2014, Small 10:3267, can alternatively be used. Unfixed sections may, e.g., be prepared according to methods described by Lučič V., et al., 2013. J. Cell Biol. 202 (3), 407.

Sections, e.g., of a nucleus, can have a thickness of about 70 nm to about 1000 nm, preferably, 150-220 nm or 180-200 nm for a nucleus 5-15 micrometer in diameter. The inventors for example cryosectioned mouse embryonic stem (ES) cells (mESCs; which have 9 μm diameter nuclei) at a thickness of 220 nm according to established protocols[3] (FIG. 5a,b). Commercial equipment for cryosectioning in a sucrose medium for fixed cells is available (e.g., Leica UltraCut UCT 52 ultracryomicrotome).

Sectioning leads to a collection of fractions, i.e. a plurality of fractions. The optimal thickness of sections depends on the size of the compartment, which is, in step (a), preferably separated into 5-300 fractions, 10-100 fractions, more preferably, 40-60 fractions or about 45-50 fractions, which, as explained in detail below, has been found to be appropriate for a mouse or human cell nucleus (or a nucleus having a similar size). The thickness of the fractions should be homogenous for the whole analysis.

In one embodiment of the invention, all sections of a compartment, in particular, of one nucleus, are analysed in the method of the invention, rendering an analysis of the genome architecture of a single cell possible. However, this is not required, and the analysed fractions may be sampled from a plurality of compartments, e.g., a plurality of nuclei, across the population of cells of interest. Using the method of the invention, preferably, more than 180 fractions are analysed, e.g., about 180 to about 10000 fractions, preferably, about 200 to 5000, about 220 to 4000, about 230-3500, about 250-3000, 300-2000 or 500-1000 fractions may be analysed, wherein these fractions may be obtained from a plurality of cells (or nucleic acid containing cellular compartments).

Single nuclear profiles (NPs) are isolated from the sections, e.g., by laser microdissection[4] (FIG. 5c).

In step (b), the presence or absence of the plurality of loci may be determined by a non-microscopical method, e.g., by sequencing, preferably, by next generation sequencing. For example, single cell whole genome amplification (WGA) may be used. Preferably, the nucleic acids of loci in the fraction are sequenced substantially or completely. This is of particular interest if the method is carried out to detect possible interactions between different loci in a research setting, and a "normal" co-segregation pattern has not yet been established for the cell type of interest in the physiological conditions used. The method of the invention may thus be used to analyse spatial proximity (and, consequently, interactions) of unknown and/or unspecified loci.

For example, nucleic acids such as DNA, may be extracted from the fractions (e.g., from single nuclear profiles), fragmented and amplified using single-cell whole genome amplification (WGA)[5] (FIG. 5d). WGA-amplified DNA may be sequenced, e.g., using Illumina HISEQ technology. Visual inspection of tracks from single NPs shows that each contains a different complement of sub-chromosomal regions (FIG. 2a), as expected from chromatin passing in and out of a thin nuclear slice. Furthermore, each NP contains only a restricted subset of chromosomes.

However, there may be situations where the presence or absence of a specific interaction (co-segregation) has previously been investigated, so the interacting loci of interest are already known. In particular in diagnostic settings, a significant difference in interacting loci may have been found between different patient groups (e.g., healthy subjects and subjects having a disease such as a tumor or a congenital disease). In such situations, presence or absence of the two (or more) loci of interest can also be determined by specific PCR, or by otherwise specifically checking for their presence, e.g., by Southern blot or by Illumina HISEQ technology, after selection of nucleic acids covering locus of interest, e.g. via IDT target capture for next generation sequencing (IDT, Coralville, Iowa, USA).

sGAM thus preferably combines ultracryosectioning with DNA detection (e.g. by whole genome amplification and next generation sequencing). When thin cryosections are cut through individual nuclei, loci that are closer to each other in the nuclear space (but not necessarily on the linear genome) are found together in the same section more often than distant loci (i.e. they co-segregate more frequently, FIG. 1b). The nuclear distance between genomic loci can then be inferred by scoring the presence or absence of loci among a number of sections through individual nuclei (FIG. 1c). The resulting table can be used to compute the co-segregation frequency of each locus against every other locus (FIG. 1d) to create a matrix of inferred relative distances between loci. Therefore GAM allows for the calculation of chromatin contacts genome wide.

Co-segregation may be analysed with a statistical method to determine spatial proximity (e.g. Weibel, E. R., 1979. Stereological Methods: Practical Methods for Biological Morphometry. Vol. 1 Academic Press, London, UK; Weibel, E. R., 1980. Stereological Methods: Theoretical Foundations. Vol. 2. Academic Press, London, UK). Close spatial proximity can be a sign for specific interaction of loci. Specific interaction of loci may thus also be determined by analysing co-segregation with a statistical method. Statistical methods used in the method of the invention may be, e.g., inferential statistic methods. Statistical methods used in the examples may also be used in the method of the invention to analyse samples of different origin and/or for different loci of interest, e.g., as mentioned herein.

Preferably, the loci are determined to be proximal to each other, or to interact specifically, when they co-segregate at a frequency higher than expected from their linear genomic distance on a chromosome. Statistical methods can also differentiate between a specific interaction and a general condensation of chromatin and/or a reduction in nuclear volume, e.g., in a diagnostic setting. GAM may be used to determine relative distances. Absolute distances can be calculated by relating the relative distance to the size of the nucleus. GAM may be used to assess the radial position of loci of interest in the compartment of interest, e.g. in a spherical compartment, sectioning yields equatorial sections with larger variety of DNA loci, and apical sections with lower variety of DNA loci, hence the radial position of the locus in the spherical compartment can be inferred from the complexity of DNA loci in the sections where it is detected. Alterations in radial positioning of DNA loci are associated with e.g. human disease (e.g. Maeburn K. J. et al. 2009 Disease-specific gene repositioning in breast cancer. J. Cell Biol. 187(6):801-12; Kubben N. et al. 2012. Mapping of lamin A- and progerin-interacting genome regions. Chromosoma 121(5): 447-64). If all possible pairs of loci in the genome at a given genomic (linear) distance are considered, and their nuclear (3D) distance measured, pairs of loci that do NOT interact will be found distributed around an average 3D distance that depends on the genomic distance between the two loci and the degree of chromatin compaction. In contrast, interacting pairs will be found closer together more often than the average for that genomic distance in the nucleus of that particular cell type. More complex arguments can also be considered (see below), but an interaction can be most simply defined as a deviation from the random arrangement of the chromatin fibre taking into consideration any additional contributing factor to a non-random behaviour.

GAM measures the frequency with which two loci co-segregate in the same nuclear profile, and can measure the co-segregation of all genomic loci simultaneously, producing quantitative information that is amenable to (a) the identification of genomic coordinates that more frequently interact with other genomic regions, but also (b) to a wide-range of mathematical treatments that calculate the probability of loci interacting above some random (expected) behaviour.

Genome-wide maps of co-segregation of loci arise from specific physical interactions as well as random contacts, which are heavily dependent on the linear genomic distance between loci, and also affect co-segregation frequencies. GAM has the potential to identify loci with interactions significantly above random levels, by applying statistical models that distinguish non-random contacts from the expected random behavior of loci at a given genomic distance. This can be accomplished e.g. by the SLICE computational platform (StatisticaL Inference of locus CosEgregation; see FIG. 11). SLICE returns a matrix with the statistically significant direct interactions, taking into account random proximity effects as much as other effects, such as the different compaction levels found in different chromatin regions and chromosomal territories positions. SLICE also dissects the probability of a simultaneous, three-way interaction (triplets), and more generally multivalent contacts between several loci. SLICE analysis within the GAM pipeline can also be exploited to estimate the optimal values of the control parameters required to fine tune the experimental procedure to optimize costs and efficiency under the specific application of interest, such as the ideal section thickness and the minimal number of nuclear profiles per tube, the number of tubes required in order to achieve robust detection of chromatin interactions above given thresholds, taking into account the effects of window resolution and detectability.

Mathematically, the simplest approach is to consider the random case in which loci at a given genomic distance are randomly distributed in 3D space, up to a maximum distance calculated from the assumption that chromatin is homogeneously distributed inside the nucleus. However, more advanced mathematical calculations are fully compatible with GAM and SLICE, which can take into consideration for example other spatial parameters, some of which can be measured experimentally or even be inferred from GAM data itself. For example, the volume that a chromosome, a subchromosomal region or single locus occupies in the nucleus of interest is proportional to the frequency with each its loci are found in nuclear profiles (NPs).

A plurality of loci means two or more loci, optionally, at least three, at least four, at least five, at least six, at least seven, at least eight, at least nine, at least ten, at least eleven, at least 12, at least 13, at least 15, at least 20, at least 30, at least 40, at least 50, at least 75, at least 100, at least 200, at least 500 or at least 1000 loci and up to several million or billion loci, which are analysed simultaneously. For example, allele specific analysis of a human cell at 5 kb resolution requires simultaneous analysis of 1.3 million loci. In one option, substantially all loci or all loci in a compartment are analysed with the method of the invention, e.g., by sequencing substantially all nucleic acids, preferably, all DNA, in the compartment. The loci to be analysed may be determined in a biased way (e.g. by choosing to analyse all 23000 protein coding genes in a human cell), or in an unbiased way, e.g. by dividing the genome into windows of a certain size, e.g., windows of 100 bp to 10 Mb, preferably, 1 kb to 1 Mb, 5 kb-50 kb, or 10 kb-30 kb windows. Further, the method of the invention can be applied in a way which does not distinguish between different alleles (e.g. the two homologous copies of a gene present in a normal human cell), or, alternatively, it can be used to distinguish the two (or more, in the case of e.g. polyploid amphibian cells) alleles of a locus in the same cell.

The method of the invention allows for the detection of multiple co-segregating loci, in particular, more than two co-segregating loci, preferably, more than three, more than four, more than 8, or more then 20, co-segregating loci. In contrast, the identification of multiple interactions using 3C-based methods has been attempted and shown to be both inefficient and highly biased (Sexton et al., 2012, Cell 148:458-72). There is mathematical evidence showing that these experimental limitations of 3C-based methods will remain insurmountable, irrespective of incremental improvements (O'Sullivan J. M. et al., 2013, Nucleus 4:390-8). In particular, the ligation of fragmented DNA molecules—having only two ends—with each other as a basis for identifying interactions in 3C-based methods leads to a phenomenon whereby the detection of higher multiplicity interactions becomes more difficult as the number of loci simultaneously interacting increases above three interacting loci. However, it is known that active genes often interact with three or even more enhancers (Markenscoff-Papadimitriou E et al., 2014. Enhancer Interaction Networks as a Means for Singular Olfactory Receptor Expression. Cell 159: 543-557), and that active genes interact with each other (Schoenfelder et al., 2010. Preferential associations between co-regulated genes reveal a transcriptional interactome in erythroid cells. Nat. Genet. 42: 53-61). Furthermore, restriction sites are not randomly distributed in the genome, leading to a bias in detection. The efficiency of ligation is affected by the different length of DNA fragments, which adds further bias to 3C-based results. The method of the invention is preferably not or not substantially affected by these biases (FIG. 10).

In contrast to prior art 3C-based methods, no restriction digest of nucleic acids is required in the GAM methods, which involve sectioning of the compartment. For all steps or methods of the invention, no ligation occurs between nucleic acids originally present in the compartment, in particular, no ligation has to be performed prior to step (b). However, ligation, e.g., with external linkers is possible in the context of detection of the presence or absence of nucleic acid loci, e.g., for amplification or sequencing. The avoidance of both restriction digest and ligation of nucleic acids derived from the compartment with each other overcomes the structural bias of 3C-based methods.

In this sense, GAM is unique compared with competing technologies, as it can simultaneously identify all loci present in a given section (which would be technically impossible by FISH), and it can identify proximity of loci both when they are interacting and when they are not, together with detecting the multiplicity of loci interacting simultaneously, where there are more than three loci interacting at once (which is not possible by 3C-based methods). It is also one of the advantages of the method of the invention that it can be used to identify spatial proximity of loci which were not known before the method was carried out, i.e., interactions can be identified between newly discovered or non-defined loci. For example, the method of the invention can be used to identify all loci which interact with a specific locus of interest, wherein it is not required that any of these loci are known before the analysis is carried out.

The most important limitation of FISH is that you have to know in advance what region of the genome you are interested in, while GAM allows mapping of all sequences without knowing in advance which are of interest. This is important both in research and diagnostic contexts, because important gene rearrangements often have many variants. For example, in around half to three-quarters of all prostate cancers members of the ETS gene family are joined by genome rearrangement to various gene promoters; this is of diagnostic importance (Mehra et al 2007. "Comprehensive Assessment of TMPRSS2 and ETS Family Gene Aberrations in Clinically Localized Prostate Cancer." Modern Pathology 20 (5): 538-44). In any one case, the ETS gene can be ERG, ETV1, ETV4, ETV5 and probably others (Brenner et al, 2009, Translocations in Epithelial Cancers. Biochimica Et Biophysica Acta 1796 (2): 201-15); and the ETS gene can be joined to TMPRSS2, SLC45A3, KLK2 and other genes (Brenner et al, 2009); and this can be achieved by various rearrangements (Clark et al, 2008, Complex Patterns of ETS Gene Alteration Arise During Cancer Development in the Human Prostate. Oncogene 27 (14): 1993-2003). As a result, although FISH can detect particular chosen rearrangements (Clark et al, 2008), it would not be practical to test for all known combinations by FISH, while GAM would not only find all known examples, it would discover novel patient-specific variants. A similar example would be kinase gene fusions in lung cancer that are therapeutic targets: the fusion of the EML4 and ALK genes in lung cancer, which is a therapeutic target, can usually but not always be detected by FISH (Maus et al, 2012, Identification of Novel Variant of EML4-ALK Fusion Gene in NSCLC: Potential Benefits of the RT-PCR Method. International Journal of Biomedical Science 8: 1-6), but ALK may be fused to many other genes including KIF5B, TFG, KLC1, PTPN3, and STRN (Hallberg & Palmer, 2013, Mechanistic Insight Into ALK Receptor Tyrosine Kinase in Human Cancer Biology. Nature Reviews Cancer 13 (10): 685-700), and there are other kinases that are fused, including ROS1, which is fused to at least 5 partners (Takeuchi et al 2012. RET, ROS1 and ALK Fusions in Lung Cancer. Nature Medicine 18 (3): 378-81).

The present invention also provides the use of the method of the invention for (a) determining physical distance between a plurality of loci. As the fractionation in step (a) depends on the physical distance of the loci in the compartment, the distance can be calculated. It is necessary to know the average size of the compartment from which the fractions have been generated, as well as the number of fractions into which the compartment has been divided.
(b) mapping loci and/or genome architecture in the compartment. A map can be drawn up for specific loci or the chromosomal architecture based in the physical distances determined.
(c) determining the probability of interaction between a plurality of loci. As described, the method of the invention may be used to determine specific interactions, and is capable of differentiating leading interactions from bystander interactions.
(d) determining peripheral or central position of a locus or chromosome in the compartment. The radial position of chromosomes and single loci can be inferred from asking whether the sequences from a given chromosome are more often found with fewer other windows from different chromosomes, and for this reason more likely to be found in an apical (peripheral), rather than equatorial (central), nuclear profile, and vice versa.
(e) analysing interactions of different functional elements selected from the group comprising promoters, enhancers, enzymes, e.g., involved in transcription, transposable elements, transcription factor binding sites, repressors, gene bodies, splicing signals, or RNA.
(f) identification of regulatory regions regulating expression of a specific gene.
(g) identification of targets for and/or effects of a drug capable of influencing co-segregation of loci.
(h) analysing effects of a gene therapy on co-segregation of loci. Chromosomal insertion or simply presence of a nucleic acid due to gene therapy or other genetic engineering approaches may affect genome architecture, e.g., it may enhance or prevent interaction of regulatory regions with specific promoters and thus affect transcription of "unrelated" genes. The method of the invention allows for assessment of the affects of gene therapy or genetic engineering on the level of interaction between different loci.
(i) mapping chromosomal rearrangements (such as translocations, deletions, tandem duplications, inversions), e.g., in cancer, including in specific sub-tissue cell populations, e.g. to study clonal evolution of rearrangements;
(j) analysing a disturbed co-segregation of loci in a disease;
(k) diagnosing a disease associated with a disturbed co-segregation of loci;
(l) stratifying patients with a specific disease into sub groups that are more or less likely to respond to a particular drug treatment depending on the proximity or position of certain loci or chromosomes;
(m) determining chromatin compaction, defined as the number of base pairs per unit volume. In particular, the grade of chromatin compaction at the examined loci can be determined by measuring the volume occupied by the respective loci with the method of the invention; and/or
(n) identifying loci on an exogenous nucleic acid (e.g. from a virus or a bacterium), e.g., on exogenous DNA or RNA, which interact with an endogenous locus, or identifying endogenous loci which interact with a locus on an exogenous nucleic acid.

The present invention thus also provides a method of diagnosing a disease associated with a disturbed co-segregation of loci in a patient, comprising, in a sample taken from said patient, analysing co-segregation of a plurality of loci in the patient, and comparing said co-segregation with co-segregation of said loci in a subject already diagnosed with said disease, wherein the co-segregation is preferably also compared with co-segregation in a healthy subject. Alternatively, co-segregation of loci may be compared between specific sub-groups of cells, which may be derived from the same patient, e.g., tumor cells and normal tissue. In the context of the invention, "a" is meant to refer to "at least one", if not specifically mentioned otherwise.

As the present invention may be used to investigate a disturbed co-segregation of loci in a patient, i.e., chromatin misfolding, it may also contribute to treatment of patients having a disease associated with chromatin misfolding, as such patients may, after diagnosis with a method of the invention, be treated to correct chromatin misfolding (Deng et al., 2014, Curr Op Genet Dev. 25:1-7).

For example, human disease can be caused by "enhancer adoption": the inappropriate localization of enhancers in close spatial proximity to genes that they do not normally regulate (Lettice et al., 2011, Hum Mutat. 32:1492-1499). The method of the invention may be used to investigate the spatial proximity of an enhancer in patient-derived tissues, in order to diagnose the patient with, for example, a particular subtype of cancer (Northcott et al. 2014, Nature 511:428-434). Alternatively, if a patient presents with symptoms normally caused by overexpression of a particular gene, the method of the invention may be used to identify enhancers that have become localized proximal to the gene of interest and that therefore may present potential targets for therapeutic intervention. In other situations, disease-associated genetic variants in coding regions of a given gene may lead to altered gene expression of that gene that confounds discovery of a mis-regulated chromatin contact which directly explain the disease phenotype, but is only uncovered by unbiased mapping of chromatin contacts (Smemo et al. 2014 Obesity-associated variants within FTO form long-range functional connections with IRX3. Nature 507, 371). The method of the invention can thus be used for diagnosis of, e.g., cancer or genetically predisposed obesity.

Much of clinical genetics is the diagnosis of genetic disease such as developmentally delayed children (Cooper, G. M., et al. 2011. A copy number variation morbidity map of developmental delay. Nat. Genet. 43, 838-846) or schizophrenia (Cook, E. H., Jr., and Scherer, S. W. 2008. Copy-number variations associated with neuropsychiatric conditions. Nature 455, 919-923), which are often caused by structural mutations in genome such as deletions and chromosome translocations. Most are beyond the ability of cytogenetics, even where cytogenetics can detect part of the rearrangement (Gribble et al, 2005. The Complex Nature of Constitutional De Novo Apparently Balanced Translocations in Patients Presenting with Abnormal Phenotypes. Journal of Medical Genetics 42 (1): 8-16; De Gregori, M., et al. 2007. Cryptic Deletions Are a Common Finding in 'Balanced' Reciprocal and Complex Chromosome Rearrangements: a Study of 59 Patients. Journal of Medical Genetics 44 (12): 750-62), and, in the majority of cases, there is no candidate gene—almost any part of the genome may be altered—so FISH is of no value. Whole genome sequencing may find candidate rearrangement junctions, but not all will be detected, some rearrangement junctions will be artefacts, and interpreting the junctions found in terms of deletions, insertions or translocations is not robust and is difficult to verify. GAM provides information about abnormal proximity of large stretches of genome: at the very least this complements whole genome sequencing and is likely to be a better first approach for finding substantial structural changes.

The invention provides integrated genome-wide information about radial position, chromatin contacts, and chromatin compaction in one single embodiment, which has the potential of providing more refined predictive markers of disease state. Currently, the three parameters are studied independently using separate approaches. For example, locus-specific radial reposition of specific genomic loci has been identified in association with prostate cancer and/or hyperplasia which indicates locus-specific reorganisation during disease progression and the potential to stratify patients (Leshner M et al. 2015. Locus-specific gene repositioning in prostate cancer. Mol Biol Cell. 2015. pii: mbc.E15-05-0280. [Epub ahead of print]). Altered radial position of specific genomic loci has also been identified in human invasive breast cancer compared to normal breast tissue, which are independent of genomic instability (Meaburn K J et al. 2009 Disease-specific gene repositioning in breast cancer. J Cell Biol.; 187(6):801-12. doi: 10.1083/jcb.200909127). Altered chromatin contacts have also been found in association with different stages of breast cancer progression, such as decreased contacts between two different chromosomes, and between sub-chromosomal regions (Barutcu A R et al. 2015. Chromatin interaction analysis reveals changes in small chromosome and telomere clustering between epithelial and breast cancer cells. Genome Biol. 16(1):214. doi: 10.1186/s13059-015-0768-0).

The following examples are included to illustrate the invention, not to limit its scope. Methods of sample preparation and analysis and/or statistical methods used in the examples may also be used in the method of the invention to analyse samples of different origin and/or for different loci of interest, e.g., as mentioned herein. Literature cited is herewith fully incorporated herein for all purposes.

FIGURE LEGENDS

FIG. 1: Genome architecture mapping can measure nuclear proximity of loci by measuring their co-segregation in nuclear slices.

a, Loci which are close along the linear genome may not be in close proximity in the nucleus, so methods are required to measure the distances between loci in the nuclear space. b, When thin slices are taken through a nucleus (nuclear profiles or NP), loci which are closer together in the nuclear space are more frequently found in the same NP. c, In principle, any method of DNA detection (PCR, next-generation sequencing etc.) can be used to score locus presence or absence in each NP. d, When loci are scored in a large enough number of NPs, the co-segregation of loci can be used to generate co-segregation matrices, which indicate the nuclear distance between pairs of loci.

FIG. 2: GAM independently reproduces features of genome architecture previously found in Hi-C studies.

a, Sequencing tracks from individual NPs show patterns consistent with a chromatin fibre looping in and out of a thin slice, b, The sequencing depth obtained by multiplexing 48 NPs on a single 1 HISEQ lane is sufficient to saturate the detection of 30 kb windows in each sample. Moreover, the percentage of genomic 30 kb windows identified in almost all NPs is within the range of the percentage of nuclear volumes expected from 220 nm slices of a 9μm diameter sphere, c, GAM and FISH show similar detection efficiencies of three ~40 kb regions in the HoxB locus, d, GAM and Hi-C identify similar A and B compartments by PCA at 1 Mb resolution (65% compartment overlap), e, GAM identifies topologically associating domains similar to those identified by Hi-C.

Figure 3:
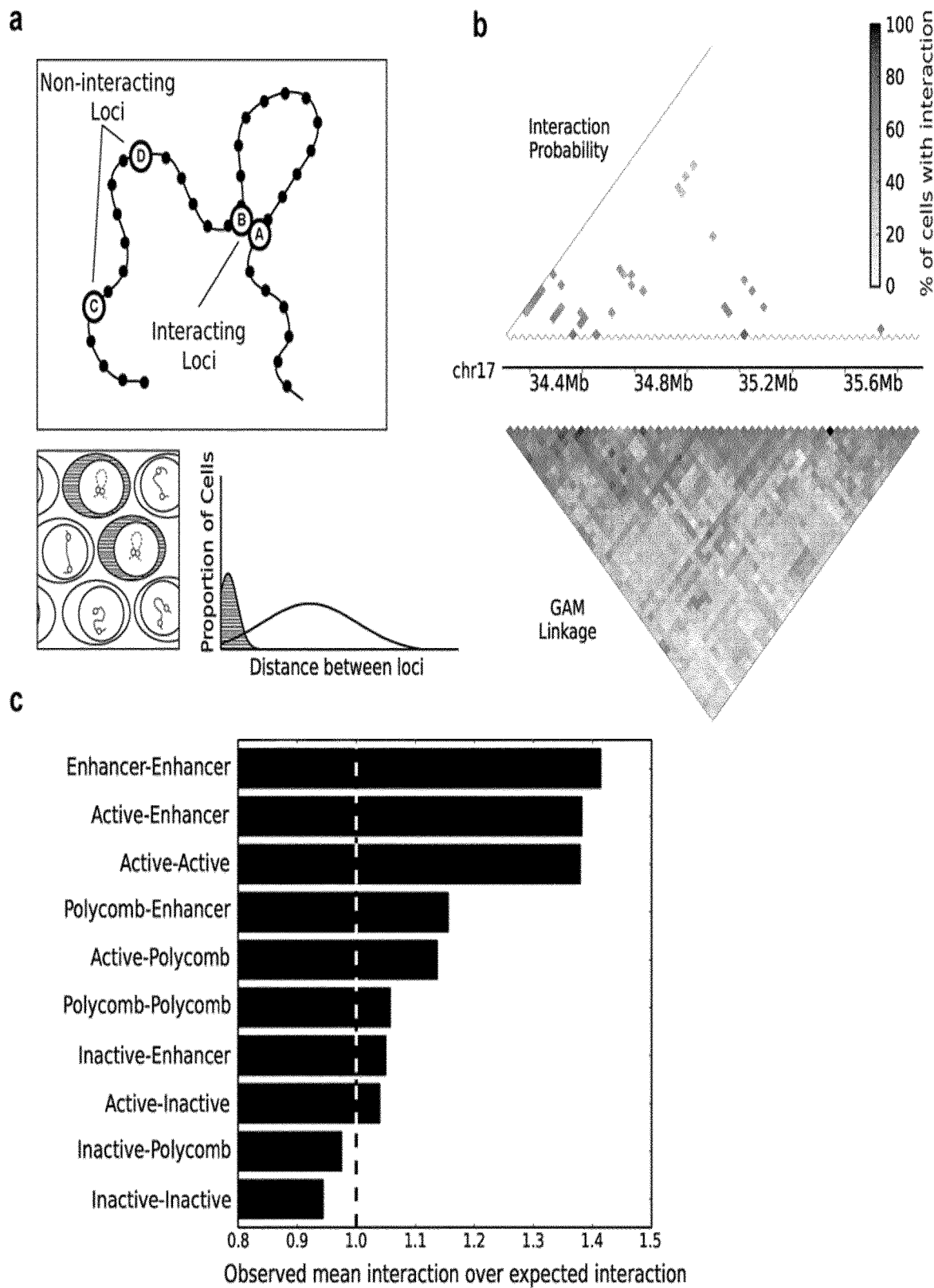

FIG. 3: Interaction probability matrices extracted by a simple modelling approach are enriched for contacts between enhancers and active genes.

a, Loci which are closer in nuclear space than expected by random chromatin folding can be modelled as a large population of cells in which the loci are distributed following the random case, and a small sub-population of cells which demonstrate a much closer interaction. This model assumes therefore a bi-modal distribution of nuclear distances. b, Modelling pairs of loci as mixtures of strongly interacting or randomly folded states identifies discrete interaction foci in the Pou5f1 locus. c, A statistical enrichment for interactions within and between 30 kb windows overlapping enhancers or active genes was identified by calculating the mean interaction probability estimated with SLICE between all 30 kb windows overlapping two specific features (e.g. between all windows overlapping active genes and those overlapping enhancers) and comparing to the same value obtained after randomization of the matrix diagonals.

FIG. 4: Limitations of current genome-wide methods for measuring chromatin contacts.

The table lists the current genome-wide methods for measuring chromatin interactions and compares their various limitations. GAM suffers from few of the limitations that affect current genome-wide methods for mapping genome architecture.

Figure 5:
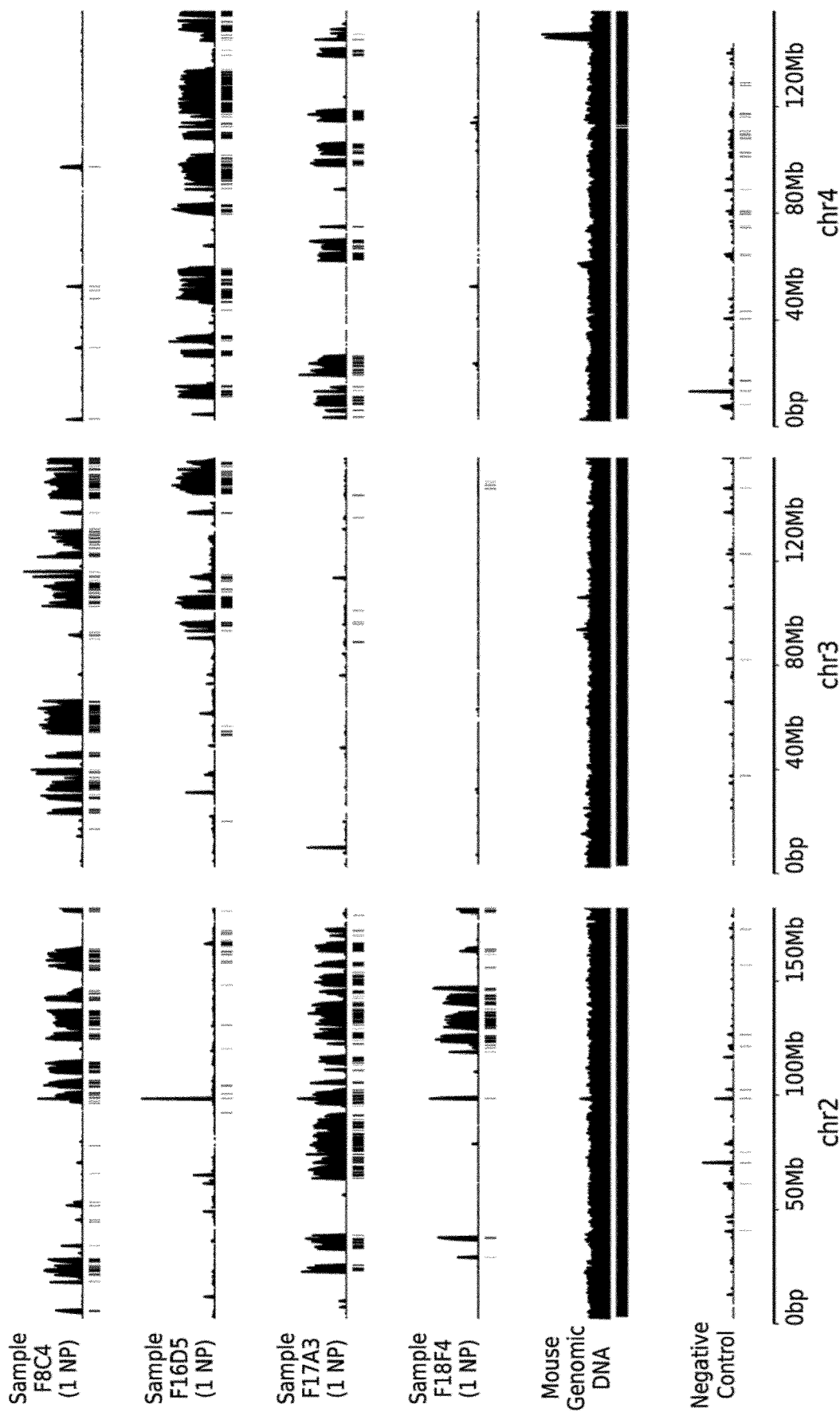

FIG. 5: Outline of the GAM method.

a, In the presented embodiment of the invention, GAM combines the existing technologies of cryosectioning, laser capture microdissection, whole genome amplification and next-generation sequencing in a novel sequence of steps. b, Cryosectioning produces a slice through a field of nuclei, with an extremely thin section thickness. c, Individual NPs are identified and isolated from cryosections using laser capture microdissection. d, Whole genome amplification is used to extract and amplify DNA from isolated NPs through microdissection. hgDNA, human genomic DNA. e, Next generation sequencing identifies which loci of the mouse genome were present in each original NP. As expected from random sectioning, each NP contains a different complement of chromosomes and subchromosomal loci therein, and not all chromosomes are identified in each NP.

FIG. 6: Quality control of the GAM dataset.

a, The percentage of reads mapped to the mouse genome and the total number of identified windows were found to be the best discriminator of negative controls. No batch effects were identified in these parameters between groups of NPs collected on the same day and processed together. NPs with <15% reads mapped to the mouse genome were discarded before further processing. b, Almost all genomic windows at resolutions from 30 kb to 1 Mb are detected in at least one NP (grey bars). Some windows have no defined sequence in the mm9 assembly (e.g. at centromeres) and therefore are not detected (black lines). The proportion of windows detected in at least one NP increases with decreasing genomic resolution (i.e. increased window size). c, An average of 6% of each chromosome is found in single NPs, and this proportion is constant across chromosomes.

FIG. 7: Normalization of co-segregation matrices to account for differences in locus detection frequency.

a, The distribution of detection frequencies for individual 30 kb windows deviates slightly from the binomial distribution which would be expected if all loci were detected independently. b, The detection frequency of 30 kb windows is mostly independent of their GC content, or from the fraction of the window which is annotated as a genomic repeat. Detection frequency does correlate with mappability. c, Differences in the detection frequency between loci can subtly affect co-segregation matrices, but can be corrected by calculating the normalized linkage disequilibrium.

Figure 8:
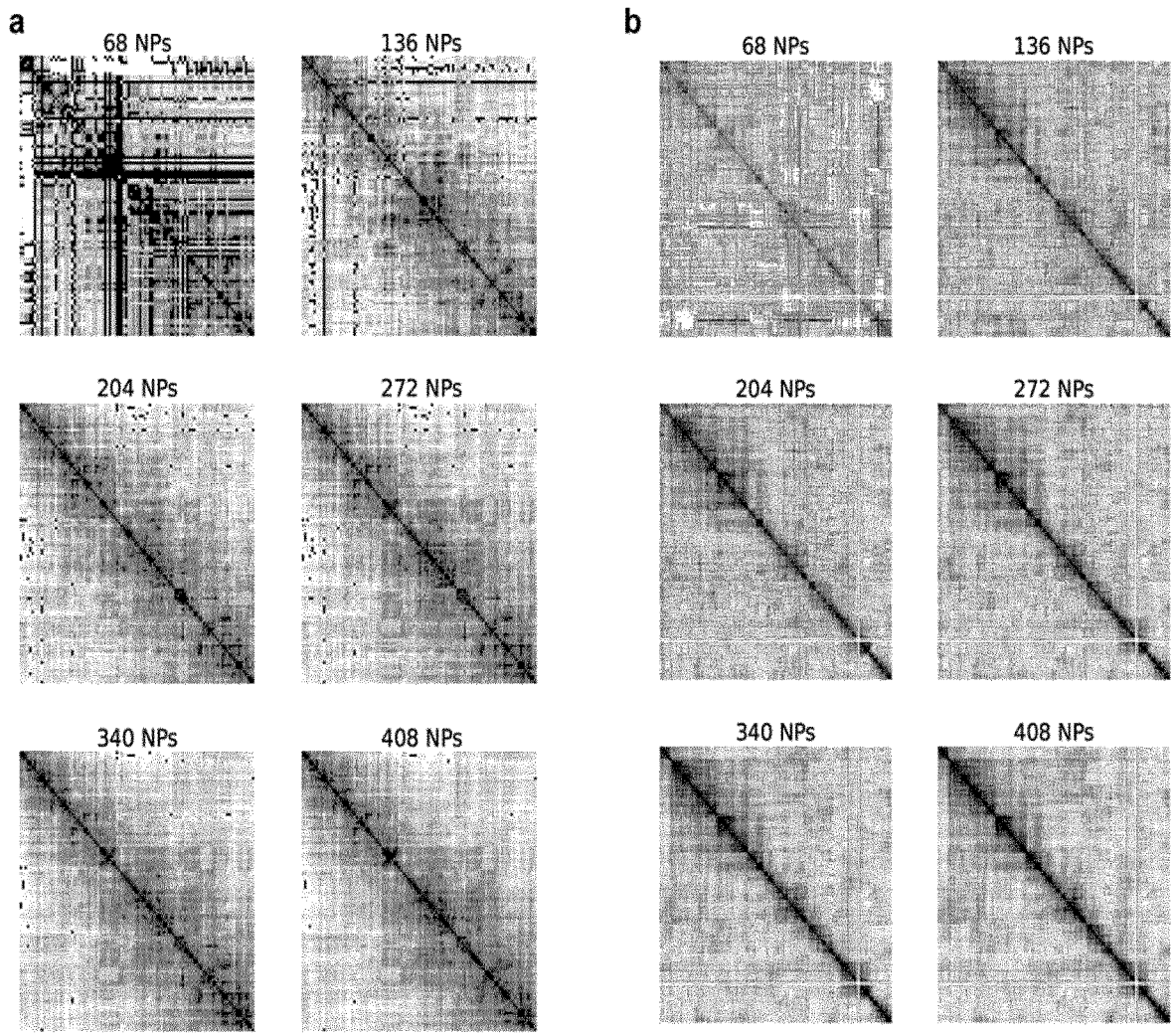

FIG. 8: Four hundred and eight NPs are sufficient to extract most of the information about co-segregation of pairs of loci at 30 kb resolution.

a, The initial batch of 408 NP datasets that passed quality control was eroded 6 times, randomly removing 68 NPs each time. Then, the co-segregation matrix for the Esrrb locus on murine chromosome 12 was plotted with increasing numbers of NPs. The structure of the matrix approaches stabilization when at least about 200 NPs are included. b, The same stabilization of the co-segregation matrix is observed for a larger region (30 Mb, the smaller Esrrb locus from panel a corresponds to the bottom right hand corner). c Plotting the Pearson Correlation Coefficient (PCA) between each of the eroded datasets and the 408 NP full dataset confirms that the co-segregation matrix begins to saturate after around 200 NPs are collected.

Figure 9:
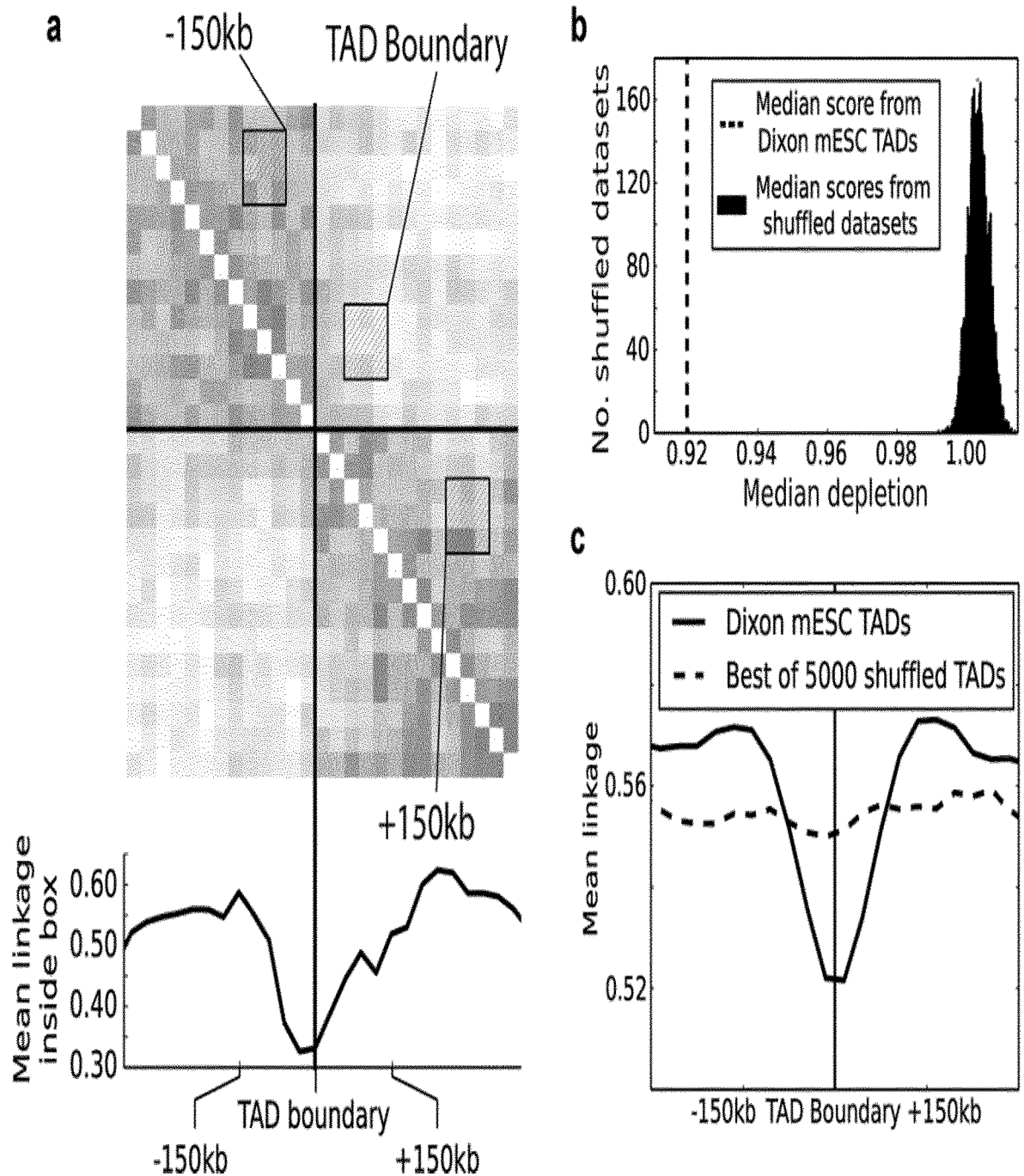
Figure 10A:
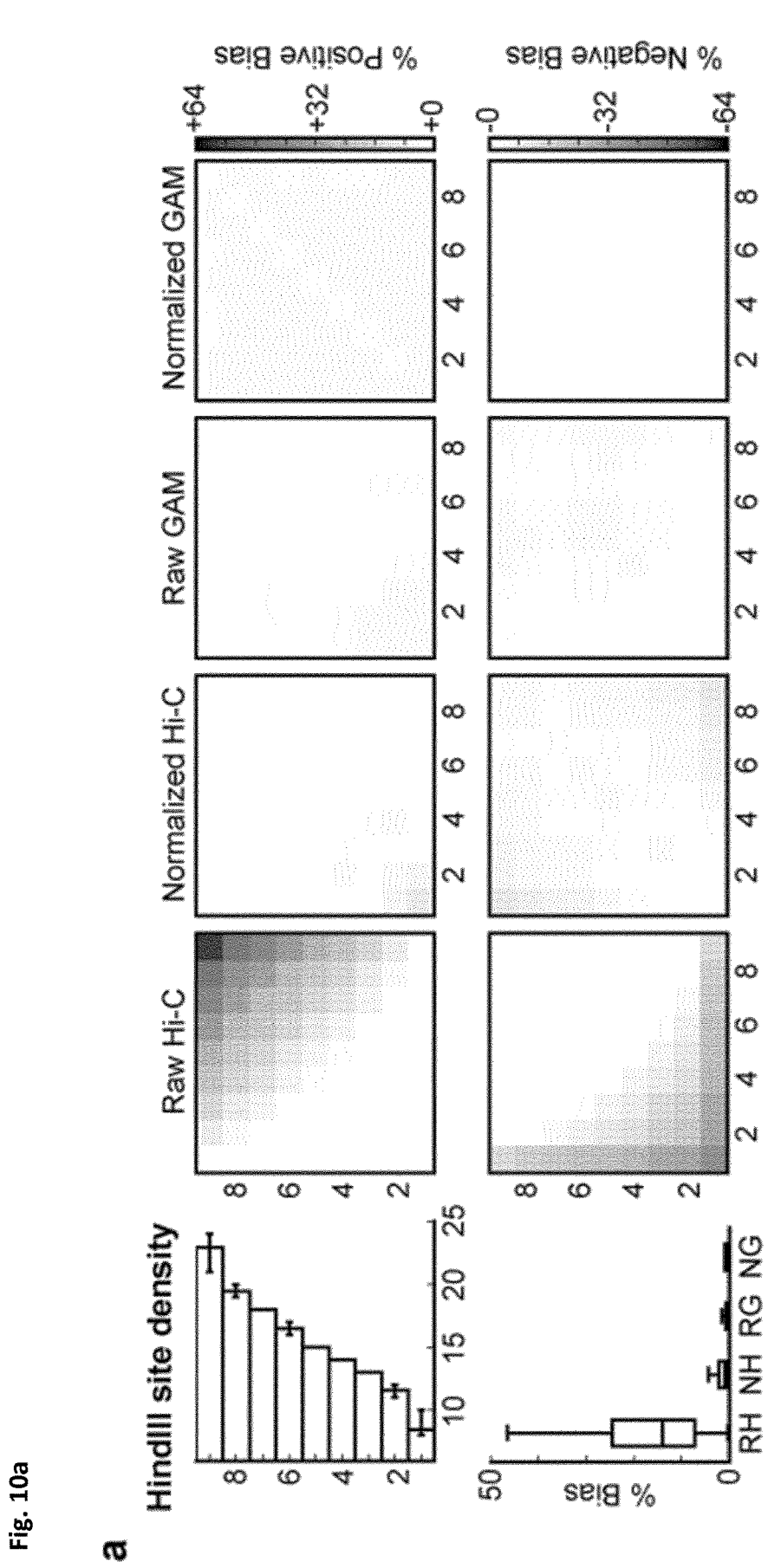
Figure 10B:
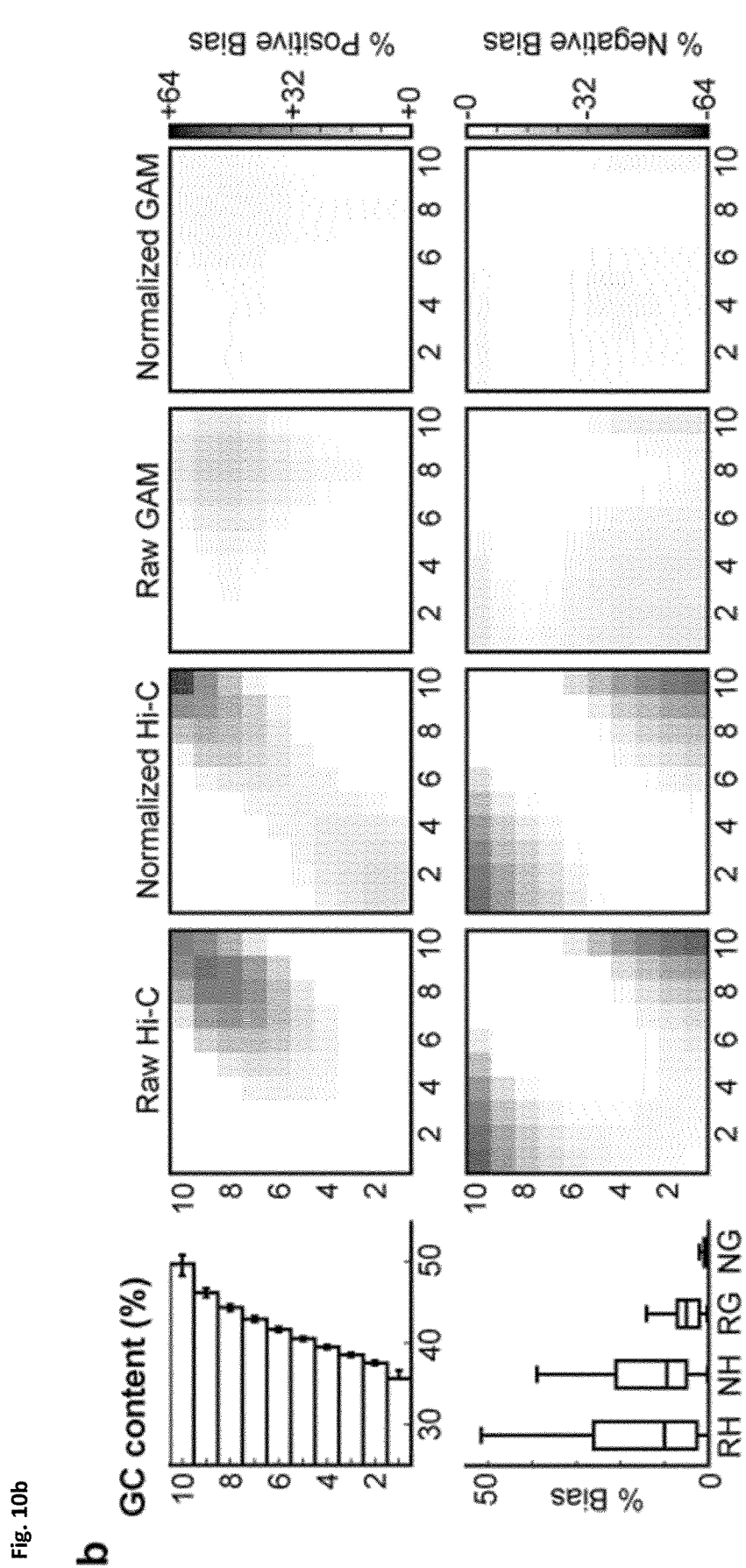
Figure 10C:
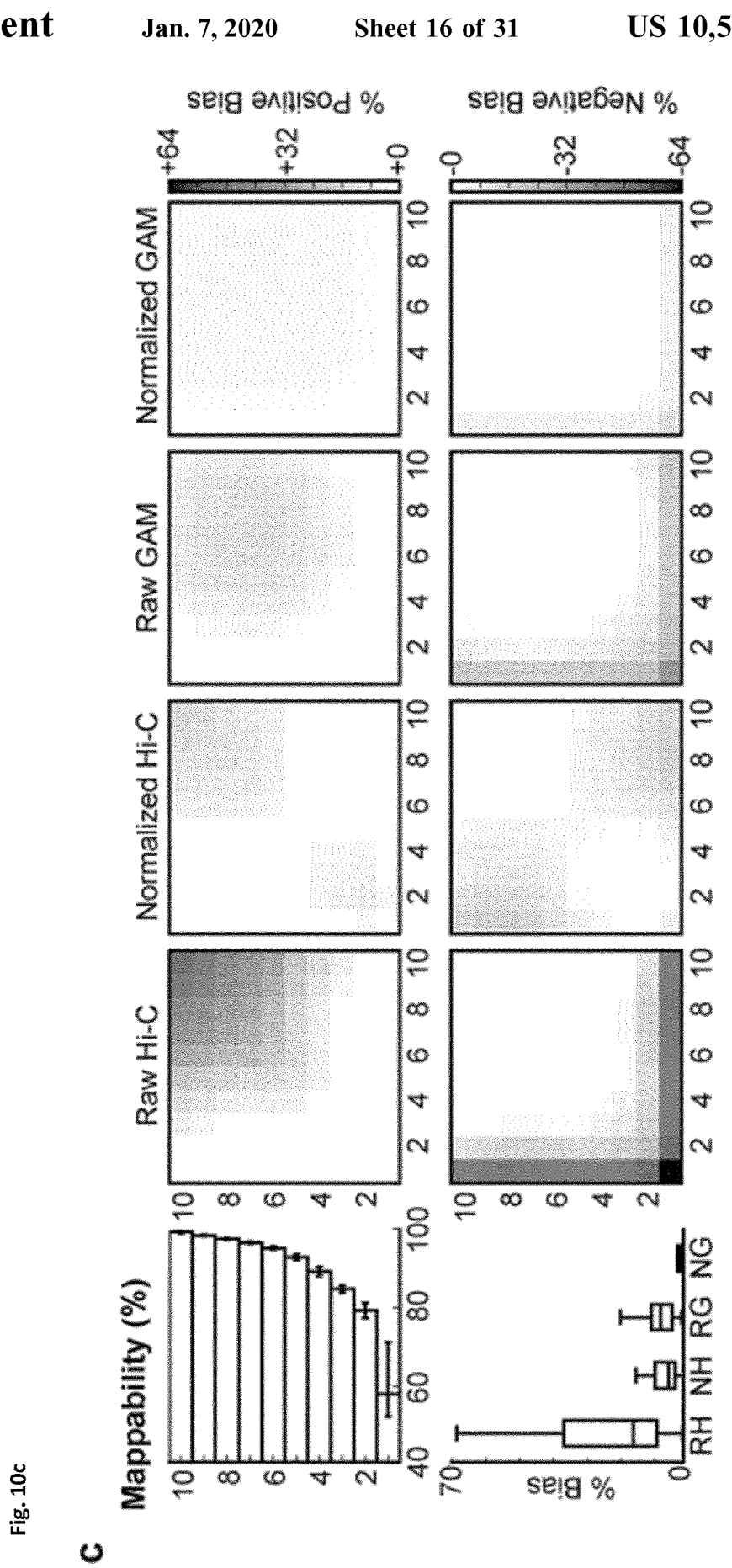
Figure 10D:
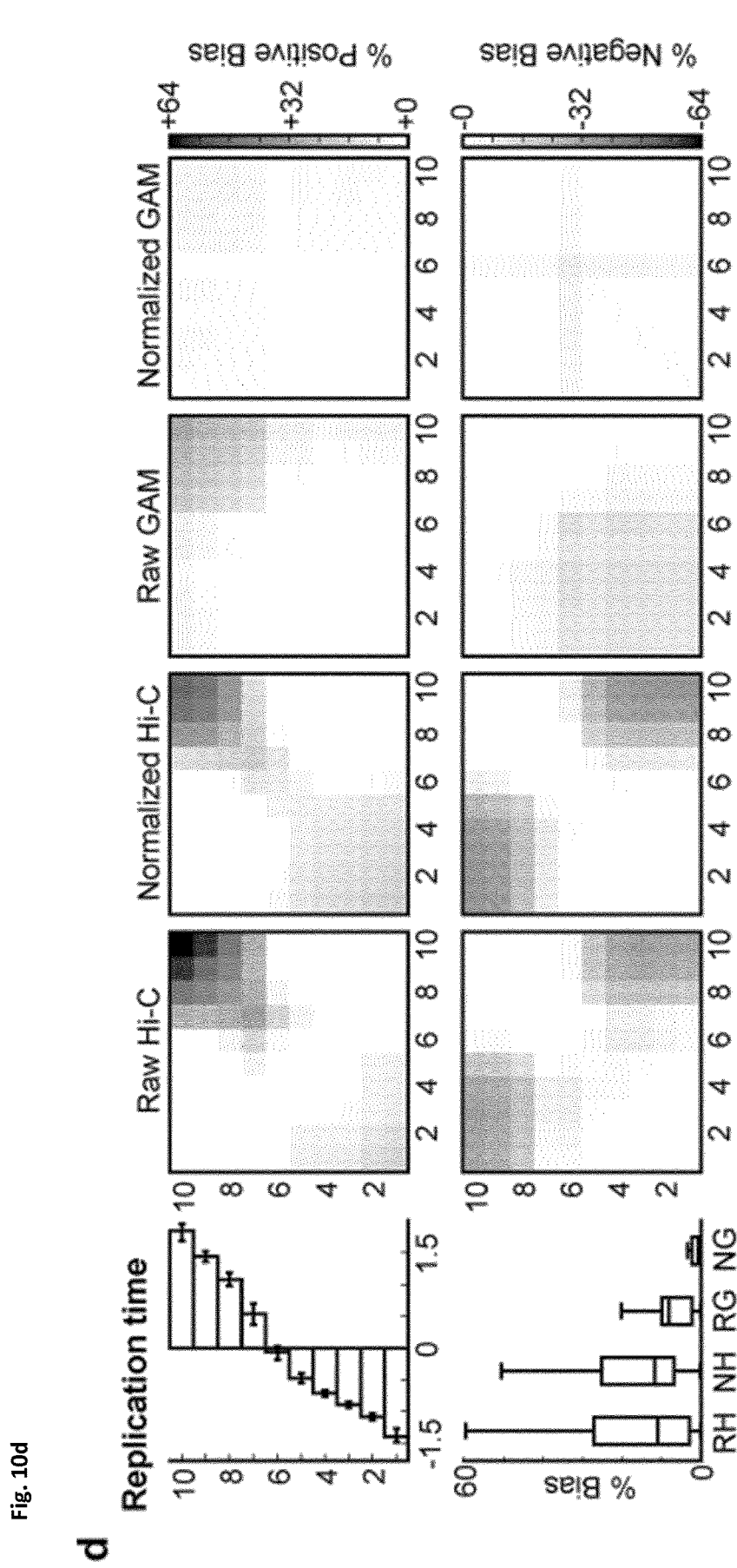
Figure 10E:
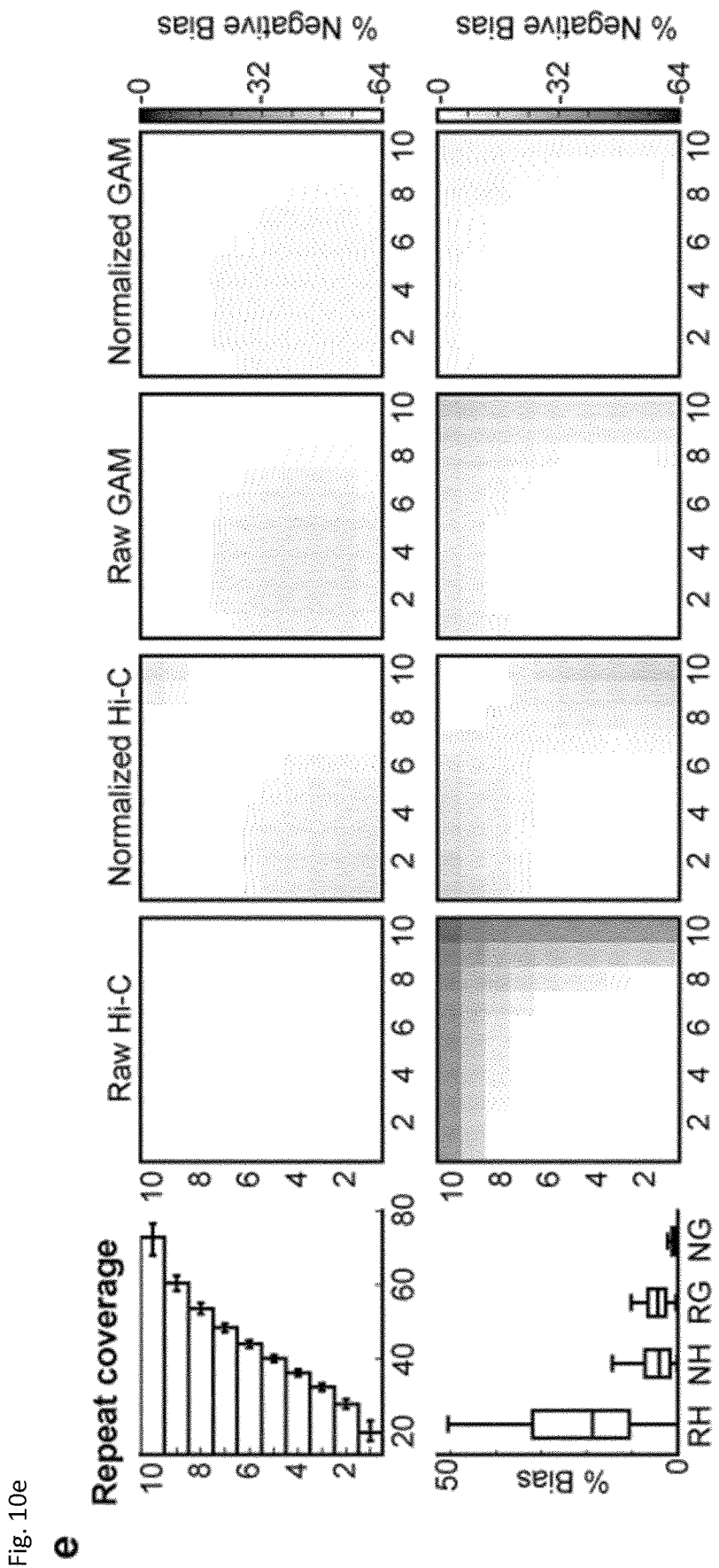

FIG. 9: GAM reproduces a significant depletion of off-diagonal contacts around previously identified TAD boundaries.

a, Off-diagonal contacts were quantified as the mean normalized linkage in a 3×3 box moved at an offset of 2 from the matrix diagonal. This mean normalized linkage is lower around a TAD boundary identified by Hi-C (Dixon J. R. et al., 2012. Topological domains in mammalian genomes identified by analysis of chromatin interactions. Nature 485, 376-380). b, The off-diagonal depletion was calculated for each TAD boundary in a previously published list of TAD boundaries in mouse ES cells (mESC), and the median depletion of these boundaries was found to be greater than that observed in any of 5000 randomly shuffled lists of TAD boundaries. c, The profile of off-diagonal interactions averaged over all TAD boundaries shows a large depletion at the boundary. The largest depletion observed for 5000 lists of shuffled boundaries is shown for comparison.

FIG. 10: Bias in the measurement of chromatin contact strength in Hi-C and GAM data, before and after normalization Raw Hi-C data displays a greater level of bias with respect to a, restriction site density, b, GC content, c, mappability, d, replication time and e, repeat coverage than raw GAM data. Normalization of Hi-C data (ICE) only partially removes biases, whilst biases in GAM data are effectively removed after normalization. For each potential source of bias, we divided all 50 kb windows in the mouse genome into 10 equal groups (or 9 groups in the case of HindIII site density) based on the potential bias in question. The mean ±upper and lower quartiles for each group are shown in the top left bar chart. We then calculated the observed chromatin contacts (raw Hi-C: ligation frequency, normalized Hi-C: ICE normalized ligation frequency, raw GAM: co-segregation frequency, normalized GAM: normalized linkage disequilibrium) between windows in each of the 10 groups and divided each observed value by the average value for all windows separated by that genomic distance (the expected value). The heatmaps show the average observed/expected values between each pair of groups. Top row (% positive bias) shows combinations of groups which have higher than expected chromatin contacts given their genomic distance, bottom row (% negative bias) shows combinations of groups with lower than expected contacts. The bottom right boxplot summarizes the absolute bias (i.e. both positive and negative bias) over all possible combinations of groups.

FIG. 11: The SLICE statistical method for detecting significantly interacting locus pairs from GAM data a) The inventors' statistical modelling of locus pair co-segregation is named SLICE (Statistical Inference of Co-segregation). Locus pairs (each homologous copies) across the genome exist in interacting or non-interacting states. Slices through nuclei can contain both loci ($M_2$), one locus only ($M_1$) or neither locus ($M_0$). Interacting or non-interacting locus pairs have different slice co-segregation frequencies across the population of nuclei. The probability of interaction (Pi) of any two loci in the original population is estimated from the observed co-segregation frequency. b) SLICE derives the expected co-segregation frequency of a locus pair in the different cases; i.e., the probabilities that 0, 1 or 2 loci in a pair co-segregate when they are in an interacting ($t_0, t_1, t_2$) or non-interacting state ($u_0, u_1, u_2$). As an example, we show here the formula for $u_2$ in a slice $V_{slice}(z)$ for a pair of loci at a distance d and positioned in the nucleus with a distribution p. c) Hence, the expected number of NPs can be derived as a function of Pi and compared with observed data, once the probabilities of the nucleus states $P_2$, $P_1$ and $P_0$ have been defined.

Figure 12:
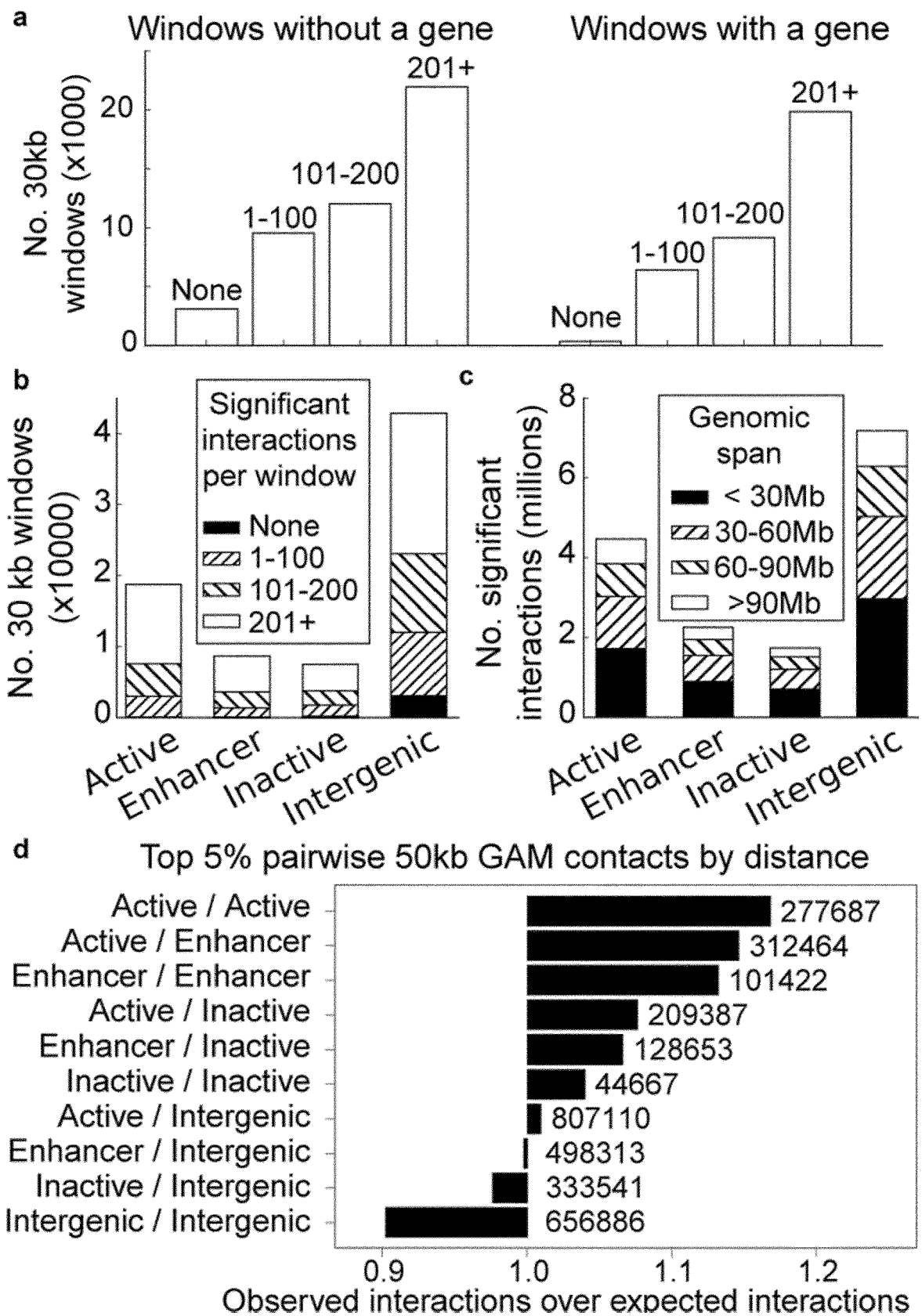

FIG. 12: Chromatin interactions identified by the SLICE statistical model include many different genomic features and extend over large genomic distances.

a, Number of significant interactions involving 30 kb windows either overlapping or not overlapping a gene. b, Number of significant interactions by overlapping feature present in each window. c, Genomic distances between pairs of windows with significant interactions by overlapping feature. d, The statistical enrichment for interactions within and between 30 kb windows overlapping enhancers or active genes was reproduced without SLICE analysis by identifying the top 5% interacting pairs of loci at each genomic distance from normalized linkage disequilibrium matrices, and then counting the number of these interactions involving windows overlapping two specific features (e.g. the number of top 5% interactions identified between windows overlapping active genes and those overlapping enhancers). Enrichment was then calculated by comparing to the same value obtained after randomization of the interaction positions.

Figure 13:
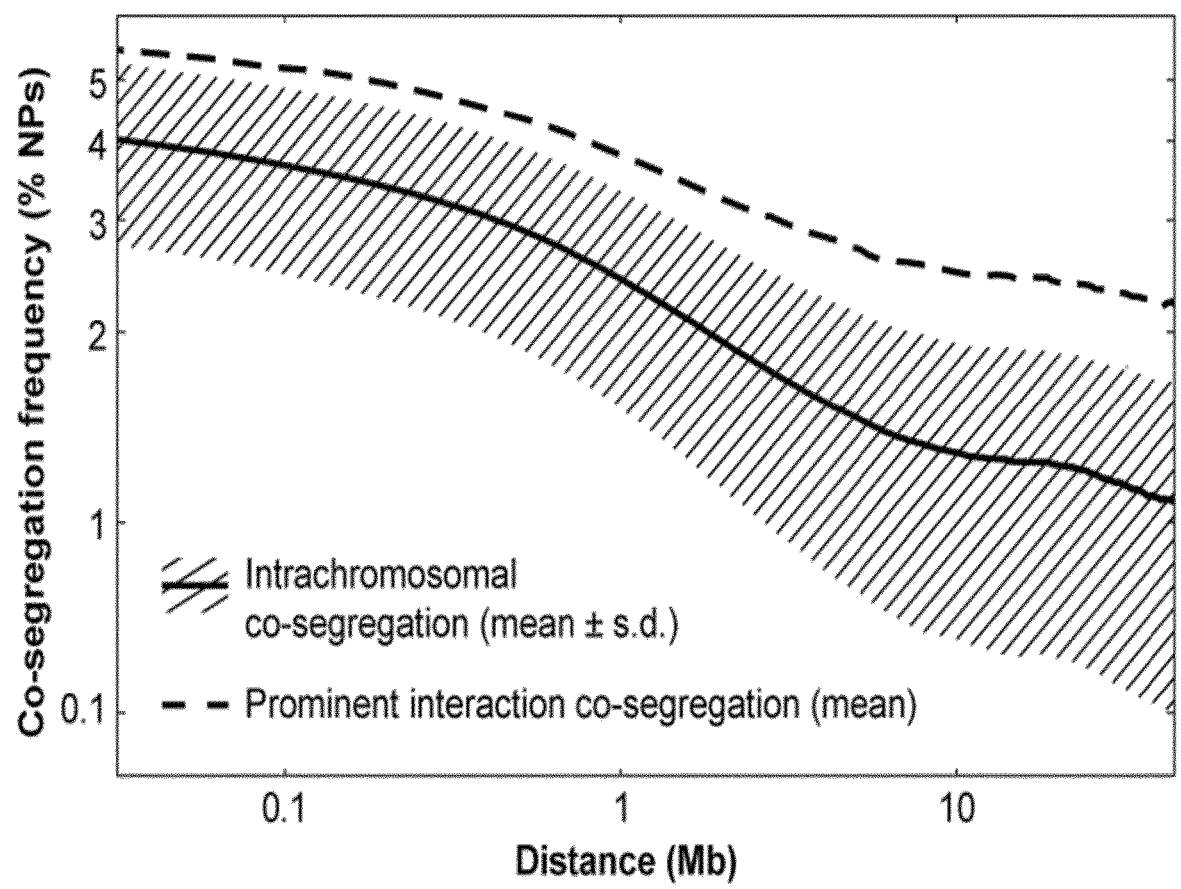

FIG. 13: Significantly interacting locus pairs identified by SLICE co-segregate more frequently than non-interacting locus pairs across all genomic distances Mean co-segregation frequency of pairs of significantly interacting windows identified by SLICE (solid line) is consistently higher than the mean co-segregation frequency of non-interacting windows (dashed line) ±standard deviation (hatched area) across a wide range of genomic distances.

FIG. 14: Super-enhancers are highly enriched among the most highly interacting TAD triplets identified by GAM.

a, 2D interaction matrices can show overlapping contacts between three regions, which can be incorrectly interpreted as a single simultaneous triplet interaction. With pairwise contact data alone, the simultaneous case is indistinguishable from separate pairwise events (or a complex mix of the two). b, Strategy for identifying TADs most likely to be involved in truly simultaneous, three-way interactions. Bottom graph shows the final ranking of TAD triplets according to their triplet interaction score, and the position of the threshold above which TAD triplets were taken to be truly simultaneously interacting. c, Example of a three-way interaction between TADs on chromosome 1. Matrix shows significant pairwise interactions over the entire region, insets show zoom of significant interactions between the three TADs. Classification of TADs is shown below. d, Non-adjacent top 5% TAD triplets overlapping the genomic region shown. Each vertical line connects three TADs that are likely to interact simultaneously (based on their frequent co-segregation across the population of NPs). e, Classification of TADs. TADs overlapping Super Enhancers are designated SE. Non-SE TADs are designated low transcription when their GRO-seq coverage is in the bottom 25% quartile, or high transcription when it is in the top 25%. f, Genomic span of top 5% triplet interactions by TAD class. g, Top 5% triplets are highly enriched for TADs containing an SE region, and highly transcribed TADs, with interactions between three SE TADs being the single most enriched combination. Bars shown in red or blue are respectively enriched or depleted relative to the value obtained after random shuffling of triplet positions. h, Percentage of TADs in each class that overlap Lamina Associated Domains (LADs) from Peric-Hupkes et al. (2010)[50]. i, Highly transcribed and SE TADs that form the least triplet contacts more frequently overlap or are closer to LADs compared with TADs that form the most triplet contacts.

FIG. 15: Analysis of TADs interacting in triplets.

a, Enrichment analysis as in FIG. 14g additionally showing TADs not falling into any of the other classes (medium TADs). b, Strategy for refining the discovery of specific binding sites by identifying average linkage at 5 kb resolution, within each 30 kb window. For each significant interaction identified by SLICE connecting 30 kb windows in the Active or Enhancer class, we asked whether specific sub-windows within the larger 30 kb window displayed the highest linkage with the partner 30 kb window. In particular, we were interested in asking whether e.g. the 5 kb windows overlapping the active gene promoter (or TSS, transcription start site), or the active gene TES (transcription end site) or the enhancer could be most often co-segregated with the partner 30 kb window. c, Average linkage to significantly interacting Active 30 kb windows (solid line) or Enhancer 30 kb windows (dashed line) is enriched for 5 kb windows overlapping active gene TSSs (left), active gene TESs (middle) or enhancers (right) compared to all the 5 kb windows that lie 15 kb upstream or downstream of these features. This enrichment is not seen for all other 5 kb windows that also overlap active gene TSSs, TESs or enhancers but do not significantly interact with the same Active 30 kb windows (control windows; dotted line). d, Strategy for identifying average three-way linkage at 40 kb resolution. For each top triplet interaction connecting three super-enhancer (SE) TADs, we asked whether, within the whole TAD, the 40 kb window directly overlapping the super-enhancer displayed the highest three-way linkage with the other two interacting super-enhancer TADs. e, Average three-way linkage to two other super-enhancer TADs forming a top triplet (solid line) is enriched for the 40 kb window directly overlapping the super-enhancer compared to the 40 kb windows 120 kb upstream or downstream of the super-enhancer. This enrichment is not seen between a super-enhancer (SE) and two highly expressed (High) TADs forming a top triplet (dashed line), nor is it observed between a super-enhancer and two other super-enhancer TADs which are not involved in a top triplet (dotted line).

FIG. 16: GAM also provides information about locus radial positioning and compaction.

a, A locus positioned centrally within the nucleus is more frequently found in equatorial NPs, which have a larger volume. In contrast, a locus positioned close to the nuclear periphery is more frequently found in apical sections, which have a smaller volume. b, The mean percentage of the genome covered per NP (as a proxy for NP volume) is negatively correlated with radial positioning in the five mouse autosomes for which radial position data is available. c, A more de-compacted locus with a larger volume is intersected more frequently (i.e. is detected in more NPs) than a corresponding compacted locus with a larger volume. d, 30 kb windows in higher quartiles of detection frequency show a greater mean DNase signal (a measure of local chromatin accessibility), as expected if detection-frequency is a measure of chromatin compaction, since more compact chromatin is likely to be less accessible. e, 30 kb windows in higher quartiles of detection frequency also show a higher coverage by GRO-seq, indicating a greater level of active transcription. This is consistent with a general decompaction of actively transcribed chromatin regions, leading to a volume-induced increase in detection frequency.

EXAMPLES

Thin nuclear cryosections were produced in the absence of resin-embedding, by a modified Tokuyasu method (Tokuyasu, K. T., 1973, J. Cell Biol. 57, 551-65, A technique for ultracryotomy of cell suspensions and tissues; Guillot P V, Xie S Q, Hollinshead M, Pombo A (2004) Fixation-induced redistribution of hyperphosphorylated RNA polymerase II in the nucleus of human cells. Exp. Cell Res. 295, 460-468; Pombo A, Hollinshead M, Cook P R (1999) Bridging the resolution gap: Imaging the same transcription factories in cryosections by light and electron microscopy. J. Histochem. Cytochem. 47, 471-480), which involves cryoprotection of fixed tissues using embedding in a saturated sucrose solution followed by freezing in liquid nitrogen, and sectioning at −100° C. The feasibility of DNA extraction and detection from cryosectioned material was tested. mESCs were cryosectioned at a thickness of 220 nm according to established protocols[3] (FIG. 5a,b). Single nuclear profiles (NPs) were isolated from the section by laser microdissection[4] (FIG. 5c). DNA was then extracted, fragmented and amplified using single-cell whole genome amplification (WGA)[5] (FIG. 5d).

WGA-amplified DNA from single NPs was sequenced using Illumina HISEQ technology. Visual inspection of tracks from single NPs showed that each contains a different complement of sub-chromosomal regions (FIG. 5a), as expected from chromatin passing in and out of a thin nuclear slice. Furthermore, each NP contained only a restricted subset of chromosomes (on average, 7 chromosomes per NP; FIG. 5e).

Having confirmed the feasibility of extraction and detection of DNA by genome-wide sequencing methods, the mouse genome was divided into windows of equal size in order to measure their co-segregation. To determine the appropriate genomic resolution (window size), regular genomic windows over a range of sizes from 10 kb to 1 Mb were defined and an adaptation of previously described negative-binomial approaches was used to detect the presence of these windows in individual NPs. Sequential erosion of sequencing reads was used to determine the depth of sequencing required to saturate the detection of positive windows in each sample (FIG. 2b). 600 k unique reads were sufficient to saturate the detection of 30 kb windows for >95% of tested samples, which allows multiplexing of 48 NPs on a single HISEQ lane.

Mapping Chromatin Contacts Using GAM

To map chromatin contacts genome-wide using GAM, 490 individual NPs were sequenced. The quality of each dataset was assessed based on a combination of criteria including percentage mapped reads. Samples were collected in 15 batches of up to 48 NPs, and quality control metrics were reproducible between independently collected batches (FIG. 6a). A small number of single NP datasets (82 samples) were discarded from further processing after quality control based on a low percentage (<15%) of mapped reads to the mouse genome.

To explore the extent of genomic coverage attained in our dataset of 408 NPs, the extent of detection of different genomic regions across the whole dataset and in each NP was computed. 96% of all genomic 30 kb windows were detected in at least one NP (FIG. 6b). Single NPs contained an average of 6±4% of 30 kb windows. This is in line with the range of nuclear volumes expected to be contained in single NPs, as mESC nuclei have an average diameter of 9 µm, and sections are 0.22 µm thick. The average fraction of enriched windows across NPs was constant between different chromosomes (FIG. 6c). Taken together, these results show robust DNA extraction and detection from single NPs by combining WGA with Illumina sequencing.

To further test the robustness of detection, the frequency of detection of single loci was compared by GAM and Fluorescence In-Situ Hybridization (FISH) at ~40 kb resolution. Three genomic windows across the HoxB locus were tested, and a remarkable agreement was found between FISH and GAM with a detection frequency of 7-12% for the three 40 kb windows in both methods (FIG. 2c). Next, the genome-wide frequency of locus detection was measured across the whole dataset of NPs. As expected, the distribution of locus detection frequencies is well approximated by a binomial distribution (FIG. 7a). Slight deviations from this distribution are only weakly correlated with GC content or the fraction of the window covered by genomic repeats, correlating most strongly with mappability (FIG. 7b). Such deviations could originate from the small proportion of loci which are interacting with each other in a given NP, leading to incomplete independence of the detection probability between loci. In conclusion, GAM datasets are minimally influenced by systematic biases in the detection of different genomic windows, in contrast with 3C-based methodologies (FIG. 10). This is likely due to the reliance of 3C-based methods on precise mapping of a small number of reads close to specific restriction enzyme sites, whilst GAM can detect any nucleic acid fragment within a much larger genomic region.

To map chromatin contacts measured by GAM, the matrix of locus co-segregation across the whole NP cohort was plotted for each individual chromosome. Although little systematic bias influencing the detection of individual loci was detected, nevertheless some loci are detected more frequently than others simply due to the probabilistic nature of cutting NPs in random orientations. These differences in the detection frequency of different loci were corrected for using a normalized version of the linkage disequilibrium, as previously described[6] (FIG. 7c, FIG. 10). 408 NPs is sufficient to begin to explore genome architecture as co-segregation matrices obtained by using fewer NPs do not show dramatic differences from around 280 NPs (FIG. 8a). This observation was confirmed by calculating the correlation between the full dataset of 408 NPs and the eroded datasets, finding that Pearson correlation coefficient saturates at around 300 NPs (FIG. 8b).

Figure 2D:
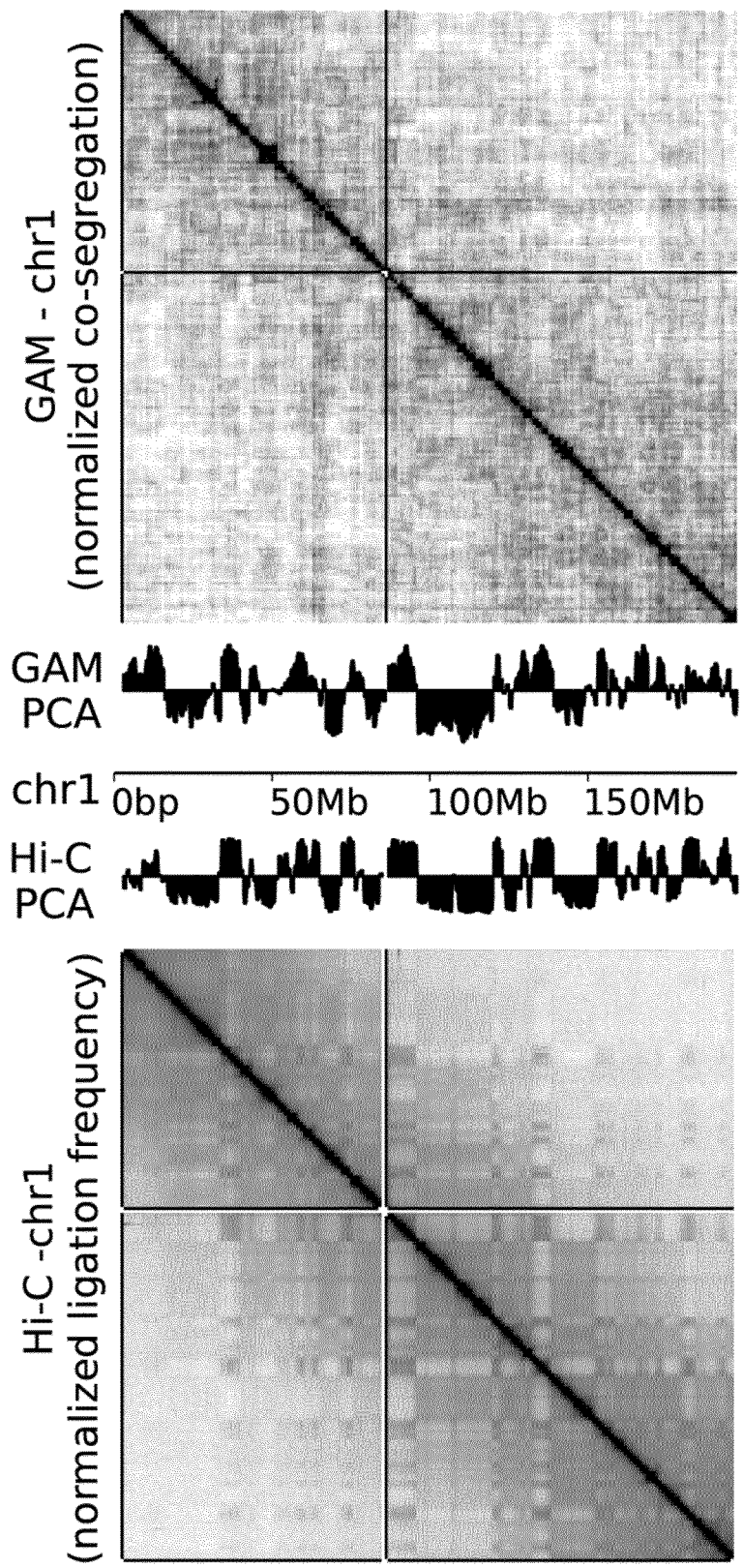
Figure 2E:
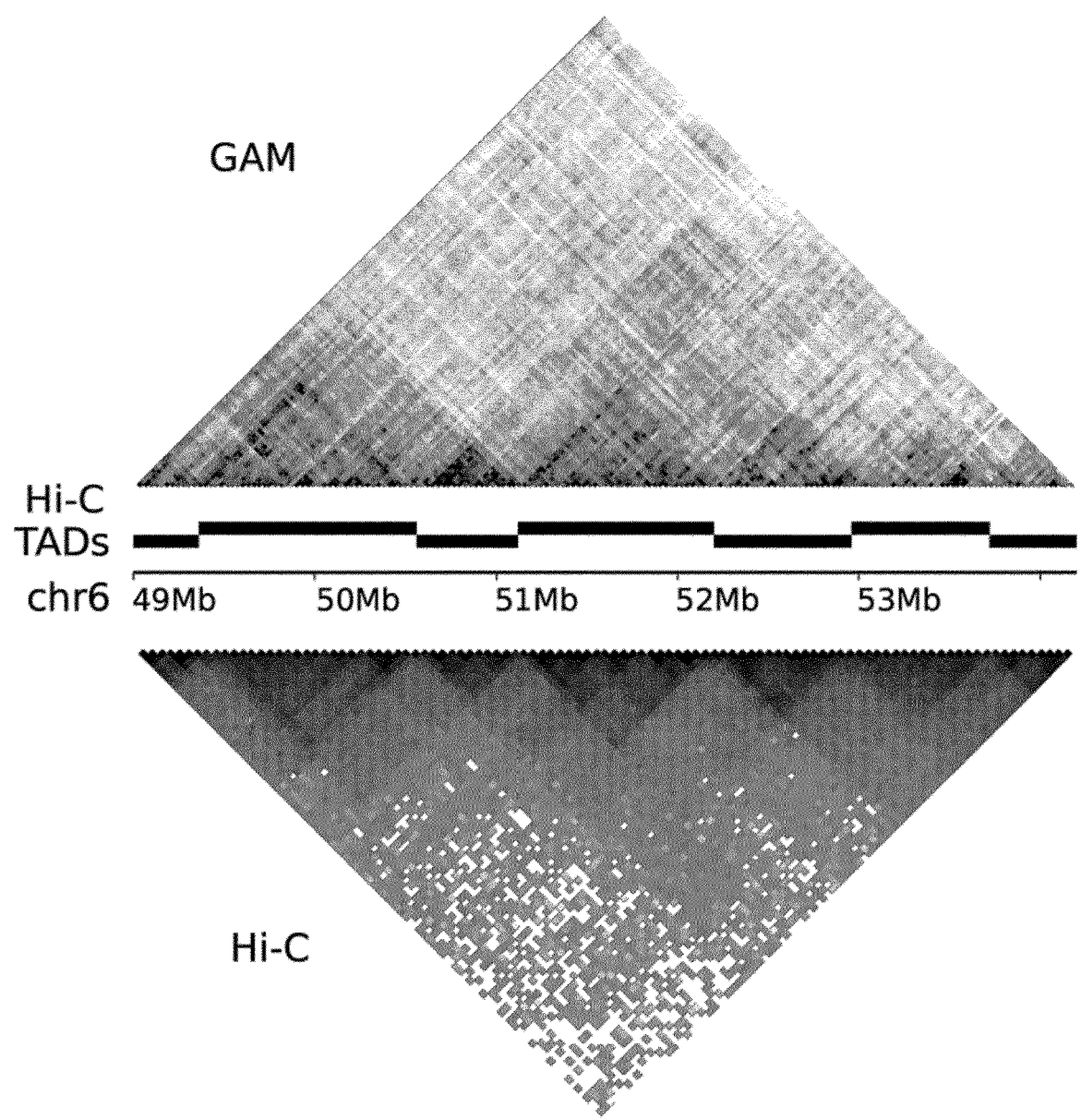

On the basis of the 408 NP dataset, loci in closer genomic distance are generally more frequently found in the same nuclear profiles, reflecting their closer distance in 3D space. GAM identified local preferences for chromatin contacts resembling previously described topological domains[7]. High co-segregation frequencies, indicating close physical proximity between loci, were also observed over very large genomic distances, up to the length of whole chromosomes (FIG. 2d, e). These interactions are less obvious in Hi-C datasets, which may be accounted for by any of the methodological differences between the two approaches (FIG. 4).

The GAM dataset was compared to a previously published Hi-C dataset from mESCs[7]. Visual comparisons revealed similar patterns in both datasets, particularly at smaller length scales (FIG. 2d,e). The Hi-C and GAM datasets were correlated at 1 Mb resolution with an overall correlation coefficient of 0.63 and pairwise correlations between individual chromosomes ranging from 0.43 to 0.71 (Spearman's rank correlation coefficient).

Previous Hi-C studies have used principle components analysis (PCA) to divide all genomic loci into two compartments based on their contacts[8]. The same approach was applied to identify compartments A and B in the GAM dataset (FIG. 2d). A good overlap of compartments was found, as 66% of 1 Mb windows are assigned to the same compartment in both GAM and Hi-C.

It was possible to visually identify highly self-interacting regions in the GAM dataset, which appeared to be similar to topological domains identified in Hi-C. Using a "moving-box" approach (FIG. 9a), a highly significant depletion of off-diagonal contacts was observed at previously identified TAD boundaries in mouse mESCs[7], confirming the presence of TADs in our dataset (FIG. 9b,c).

Extracting Interaction Probability (Frequency) from GAM Data with SLICE

DNA FISH studies have shown that chromatin folding is not homogeneous across cells: when interactions between two defined loci are examined directly under the microscope they are usually found in only a small sub-population of cells (Simonis M., et al. 2006. Nuclear organisation of active and inactive chromatin domains uncovered by chromosome conformation capture-on-chip (4C). Nat. Genet. 38 (11): 1348-54). Measures of co-localisation therefore represent population averages. The most biologically relevant measure of the strength of an interaction is held to be the fraction of the population of cells in which it occurs. When applied to populations of cells, conformation-capture based methods can identify loci which contact each other more frequently than expected, but they cannot access quantitative information about the frequency of these contacts in single cells.

In order to estimate the probability of an interaction occurring in an individual cell, a simple statistical model was developed by the inventors (SLICE computational platform, Statistical Inference of Co-segregation). It considers a mixed population of cells with either very closely (<100 nm) interacting or randomly folded loci pairs. The probability of interaction (Pi) which best describes the data is derived via a mathematical approach under a few simplifying assumptions: the nuclear volume is approximated by a sphere, interactions between alleles on different chromosomes are considered negligible[9] and the physical distance of two loci scales with their genomic distance. By assuming also that the majority of loci are non-interacting (the average interaction probability between loci at a given genomic distance is small), this scaling can be approximated via the mean co-segregation of all loci pairs at a given genomic distance. This type of modelling approach is very difficult to apply to Hi-C data, as the measured parameter (ligation frequency) is not a direct function of distance. Using further elaborations of this basic modelling approach, "leading" chromatin interactions may be dissected from "following" interactions, which occur due to the "leading" interactions of adjacent or nearby loci.

The model was applied to estimate interaction matrices between couples of loci. A statistically determined threshold was then applied to the dataset to retain only those interactions which are of a high enough frequency to give statistical confidence.

The SLICE model was used to identify all locus pairs that are more frequently positioned at short physical distances (<100 nm) in the nuclear space than expected for their genomic distance, and to estimate the frequency of locus interaction across the population of cells. 100 nm was chosen as a stringent distance for specific contacts, as recently measured by FISH (Williamson et al. 2014[58]). First, Pi was estimated for all possible pairs of loci on the same chromosome. The inventors then selected only those loci with significant interactions, meaning those that had a Pi larger than would be expected by chance.

The most significant interactions identified by SLICE correspond to locus pairs that most often co-segregate in the same slice (FIG. 13). For example, loci separated by 10 Mb co-segregate in 5.3 out of 408 NPs on average (1.29%). In contrast, significantly interacting loci separated by 10 Mb co-segregate in 10.1 out of 408 NPs (2.47%). This approach yields interaction matrices with a much less homogenous pattern than that of either Hi-C or GAM co-segregation matrices (FIG. 3b). The maps contain many more discrete spots, which may denote the specific bases (loci) of chromatin loops formed by interactions above the given threshold.

Having established this model, SLICE was used to estimate the detection efficiency at different resolutions. This approach suggested that the detection efficiency is 80% at 30 kb resolution, confirms 30 kb as the optimal resolution for this dataset and agrees well with the estimate of efficiency from comparing GAM to cryoFISH. The model was also used to consider the possibility of cutting more than one NP into each tube and of cutting sections at a range of different thicknesses. One NP per tube at a thickness of 220 nm is optimal for the present purposes, but may not be the best choice for studying organisms with much larger or smaller nuclei, where more than one NP, preferably 2, 3 or more, could be simultaneously analysed in a single tube.

To explore the nature of the interactions in the Pi matrices, the interaction probabilities of 30 kb windows containing distinct genomic elements were explored. The inventors used SLICE to identify 10 million high-confidence autosomal interactions (of 189 million possible intra-chromosomal pairs) of which 7.2 million involve genic regions (FIG. 12a). On average, 254 significant interactions were identified for each 30 kb window (±183 standard deviation; FIG. 12b). The number of interactions identified decreased with genomic distance, as expected, but spanned many tens of Mb. For example, of 4.5 million significant interactions involving active genes, 3 million span less than 60 Mb whilst 1.5 million span greater than 60 Mb FIG. 12c.

Previously published mRNA-seq and ChIP-seq[11] in mESCs were used to divide genes into three classes: active (FPKM>1), Polycomb repressed (FPKM<1, H3K27me3+ and/or H3Aub1+) or inactive (FPKM<1, no H3K27me3 or H3Aub1). A list of predicted enhancers was also included from a previous study[12]. All 30 kb windows which overlapped with a gene or enhancer were scored, and the number of significant interactions between different gene/enhancer categories was compared with random expectation. It was found that the interaction matrices contained an especially high number of significant interactions within and between the active gene and enhancer categories (FIG. 3c). For example, windows containing active genes made significantly more contacts to other active gene containing windows than a random control. In contrast, contacts between inactive genes occur as often as expected by chance. Similar results were also obtained by applying the enrichment analysis to the top 5% of interactions at each distance in linkage data without SLICE analysis (FIG. 12d), showing that they are an inherent feature of the GAM dataset. This underscores the efficacy of the GAM method for identifying interactions between regulatory elements and their cognate genes. The specificity with which GAM detects contacts between functional genomic regions shows that GAM is a powerful method for dissecting the role of specific SNPs and other genomic variants in genome folding and misregulated gene expression.

Detecting Interacting Triplets

GAM has the potential to capture many additional aspects of chromatin spatial organization genome-wide, such as multivalent chromatin interactions (interactions involving two, three or more genomic regions), radial distributions of chromosomes and sub-chromosomal regions and chromatin compaction. The inventors showed that the mESC-400 dataset already held enough information to reveal multivalent interactions between 3 or more loci. Detailed analyses of GAM statistics indicate that the current mESC-400 dataset allows detection of triplet contacts at the resolution of hundreds of kilobases, which corresponds to the chromatin organization level of TADs.

Pairwise contact matrices cannot distinguish simultaneous triplet interactions from independent pairwise events that do not occur in the same cell (FIG. 14a). To identify true triplet interactions, the inventors extended SLICE to consider triplets, and calculated the probability of a simultaneous, three-way interaction ($Pi_3$) at the same stringent spatial distance of <100 nm, for all possible combinations windows within three TADs (FIG. 14b). They considered only triplets of TADs that were connected by significant pairwise interactions and used 40 kb windows to match resolution with published TAD definitions (Dixon et al., 2012)(Methods). Then, candidate TAD triplets were ranked by the mean $Pi_3$ of their constituent 40 kb windows (FIG. 14c, FIG. 15a) and the top 5% TAD triplets with the highest interaction scores retained. These top 5% represent 170,000 highly interacting triplets across the mouse autosomes (FIG. 14d).

Given recent observations of significant clustering of the enhancer-bound Sox2 transcription factor in live mESC nuclei by single-molecule tracking experiments (Liu et al., 2014), it was tested whether TADs containing high densities of regulatory elements enriched for pluripotency transcription factor binding might be present within the top interacting TAD triplets. Therefore, all TADs were classified according to the presence of clustered enhancers with high-occupancy of the transcription factors Oct4, Sox2 and Nanog, which have been variously referred to as strong, stretch or super-enhancers (SEs) (Whyte et al., 2013). TADs that did not contain SEs were subdivided according to their level of transcription using a published Genome Run-On (GRO-seq) dataset (Min et al., 2011), as a measure of transcriptional activity (FIG. 14e). Remarkably, the inventors find that SEs, low-transcribed and highly-transcribed TADs are present in the set of most highly interacting triplets over a large range of genomic distances (for example, of 41982 triplets involving SEs, 19% span genomic distances of less than 30 Mb and 81% span between 30 and 116 Mb (FIG. 14f).

Figure 15A:
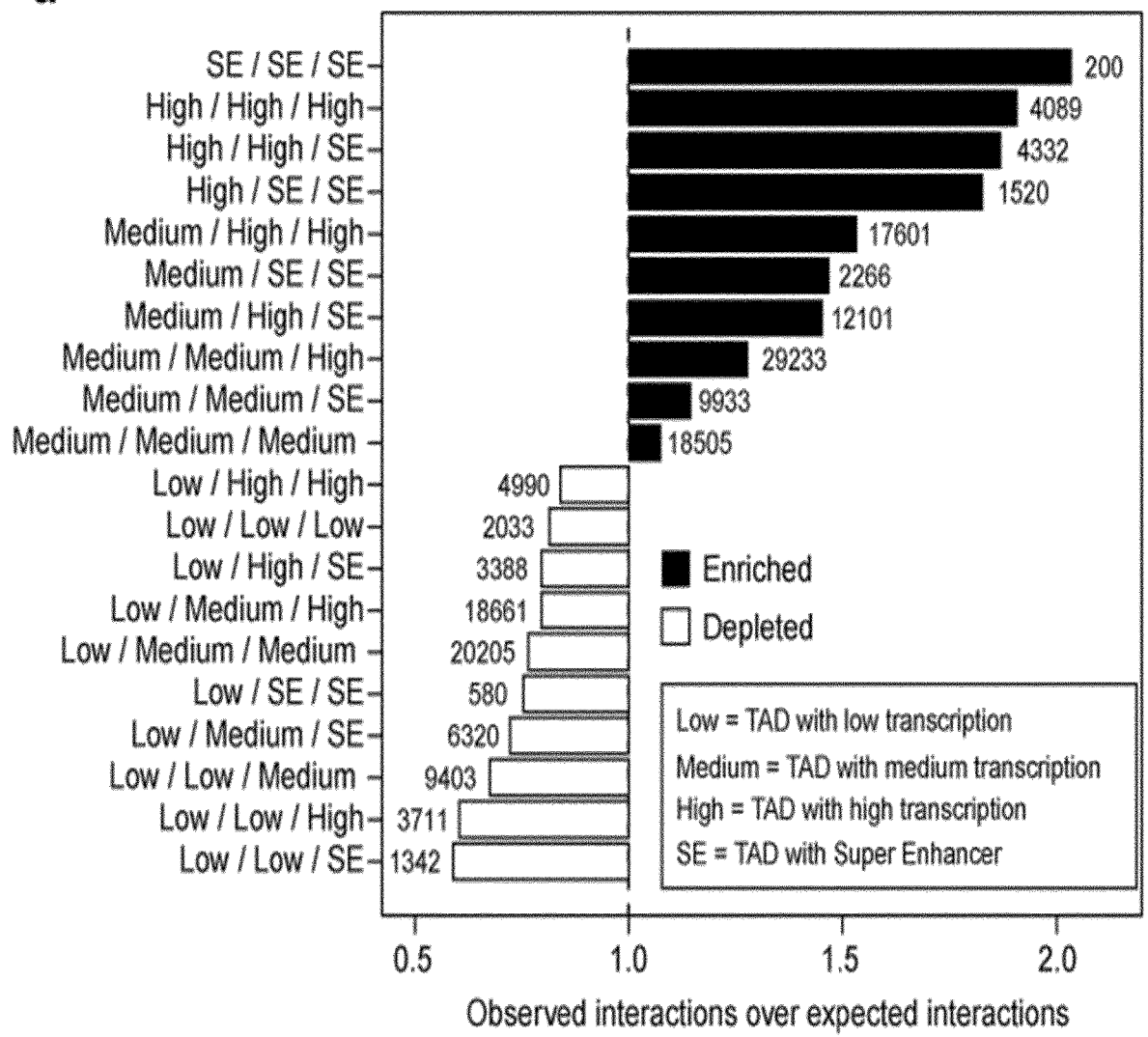

Next, the inventors tested whether interactions between specific classes were statistically enriched in the top interacting TAD triplets. Strikingly, they found that the most highly interacting TAD triplets are significantly enriched for triplets that connect three SE-containing TADs (FIG. 14g, FIG. 15a). This indicates that these arrays of enhancers clustered in the linear chromosome also come together in 3D space at high multiplicity in mESCs, a result that expands on recent observations of nuclear clustering of chromatin-bound Sox2 by single-molecule imaging of live mESCs (Liu et al., 2014) and of pairwise contacts between super-enhancers detected by Hi-C (Ing-Simmons et al., 2015). Remarkably, the inventors also find enrichments for triplets formed between highly transcribed TADs, or combinations of SE and highly-transcribed TADs, consistent with previous observations that active genes co-localize (Pombo et al., 1999; Osborne et al., 2004). In contrast, triplets composed of the least transcribed TADs occur less often than expected by chance, which is likely a consequence of their preferential association with the nuclear lamina (Peric-Hupkes et al., 2010) (FIG. 14h). Interestingly, it was observed that SE and high-transcription TADs which overlap or are close to lamina-associated domains (LADs) are also involved in fewer three-way interactions, indicating that lamina association of adjacent TADs restrains active regions and restricts their access to more central enhancer clusters (FIG. 14i).

These analyses identify windows overlapping enhancers and active genes as major determinants of chromosome folding. To examine whether interactions might be nucleated by the active genes and/or enhancers inside interacting windows, the inventors calculated normalized linkage at 5 kb resolution (FIG. 15b). They found that 5 kb windows overlapping enhancers, promoters (TSS) or the transcription end sites (TES) of active genes have higher average linkage to prominently interacting Active 30 kb windows than 5 kb windows 15 kb upstream or downstream of these features. This enrichment was also seen for interactions with Enhancer 30 kb windows, but not for Active windows that are not interacting at 30 kb resolution (FIG. 15c). Similarly, average three-way linkage between SE TADs forming a top triplet was found to be enriched for the 40 kb window directly overlapping the super-enhancer compared to the 40 kb windows 120 kb upstream or downstream (FIG. 15d,e).

Using GAM to Explore Radial Positioning and Compaction

GAM holds the power to explore additional spatial features of chromatin organization in the 3D nuclear space. The inventors exploited two stereological applications of the GAM method using the mESC-400 dataset. As a result of the random orientation of sectioning with respect to the nucleus, the DNA content of NPs originated from different latitudes of the nucleus can be used to estimate radial distributions of genomic regions. For example, NPs cut through nuclei close to their periphery contain, by definition, a smaller proportion of the nuclear volume (or DNA content; Branco et al., 2008) than equatorial NPs (FIG. 16a). Therefore, the percentage of the genome covered by each NP could be used as a proxy for its latitude relative to the most equatorial NPs. Indeed, the inventors find that the frequency with which chromosomes are detected in smaller NPs correlates with their radial position (as previously measured for five chromosomes in mESCs (Mayer et al., 2005)), with lower average DNA content corresponding to more peripheral positions (FIG. 16b).

The inventors further explored a more local feature of chromatin folding, which can in principle also be assessed by GAM. The inventors reasoned that de-condensed genomic loci will occupy larger volumes (or adopt more elongated conformations) than more condensed loci. More de-condensed loci should therefore be intersected more frequently (and be detected more frequently in randomly-oriented nuclear profiles) than smaller or more spherical loci (FIG. 16c). De-condensed chromatin ought to be more accessible to enzymatic cleavage, e.g. using DNAse I, and the inventors found that the coverage of 30 kb windows in a published DNase-seq dataset correlates with their detection frequency in the GAM mESC-400 dataset (Spearman's r=0.47, p ≤$10^{-6}$; FIG. 16d). Transcriptional activity has been shown to correlate with chromatin de-condensation for individual loci, or globally after overexpression of structural proteins. The inventors further find that the transcriptional activity of 30 kb genomic windows as measured by GRO-seq coverage (Min et al., 2011) is positively correlated with their detection frequency in single NPs (Spearman's r=0.27, p ≤$10^{-6}$; FIG. 16d). These results allow them to report for the first time a genome-wide association between transcription levels and chromatin volume (condensation) at 30 kb resolution in mouse ESCs. These analyses already illustrate the potential of GAM to investigate features of nuclear organisation which have so far remained inaccessible and unexplored on a genome-wide scale.

Discussion

GAM is a novel, ligation-free method for capturing chromatin contacts in an unbiased manner, independent of all other current technologies used to measure 3D genome topology and positioning. GAM uncovers a complex organization of the 3D structure of chromatin in mESCs, where functional genomic regions underlie specific chromatin contacts. Especially notable is the enrichment for pairwise chromatin interactions within and between enhancer elements and transcribed regions. The identification of abundant three-way interactions between TADs, where multiple strong enhancers and highly transcribed regions associate simultaneously in the same nucleus, reveals that regulatory elements form higher-order contacts across large genomic regions. In contrast, proximity to the nuclear lamina appears to curb the formation of higher complexity contacts involving highly transcribed TADs, either by restricting access to more central enhancer clusters or by limiting the surface available for the formation of multiple contacts.

Importantly, the results obtained by GAM independently verify findings made using other methods, including the identification of preferentially self-associating genomic regions (TADs) by 5C/Hi-C and the observed clustering of chromatin bound by the transcription factor Sox2 (an enhancer marker) in live-cell imaging. At the same time, the genome-wide scale of GAM and the integrated collection of different aspects of positional information (contacts, radial positioning and compaction) add new analytical opportunities that the previous techniques could not provide.

The development of SLICE provides a general statistical model for GAM that can extract quantitative information about chromatin interactions from GAM datasets. This permits identification of prominent pairwise and three-way contacts taking into account genomic distance. With larger GAM datasets, SLICE can be extended to integrate different nuclear or chromosome shapes or volumes, association to the nuclear periphery and other features of nuclear architecture, to enhance the detection of specifically interacting chromatin regions at high resolution.

Larger GAM datasets containing several thousand NPs should allow exploration of additional analytical possibilities afforded by GAM, including higher resolution quantification of pairwise, triplet and higher multiplicity contacts, volume and radial positioning genome-wide, and of the inter-dependency of different contacts (FIG. 4). Importantly, GAM can direct these analyses to rare cell types specifically selected by microdissection from precious tissue samples, for example those obtained from biopsies of individual patients. In addition, GAM should be compatible with simultaneous detection of specific chromatin contacts and active transcription in single cells (Dey et al., 2015. Integrated genome and transcriptome sequencing of the same cell. Nature Biotechnology, 33(3): 285-289), which will be crucially important for dissecting causal relationships.

In summary, GAM adds a powerful new tool to the genome biologist's repertoire and significantly expands our ability to finely dissect three dimensional chromatin structures, rendering many previously unanswerable questions experimentally tractable in a wider range of model systems, cell types and valuable human samples. GAM's unique suitability to study chromosome folding in rare cell types will be invaluable in dissecting the role of natural sequence variation in human disease.

Methods

Cell Culture

The mouse ES cells (mESCs) used for this example were the 46C line[13], a Sox1-GFP derivative of E14tg2a and gift of Domingos Henrique (Institute of Molecular Medicine, Lisbon, Portugal). mESC culture was carried out as previously described[14]. Briefly, cells were grown at 37° C. in a 5% $CO_2$ incubator in Glasgow Modified Eagles Medium, supplemented with 10% fetal bovine serum, 2 ng/ml LIF and 1 mM 2-mercaptoethanol, on 0.1% gelatin-coated dishes. Cells were passaged every other day. After the last passage 24 h before harvesting, mESCs were re-plated in serum-free ESGRO Complete Clonal Grade medium (Millipore Inc.). Other cells may be used instead.

Preparation of Cryosections

The cells were prepared for cryosectioning as described previously[2]. Briefly, cells were fixed in 4% and 8% paraformaldehyde in 250 mM HEPES-NaOH (pH 7.6; 10 min and 2 h, respectively), pelleted, embedded (2 h) in 2.1 M sucrose in PBS and frozen in liquid nitrogen. Frozen cells may be stored in liquid nitrogen indefinitely. Ultrathin cryosections were cut using an UltraCut UCT 52 ultracryomicrotome (Leica, Milton Keynes, UK) at around 220 nm thickness. Sections were captured in sucrose solution drops and transferred to 1 mm-thick PEN membrane covered glass slides for laser microdissection (Leica, Milton Keynes, UK). To remove the sucrose embedding medium, slides were washed (3×) with 0.2 μm filtered molecular-biology grade PBS (5 min each), then (3×) with filtered ultra-pure $H_2O$ (5 min each) and left to dry for 15 min. In a few cases, the third PBS wash was substituted for a 5 min stain with molecular-biology grade propidium iodide (1 μg/ml in PBS).

Isolation of Nuclear Profiles

Individual NPs were isolated from the cryosection by laser microdissection using a PALM Microbeam Laser microdissection microscope (Carl Zeiss, Jena, Germany). Nuclei were identified under bright-field imaging and the laser was used to cut the slide membrane surrounding each nucleus. Cut NPs were then catapulted using the Laser Pressure Catapult into a PCR Cap Strip filled with opaque adhesive material. One well in each strip of eight was left empty and taken through the WGA process as a negative control. Five of these negative controls were also used to make sequencing libraries for quality control purposes (FIG. 6a).

Whole Genome Amplification

Whole genome amplification using the WGA4 kit (Sigma) was carried out with minor modifications to the previously described protocol[5]. Water (13 μl) was added to each of the upturned PCR lids containing an isolated NP (in this and the following steps, volumes of buffer have been increased relative to the supplier's protocol in order to cover the entire inner surface of the PCR cap lid). PK mastermix (containing 8 μl proteinase K solution, 128 μl 10× single cell lysis and fragmentation buffer) was added to each lid (1.4 μl/lid), and 1 μl of human genomic DNA was added to a single lid without a nuclear profile to act as a positive control. The lids were pressed into a 96-well PCR plate and incubated upside down at 50° C. for 4 h.

After incubation, the PCR plate was left to cool at room temperature for 5 min, before it was inverted and centrifuged at 800×g for 3 min. The plate was heat-inactivated at 99° C. for 4 min in a PCR machine and cooled on ice for 2 min. 2.9 μl 1× single cell library preparation buffer and 1.4 μl library stabilisation solution were added to each well and the plate was incubated at 95° C. for 4 min, before cooling on ice for 2 min. 1.4 μl of library preparation enzyme was added to each reaction, then the plate was incubated on a PCR machine at 16° C. for 20 min, 24° C. for 20 min, 37° C. for 20 min and finally 75° C. for 5 min.

After WGA library preparation, the PCR plate was centrifuged at 800×g for 3 min. 10× amplification master mix (10.8 µl), water (69.8 µl) and WGA DNA Polymerase (7.2 µl) were added to each well and the sample was PCR amplified using the program provided by the supplier.

Whole genome amplification was generally carried out in a single day, but in some cases samples were stored overnight at −20° C. midway through the protocol, without detectable differences in DNA detection in controlled tests of this variable.

Preparation of Libraries for High-Throughput Sequencing

WGA amplified DNA was purified using a Qiagen MinElute PCR Purification Kit and eluted in 50 µl of the provided elution buffer. The concentration of each sample was measured by PicoGreen quantification. Sequencing libraries were then made using either the Illumina TruSeq DNA HT Sample Prep Kit or the TruSeq Nano DNA HT kits. In both cases, samples were made up to 55 µl with resuspension buffer. For the DNA HT kits, a maximum of 1.1 µg DNA was added to each reaction, whereas for the Nano kits, a maximum of 200 ng was used.

Libraries were prepared according to the manufacturer's instructions. For DNA HT kits, samples were size selected to 300-500 nucleotides using a Pippin Prep machine (Sage Science, Beverly, Mass., USA) with EtBr-free 1.5% agarose cassettes. Samples prepared with the Nano kits were selected to 350 nucleotide size using the bead based selection protocol.

After library preparation, library concentrations were estimated using a Qubit 2.0 fluorometer (Thermo Fisher Scientific, Waltham, Mass., USA) and libraries were pooled together in batches of 96. Each library pool was sequenced in a single end, 100 bp run on two lanes of an Illumina HISEQ machine in rapid-run mode. Due to the presence of the 30 bp WGA adaptor at both ends of every read, the first 30 bp of each run were performed without imaging the flow cell (these are known as dark cycles) using a custom run recipe provided by Illumina.

High-Throughput Sequencing Data Analysis

Reads were mapped to the mm9 assembly of the *M. musculus* genome using Bowtie2[15]. Reads which did not map uniquely, which had quality scores of less than 20 or which were PCR duplicates were removed.

Calling Positive Windows in GAM Samples

The mouse genome was split into equal size windows using bedtools[16], and bedtools multibamcov was used to calculate the number of reads in each nuclear profile which overlapped each genomic window. The Pandas and NumPy python packages[17] were used to calculate a histogram from the number of reads overlapping each window, and the fmin function from SciPy was used to fit a negative binomial distribution (representing sequencing noise) and a lognormal distribution (representing true signal) to the depth histogram. Using the parameters of the fit for the binomial distribution, a threshold number of reads x was determined, where the probability of observing more than x reads mapping to a single genomic window was less than 0.001. Such a threshold was thus independently determined for each sample, and windows were scored as positive if the number of sequenced reads was greater than the determined threshold.

Sample Quality Control

In order to exclude low-quality datasets from the analysis, a number of quality metrics was measured for each sample. The percentage of mapped reads and percentage of non-PCR duplicate reads was measured by a custom python script. Sequencing quality metrics were determined for each sample using FastQC (bioinformatics.babraham.ac.uk/projects/fastqc) and a custom script was used to extract the average sequencing quality score per base, the number of dinucleotide repeats and the number of single nucleotide repeats from the FastQC output file. Possible sample contamination was checked using Fastq-screen (bioinformatics.babraham.ac.uk/projects/fastq_screen). Thin sections through the nucleus were expected to contain a characteristic proportion of the whole genome, organized in clusters and not containing all autosomal chromosomes. Therefore, a custom python script was developed to measure the total number of windows scored positive, the number of positive windows immediately adjacent to another positive window and the number of positive chromosomes for each sample. All of these quality metrics were fed into a Principle Components Analysis and looked for components that best discriminated the five negative controls. This analysis determined that percentage of mapped reads was the most predictive metric. Negative controls had a maximum of 2% mapped reads, so all samples with <15% mapped reads were excluded as a conservative threshold.

Calculating Sequencing Depth Saturation Point

NumPy was used to erode reads from the matrix of read depths per window per sample. Thirteen new matrices were produced with erosion rates from 10% to 95%, and positive windows were called for each of the eroded datasets. Each sample was compared across the eroded datasets to obtain a saturation curve, where the number of positive windows identified is plotted against the percentage of reads remaining after erosion. Samples were classified as saturated or unsaturated by splitting the saturation curves into two parts and comparing a linear regression of the two parts to a linear regression on the whole curve. The putative saturation point was defined as the point where the mean of the R-squared values from the two-part fit was highest. Samples were classified as saturated if the gradient of the second of the two parts was less than the gradient of the first (i.e. if the number of additional positive windows identified increased more slowly at higher read depths) and if the mean R-squared of the two-part fit was more than 0.25 greater than the R-squared of the linear fit against the whole curve (i.e. if the curve differed significantly from a straight line).

Fluorescence In Situ Hybridization

DNA FISH was performed as previously described[18]. Mouse ES-OS25 cells (kindly provided by W. Bickmore) were grown as previously described[36]. The HoxB13, HoxB1-3 and Skap1 loci were detected with fosmid probes (G135P6799B3, G135P67637D6 and G135P60674A4, respectively). Fosmid probes were obtained from BACPAC Resources (California, USA). The specificity of fosmid probes was confirmed by PCR using specific primers (not shown). Probes were labelled with digoxigenin-11-dUTP, fluorescein-12-dUTP or tetramethyl-rhodamine-5-dUTP by nick translation (Roche), and separated from unincorporated nucleotides using MicroBioSpin P-30 chromatography columns (BioRad, Hertfordshire, UK). The signal of rhodamine-labelled probes was amplified with rabbit anti-rhodamine antibodies (2 h; 1:500; Invitrogen) and Cyanine3-conjugated donkey antibodies against rabbit IgG (1 h; 1:1000; Jackson ImmunoResearch Laboratories). Probes labelled with digoxigenin were detected with sheep anti-digoxigenin Fab fragments (2 h; 1:200; Roche) and AlexaFluor555 donkey antibodies against sheep IgG (1 h; 1:1000; Invitrogen). Probes labelled with FITC were detected with mouse antibodies against FITC (1 h, 1:500;

Jackson ImmunoResearch Laboratories) and AlexaFluor488 donkey antibodies against mouse IgG (1 h, 1:1000; Invitrogen). Nuclei were stained with DAPI and coverslips were mounted with VectaShield (Vector Laboratories) before imaging. Images were acquired on a confocal laser-scanning microscope (Leica TCS SP5; 63× oil objective, NA 1.4) equipped with a 405 nm diode, and Argon (488 nm), HeNe (543 nm) and HeNe (633 nm) lasers, using pinhole equivalent to 1 Airy disk. Images from different channels were collected sequentially to prevent fluorescence bleedthrough. Raw images (TIFF files) were merged in ImageJ and contrast stretched without thresholding in Adobe Photoshop.

Calculation of Linkage Matrices

To calculate the linkage matrix for a defined genomic region, the genomic windows from each sample that overlap the region of interest were first extracted. For all possible pairs of windows overlapping the window, the co-segregation is the number of nuclear profiles in which both windows are scored as positive divided by the total number of nuclear profiles.

Linkage disequilibrium (D) and normalized linkage disequilibrium (D') are calculated as previously defined[6]. In short, the linkage between two genomic windows A and B is defined as the co-segregation of A and B (see above) minus the product of their marginal detection frequencies. The marginal detection frequency of A is simply the number of nuclear profiles in which A is detected divided by the total number of nuclear profiles. The normalized linkage between two genomic windows A and B is defined as the linkage of A and B divided by the maximum possible linkage between A and B (Dmax). If linkage >0, Dmax is calculated as $\min((\text{marg}(A)*(1-\text{marg}(B))), (\text{marg}(B)*(1-\text{marg}(A))))$, where marg(A) is the marginal detection frequency of A. If linkage <0, Dmax is calculated as $\min((\text{marg}(A)*\text{marg}(B)), ((1-\text{marg}(A))*(1-\text{marg}(B))))$.

Herein, marg(A) is the marginal detection frequency of A. Heatmaps of linkage between all regions on the same chromosome were calculated from linkage matrices L(i,j) where each entry is the normalized linkage of i and j. These calculations can be trivially extended to consider any number of loci. For example, linkage between three loci is calculated as the co-segregation of A, B and C minus the products of the marginal detection frequencies of A, B and C.

Defining Compartments A and B From Interaction Datasets

Compartments A and B were calculated for GAM and Hi-C according to the previously published method[8,23]. Each chromosome is represented as a matrix O(i,j) where each entry records the observed interactions between locus i and locus j. A new matrix E(i,j) was generated where each entry is the mean number of interactions for all positions in matrix O with the same distance between i and j. O was divided by E to give K(i,j) a matrix of observed over expected values. The final matrix C(i,j) was then calculated, where each position is the correlation between column i and column j of matrix K. A principle components analysis was conducted on the correlation matrix C and the three components that explain the most variance were then extracted. Of these three components, the one with the best correlation to GC content is used to define the A and B compartments.

Estimation of Bias in GAM/Hi-C Matrices

To compare biases between GAM and Hi-C, 50 kb genomic window were assigned to one of ten equal groups based on their average GC content. Observed over expected (OE) matrices were then calculated for each chromosome from both GAM and Hi-C data at 50 kb resolution (see "Defining A and B compartments from GAM and Hi-C datasets"). For each combination of two GC content groups, the mean OE values for contacts between windows in the two groups was taken, resulting in a heatmap of mean OE values by GC content. The same approach was then repeated, stratifying 50 kb windows by average mappability, the number of HindIII sites they contained, their mean replication time or the percentage of each 50 kb window overlapping annotated genomic repeats.

Identification of Topologically Associating Domains

The list of topologically associating domain boundaries was obtained from a previous study in mESCs[7]. The mean normalized linkage disequilibrium was measured in a 3×3 box moved at an offset of two windows from the diagonal of the linkage matrix as a measure of off-diagonal interactions. By comparing the off-diagonal interactions at the previously described topological domain boundaries with the off-diagonal interactions 150 kb upstream and downstream of the domain boundary, the depletion of off-diagonal interactions was measured for these previously defined boundaries in the dataset. The statistical significance of this depletion was assessed by comparing the observed off-diagonal depletion with the depletion measured from 5000 randomly shuffled sets of TADs.

Extracting Interaction Probabilities from GAM Data Using the SLICE Method

The ratio between the number of tubes containing two loci and the number of tubes containing at least one member of a locus pair was measured for all pairs of 30 kb windows in the mouse genome. The average of this ratio over all pairs of loci at the same genomic distance was then taken, calculated separately for each chromosome. By comparing this genomic average to the observed ratio for each individual locus pair, it was possible to identify pairs of loci which co-segregate more frequently than the average pair of loci at the same distance on the same chromosome. A mathematical model was used to estimate the fraction of cells which would need to have a close (<100 nm) interaction in order to give the observed value of the ratio. Then any loci pairs in which the observed ratio was within the 95$^{th}$ percentile of the ratio expected for non-interacting loci at that genomic distance were discarded.

Analysis of TADs Interacting in Triplets

To identify triplets of TADs interacting simultaneously, sets of three TADs were first identified where all three TADs displayed significant pairwise interactions identified by SLICE. For all such triplets, the Pi$_3$ of all the 40 kb windows making up the TADs were calculated using SLICE. 40 kb windows were used here as the TAD positions in Dixon et al. (2012) are given at 40 kb resolution. Finally, all triplets were ranked by their mean Pi$_3$ and the top 5% selected for enrichment analysis. TADs were assigned as SE TADs if they overlapped any previously identified super-enhancers (SEs; Whyte et al., 2013). TADs not overlapping SEs were classified as low-transcription or high-transcription if they had GRO-seq coverage below the first or above the third quartile respectively. TADs in the middle two quartiles of coverage were classified as medium-transcription. Enrichment was calculated as the observed number of each TAD triplet class (e.g. SE/SE/SE) divided by the mean over 500 randomly permuted lists of TAD triplets, and was called as significant if the observed count was greater than or smaller than all of the randomly permuted values.

To analyse the impact of nuclear lamina association on triplet formation, a list of LAD regions in mESC cells (Peric-Hupkes, D. et al. Molecular Maps of the Reorganization of Genome-Nuclear Lamina Interactions during Differentiation. Mol. Cell 38, 603-613 (2010)) was used. TADs were categorized into most (top 15%) and least (bottom 15%) triplet forming in accordance to the number of triplets in the top 5% that contained the TAD. The distances of TADs in each category to LADs were calculating using the closestBED tool (Quinlan et al., 2010).

Analysis of Average Linkage at 5 kb Resolution

To define if chromatin interactions of 30 kb windows are centred on features they comprise (TSS, TES and enhancers), each 30 kb window overlapping exactly one enhancer or TSS/TES of an active gene (FPKM>1; length >120 kb), but no other gene or enhancer, was subdivided into 6 non-overlapping 5 kb windows. Subsequently, normalized linkage disequilibrium with other interacting "Enhancer" or "Active" 30 kb windows (SLICE p-value=0.05 of the harbouring 30 kb window to the interacting 30 kb window) was calculated for the 5 kb window overlapping the feature of interest ±three 5 kb windows upstream/downstream. This resulted in a matrix in which each row represents a single interaction between two 30 kb windows and the columns represent the linkage for the 5 kb window of interest ±three 5 kb windows upstream/downstream. To normalize for distance effects, each row was divided by its own mean. Next, the mean of each column was taken to obtain the average linkage at each distance from the 5 kb window of interest. Finally, these mean values were divided by the mean of the first and last column to obtain the average enrichment at the TSS relative to 15 kb upstream/downstream. As a control, non-interacting (SLICE p-value >0.05) 30 kb window pairs comprising the same features (enhancer, TSS, TES) were used. To ensure similar distance distributions, the true interactions were sorted into 10 bins by their genomic distance and the control group was randomly reduced so that bin counts for each genomic distance range were the same.

Analysis of Average Three-Way Linkage at 40 kb Resolution

To define if triplet chromatin contacts between three windows all containing super-enhancers ("SE/SE/SE") are centred over the comprised super enhancers, all TADs containing a single SE that was less than 40 kb in length were selected. A 40 kb window was centred over the SE as well as ±three 40 kb windows upstream/downstream. TADs where the TAD boundary fell within any of these 40 kb windows were discarded. Next, based on all "SE/SE/SE" triplets that involved the selected TADs, the mean three-way normalized linkage disequilibrium between the SE-containing 40 kb windows and all 40 kb windows in the two partner SE TADs were calculated. This was repeated for the 40 kb windows upstream/downstream of the selected SE-containing 40 kb window. As described above for pairwise average linkage, each resulting row was divided by its mean, then the mean taken for each column and finally the result divided by the average of the first/last column. The whole process was repeated for the same set of selected SE-TADs and their partner highly-transcribed (High) TADs in the list of top triplets corresponding to "SE/High/High" TADs and for non-interacting "SE/SE/SE" triplet TADs which spanned the same genomic distances (control).

Estimation of Chromosome Radial Position from GAM Data

As an approximation of the latitude of each NP relative to centre of the nucleus, the coverage of each chromosome was calculated as the mean number of reads per Mb for each NP. For each chromosome, every NP in which that chromosome was in the top quartile of coverage was taken and the percentage of all genomic 1 Mb windows that were positive calculated. The percentage coverage of an NP is a measure of its radius (Branco et al., 2008), and therefore the mean percentage coverage of NPs containing a given chromosome is a measure of the preference of that chromosome to appear in NPs with a large radius (as is expected of more centrally positioned chromosomes). The inventors correlated the mean percentage coverage of NPs containing chromosomes 1,2,9,11 and 14 with their radial position, previously measured in Mayer et al. (2005), and found a tendency for more peripheral chromosomes to be found in NPs with lower genomic coverage.

Estimation of Locus Volume from GAM Data

The mouse genome was divided into 30 kb windows and the number of NPs where each window was detected calculated (its detection frequency). This value was correlated with the mean coverage of a previously published GRO-seq dataset (Min et al., 2011) and with the mean coverage of DNAse-seq (a measure of chromatin openness at the nucleosome level; Yue, F. et al. 2014. Nature 515, 355-364). over each 30 kb window

REFERENCES

1. Dear, P. H. & Cook, P. R. Happy mapping: a proposal for linkage mapping the human genome. *Nucleic Acids Res.* 17, 6795-807 (1989).
2. Guillot, P. V, Xie, S. Q., Hollinshead, M. & Pombo, A. Fixation-induced redistribution of hyperphosphorylated RNA polymerase II in the nucleus of human cells. *Exp. Cell Res.* 295, 460-8 (2004).
3. Branco, M. R. & Pombo, A. Intermingling of chromosome territories in interphase suggests role in translocations and transcription-dependent associations. *PLoS Biol.* 4, e138 (2006).
4. Emmert-Buck, M. R. et al. Laser capture microdissection. *Science* 274, 998-1001 (1996).
5. Baslan, T. et al. Genome-wide copy number analysis of single cells. *Nat. Protoc.* 7, 1024-41 (2012).
6. Lewontin, R. C. The Interaction of Selection and Linkage. I. General Considerations; Heterotic Models. *Genetics* 49, 49-67 (1964).
7. Dixon, J. R. et al. Topological domains in mammalian genomes identified by analysis of chromatin interactions. *Nature* 485, 376-380 (2012).
8. Lieberman-Aiden, E. et al. Comprehensive mapping of long-range interactions reveals folding principles of the human genome. *Science* 326, 289-93 (2009).
9. Khalil, A. et al. Chromosome territories have a highly nonspherical morphology and nonrandom positioning. *Chromosome Res.* 15, 899-916 (2007).
10. Mateos-Langerak, J. et al. Spatially confined folding of chromatin in the interphase nucleus. *Proc. Natl. Acad. Sci. U.S.A.* 106, 3812-7 (2009).
11. Brookes, E. et al. Polycomb Associates Genome-wide with a Specific RNA Polymerase II Variant, and Regulates Metabolic Genes in ESCs. *Cell Stem Cell* 10, 157-70 (2012).
12. Chen, C., Morris, Q. & Mitchell, J. a. Enhancer identification in mouse embryonic stem cells using integrative modeling of chromatin and genomic features. *BMC Genomics* 13, 152 (2012).
13. Ying, Q.-L., Stavridis, M., Griffiths, D., Li, M. & Smith, A. Conversion of embryonic stem cells into neuroectodermal precursors in adherent monoculture. *Nat. Biotechnol.* 21, 183-6 (2003).
14. Abranches, E. et al. Neural differentiation of embryonic stem cells in vitro: a road map to neurogenesis in the embryo. *PLoS One* 4, e6286 (2009).
15. Langmead, B. & Salzberg, S. L. Fast gapped-read alignment with Bowtie 2. *Nat. Methods* 9, 357-9 (2012).

16. Quinlan, A. R. & Hall, I. M. BEDTools: a flexible suite of utilities for comparing genomic features. *Bioinformatics* 26, 841-2 (2010).
17. Oliphant, T. E. Python for Scientific Computing. Comput. Sci. Eng. 9, 10-20 (2007).
18. Ferrai, C. et al. Poised transcription factories prime silent uPA gene prior to activation. *PLoS Biol.* 8, e1000270 (2010).
19. O'Sullivan, J. M., Hendy, M. D., Pichugina, T., Wake, G. C. & Langowski, J. The statistical-mechanics of chromosome conformation capture. *Nucleus* 4, 390-8 (2013).
20. Sexton, T. et al. Three-dimensional folding and functional organization principles of the Drosophila genome. *Cell* 148, 458-72 (2012).
21. Gavrilov, A. a et al. Disclosure of a structural milieu for the proximity ligation reveals the elusive nature of an active chromatin hub. *Nucleic Acids Res.* 41, 3563-75 (2013).
22. Yaffe, E. & Tanay, A. Probabilistic modeling of Hi-C contact maps eliminates systematic biases to characterize global chromosomal architecture. *Nat. Genet.* 1-9 (2011). doi: 10.1038/ng.947
23. Imakaev, M. et al. Iterative correction of Hi-C data reveals hallmarks of chromosome organization. *Nat. Methods* 9, 999-1003 (2012).
24. Hu, M. et al. HiCNorm: removing biases in Hi-C data via Poisson regression. *Bioinformatics* 28, 3131-3133 (2012).
25. Kruse, K., Sewitz, S. & Babu, M. M. A complex network framework for unbiased statistical analyses of DNA-DNA contact maps. *Nucleic Acids Res.* 41, 701-710 (2012).
26. Van Berkum, N. L. et al. Hi-C: a method to study the three-dimensional architecture of genomes. *J. Vis. Exp.* e1869 (2010). doi:10.3791/1869
27. Barbieri, M. et al. Complexity of chromatin folding is captured by the strings and binders switch model. *Proc. Natl. Acad. Sci. U.S.A.* 109, 16173-8 (2012).
28. Pombo A. 2003. Cellular genomics: which genes are transcribed when and where? Trends Biochem. Sci. 28, 6
29. Belmont A. S., 2014. Large scale chromatin organization: the good, the surprising, and the still perplexing. Curr Op Cell Biol 26, 69
30. Chen et al., 2014. Nano-Dissection and Sequencing of DNA at Single Sub-Nuclear Structures. Small 10:3267.
31. Luǔiǔ V., et al., 2013. Cryo-electron tomography: The challenge of doing structural biology in situ. J Cell Biol 202 (3), 407.
32. Deng et al., 2014. Manipulating nuclear architecture. Curr Op Genet Dev. 25:1-7.
33. Chetverin A B, Chetverina H V, 2008. Molecular colony technique: a new tool for biomedical research and clinical practice. Prog. Nucleic Acid Res. Mol. Biol 82:219-255.
34. Pombo A, et al. 1999. Bridging the resolution gap: Imaging the same transcription factories in cryosections by light and electron microscopy. J. Histochem. Cytochem. 47, 471-480.
35. Maxwell S, et al. 2005. Pitx3 regulates tyrosine hydroxylase expression in the substantia nigra and identifies a subgroup of mesencephalic dopaminergic progenitor neurons during mouse development. Dev. Biol., 282(2):467-479
36. Stock J K, et al. (2007) Ring1-mediated ubiquitination of H2A restrains poised RNA polymerase II at bivalent genes in mouse ES cells. Nat. Cell Biol. 9: 1428-35
37. Gavrilov A A, et al. 2014. Quantitative analysis of genomic element interactions by molecular colony technique. Nucl. Acids Res. 42 (5):e36
38. Maeburn K J, et al. 2009. Disease-specific gene repositioning in breast cancer. J. Cell Biol. 187(6):801-12;
39. Kubben N, et al. 2012. Mapping of lamin A- and progerin-interacting genome regions. Chromosoma 121 (5): 447-64
40. Simonis M, et al. 2006. Nuclear organisation of active and inactive chromatin domains uncovered by chromosome conformation capture-on-chip (4C). Nat. Genet. 38 (11): 1348-54
41. Dubochet J, et al. 1988. Cryo-electron microscopy of vitrified specimens. Q. Rev. Biophys. 21: 129
42. Markenscoff-Papadimitriou E, et al. 2014. Enhancer Interaction Networks as a Means for Singular Olfactory Receptor Expression. Cell 159: 543-557
43. Schoenfelder S, et al. 2010. Preferential associations between co-regulated genes reveal a transcriptional interactome in erythroid cells. Nat. Genet. 42: 53-61
44. Min, I. M. et al. Regulating RNA polymerase pausing and transcription elongation in embryonic stem cells. *Genes Dev.* 25, 742-54 (2011).
45. Whyte, W. a et al. Master transcription factors and mediator establish super-enhancers at key cell identity genes. *Cell* 153, 307-19 (2013).
46. Mayer, R. et al. Common themes and cell type specific variations of higher order chromatin arrangements in the mouse. *BMC Cell Biol.* 6, 44-66 (2005).
47. Liu, Z. et al. 3D imaging of Sox2 enhancer clusters in embryonic stem cells. *Elife* 3, 1-29 (2014).
48. Pombo, a et al. Regional specialization in human nuclei: visualization of discrete sites of transcription by RNA polymerase III. *EMBO J.* 18, 2241-53 (1999).
49. Osborne, C. S. et al. Active genes dynamically colocalize to shared sites of ongoing transcription. *Nat. Genet.* 36, 1065-71 (2004).
50. Peric-Hupkes, D. et al. Molecular Maps of the Reorganization of Genome-Nuclear Lamina Interactions during Differentiation. *Mol. Cell* 38, 603-613 (2010).
51. Branco, M. R., Branco, T., Ramirez, F. & Pombo, A. Changes in chromosome organization during PHA-activation of resting human lymphocytes measured by cryo-FISH. Chromosome Res. 16, 413-26 (2008).
52. Dey, S. S., et al. Integrated genome and transcriptome sequencing from the same cell. Nat. Biotechnol. 33, 285-289 (2015).
53. Binder, K. Applications of Monte Carlo methods to statistical physics. Reports Prog. Phys. 60, 487-559 (1999)
54. Northcott P A. et al. Enhancer hijacking activates GFI1 family oncogenes in medulloblastoma. Nature 511, 428-434 (2014).
55. Lettice L A, et al. Enhancer-adoption as a mechanism of human developmental disease. Hum. Mutat. 32, 1492-9 (2011)
56. Ing-Simmons et al. Spatial enhancer clustering and regulation of enhancer-proximal genes by cohesin. Genome Res. 25: 504-513 (2015)
57. Smemo et al. 2014 Obesity-associated variants within FTO form long-range functional connections with IRX3. Nature 507, 371
58. Williamson, I. et al. 2014. Spatial genome organization: contrasting views from chromosome conformation capture and fluorescence in situ hybridization. Genes Dev. 28, 2778-2791
59. Oeffinger M, et al, 2007 Comprehensive analysis of diverse ribonucleoprotein complexes. Nat Methods. 4, 951-6;

60. Hakhverdyan et al. 2015. Rapid, optimized interactomic screening. Nature Methods 12, 553
61. Pauciullo A, et al. 2014 Development of a sequential multicolor-FISH approach with 13 chromosome-specific painting probes for the rapid identification of river buffalo (Bubalus bubalis, 2n=50) chromosomes. J Appl Genet. 55(3):397-401. doi: 10.1007/s13353-014-0207-z.
62. Leshner M, et al. Locus-specific gene repositioning in prostate cancer. Mol Biol Cell. 2015. pii: mbc.E15-05-0280. [Epub ahead of print]
63. Meaburn K J, et al. 2009 Disease-specific gene repositioning in breast cancer. J Cell Biol.; 187(6):801-12. doi: 10.1083/jcb.200909127.
64. Barutcu A R, et al. 2015. Chromatin interaction analysis reveals changes in small chromosome and telomere clustering between epithelial and breast cancer cells. Genome Biol. 16(1):214. doi: 10.1186/s13059-015-0768-0).
65. Yue, F. et al. A comparative encyclopedia of DNA elements in the mouse genome. Nature 515, 355-364 (2014).

The invention claimed is:

1. A method of determining spatial proximity of a plurality of nucleic acid loci in a cellular compartment comprising nucleic acids, wherein the cellular compartment is derived from a cell or is a prokaryotic cell, comprising:
   (a) cryosectioning a plurality of cellular compartments to obtain a collection of fractions comprising more than 180 fractions each having a thickness of 70 nm to 1000 nm, thereby separating nucleic acid loci from each other depending on their location in one or more of the cellular compartments;
   (b) determining the presence or absence of the plurality of loci in said fractions by sequencing; and
   (c) determining co-segregation of said plurality of loci, wherein spatial proximity is determined by analysing co-segregation with an inferential statistical method, wherein the method does not comprise restriction digest of nucleic acids in combination with ligation between nucleic acids originally present in the compartment.

2. The method of claim 1, wherein the nucleic acids are DNA and/or RNA.

3. The method of claim 1, wherein the compartment is a nucleus of an eukaryotic cell, a mitochondrion or a prokaryotic cell.

4. The method of claim 1, wherein step (a) is preceded by cross-linking with formaldehyde.

5. The method of claim 1, wherein the separation in step (a) is carried out by ultracryosectioning the compartment.

6. The method of claim 1, wherein one compartment is separated into about 5-300 fractions.

7. The method of claim 1, wherein the plurality of loci is two loci to all nucleic acid loci in the compartment.

8. The method of claim 1, wherein the method allows for detection of at least three co-segregating loci.

9. The method of claim 1, wherein the presence or absence of the plurality of loci is determined by next generation sequencing.

10. The method of claim 1, wherein loci are determined to be proximal in space when they co-segregate at a frequency higher than expected from their linear genomic distance on a chromosome.

11. The method of claim 1, wherein the compartment is an eukaryotic nucleus and single nuclear profiles are isolated from sections.

12. The method of claim 1, wherein the nucleic acids are DNA.

13. The method of claim 1, wherein the cell is selected from the group consisting of a bacterium, a protozoan, a plant cell, a fungal cell, and a mammalian cell.

14. The method of claim 13, wherein the cell is a human cell.

15. The method of claim 13, wherein the cell is a cell of a human patient having a disease or disorder.

16. The method of claim 1, wherein the cellular compartment or the cell or a tissues or whole organisms comprising the cellular compartment or the cell is treated with a cross-linking agent before step (a) is carried out.

17. The method of claim 1, wherein cellular ultrastructure is preserved by vitrification.

* * * * *

UNITED STATES PATENT AND TRADEMARK OFFICE
CERTIFICATE OF CORRECTION

PATENT NO. : 10,526,639 B2  
APPLICATION NO. : 15/533890  
DATED : January 7, 2020  
INVENTOR(S) : Ana Pombo et al.

Page 1 of 1

It is certified that error appears in the above-identified patent and that said Letters Patent is hereby corrected as shown below:

In the Claims

<u>Column 36, Claim 16, Line 36:</u>
"compartment or the cell or a tissues or whole organisms comprising" should read: --compartment or the cell or a tissue or whole organism comprising--.

Signed and Sealed this  
Twenty-third Day of February, 2021

Drew Hirshfeld  
*Performing the Functions and Duties of the*  
*Under Secretary of Commerce for Intellectual Property and*  
*Director of the United States Patent and Trademark Office*